US006828327B2

(12) United States Patent
Kuo et al.

(10) Patent No.: US 6,828,327 B2
(45) Date of Patent: Dec. 7, 2004

(54) MACROHETEROCYLIC COMPOUNDS USEFUL AS KINASE INHIBITORS

(75) Inventors: Gee-Hong Kuo, Scotch Plains, NJ (US); Han-Cheng Zhang, Lansdale, PA (US); Catherine Prouty, Doylestown, PA (US); Alan DeAngelis, Pennington, NJ (US); Peter Connolly, New Providence, NJ (US); William V. Murray, Belle Mead, NJ (US); Lan Shen, Clinton, NJ (US); Bruce Conway, Doylestown, PA (US); Keith Demarest, Flemington, NJ (US); Chandra R. Shah, San Diego, CA (US); Bruce E. Maryanoff, Forest Grove, PA (US); Kimberly B. White, North Wales, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/008,982

(22) Filed: Dec. 6, 2001

(65) Prior Publication Data

US 2003/0078280 A1 Apr. 24, 2003

Related U.S. Application Data

(60) Provisional application No. 60/254,161, filed on Dec. 8, 2000.

(51) Int. Cl.$^7$ ...................... A61K 31/44; A61K 31/415; A61K 31/40; A61P 9/00; C07D 487/00
(52) U.S. Cl. ...................... 514/279; 514/403; 514/410; 540/469; 540/472
(58) Field of Search .............................. 514/279, 403, 514/410; 540/469, 472

(56) References Cited

U.S. PATENT DOCUMENTS 6,093,713 A   7/2000 Hudkins et al. ............ 514/211

FOREIGN PATENT DOCUMENTS

| EP | 0 657 458 A | 6/1995 |
|---|---|---|
| EP | 0 735 038 A | 10/1996 |
| WO | WO 97 41127 A | 11/1997 |
| WO | WO 00/38675 A1 | 7/2000 |

OTHER PUBLICATIONS

Ahmad, S., et al., "Expression of the Antisense cDNA for Protein Kinase Cα Attenuates Resistance in Doxorubicin–Resistant MCF–7 Breast Carcinoma Cells," *Molecular Pharmacology*, 1993, 43:858–862.
Akinagaka, S., et al., "Antitumor Activity of UCN–01, a Selective Inhibitor of Protein Kinase C, in Murine and Human Tumor Models," *Cancer Res.*, 1991, 51: 4888–4892.
Bastyr III, E. J. and Lu, J., "Increased Platelet Protein Kinase C–β(PKC–β) in IDDM," *Diabetes*, 1993, 42, (Suppl. 1) 97A.

Begemann, M., et al., "Treatment of Human Glioblastoma Cells with the Staurosporine Derivative CGP 41251 Inhibits CDC2 and CDK2 Kinase Activity and Increases Radiation Sensitivity," *Anticancer Res.* (Greece), 1998, 4A, 18:2275–2282.
Beldhuis, H.J.A., et al., "Long–Term Increase in protein Kinase C–γ and *Muscarinic acetylcholine* Receptor expression in the Cerebral Cortex of Amygdala–Kindled Rats–A Quatitative Immunocytochemical Study," *Neuroscience*, 1993, 55:965–73.
Bender, S. L. and Gauthier, D. R., "an Approach to Pancratistatin from myo–Inositol", Tetrahedron Lett., 1996, 37:13–16.
Berger, J., and Hayes, N. S., "A High–Capacity Assay for Activators of Glucose Incorporation into Glycogen in L6 Muscle Cells," *Anal. Biochem.*, 1998, 261: 159–163.
Bilder, G. E., et al., "Phorbol–12, 13–Dibutyrate–Induced Vasoconstriction in Vivo: Characterization of Response in Genetic Hypertension," *J. Pharmacol. Exp. Ther.*, 1990, 252:526–530.
Bollag, W. B., et al., "Effects of the selective Protein Kinase C Inhibitor, Ro 31–7549, on the Proliferation of cultured Mouse Epidermal Keratinocytes," *J. Invest. Dermatol.*, 1993, 100:240–246.
Chen, Y. H., et al., "Sequence of the Human Glycogen–Associated Regulatory Subunit of Type 1 Protein Phosphatase and Analysis of Its Coding Region and mRNA Level in Muscle From Patients With NIDDM," *Diabetes*, 1994, 43:1234–1241.
Chen, K. S., et al., "Diacylglycerol–Protein Kinase C Signalling In Skeletal Muscle: A Possible Link To Insulin Resistance," *Trans. Assoc. Am. Physicians*, 1991, 104:206–212.
Chin, J. E., et al., "Overexpression of Protein Kinase C Isoenzymes α, βI, γ, and e in Cells Overexpressing the Insulin Receptor," *J. Biol. Chem.*, 1993, 268: 6338–6347.
Cohen P., "Dissection of the Protein Phosphorylation Cascades Involved in Insulin and Growth Factor Action," *Biochem. Soc. Trans.*, 1993, 21:55–567.
Cotter D., et al. "Abnormalities of Wnt signalling in schizophrenia—evidence for neurodevelopmental abnormality," Neuroreport, 1998, 9:1379–1383.
Craven, P. A. and Derubertis, F. R., "Protein Kinase C is Activated in Glomeruli from streptozotocin Diabetic Rats," *J. Clin. Invest.*, 1989, 83:1667–1675.
Cross, D. A. E., et al., "The Inhibition of glycogen synthase kinase–3 by insulin or insulin–like growth factor 1 in the rat sketetal muscle cell line L6 is blocked by wortmannin, but not by rapamycin: evidence that wortmannin blocks activation of the mitogen–activated protein kinase pathway in L6 cells between Ras and Raf", *Biochemical Journal*, 1994, 303:21–26.

(List continued on next page.)

*Primary Examiner*—Brenda Coleman

(57) ABSTRACT

This invention is directed to macroheterocyclic compounds useful as kinase or dual-kinase inhibitors, methods for producing such compounds and methods for treating or ameliorating a kinase or dual-kinase mediated disorder.

5 Claims, No Drawings

OTHER PUBLICATIONS

Danso, D., et al., "The protein kinase C (PKC) inhibitor Ro32–0432 (Ro) significantly enhances mitomycin–C (MMC) induced apoptosis", *Proc. Am. Assoc. Cancer Res.*, 1997, 38:92.

Dekker, L. V., et al., "Protein Kinase C–β contributes to NADPH oxidase activation in neutrophils", *Biochem. J.*, 2000, 347:285–289.

D'Mello, S. R., et al., "Lithium induced Apoptosis in Immature Cerebellar Granule Cells but Promotes Survival of Mature Neurons", *Exp. Cell Res.*, 211:332–338.

Eastman, Q., et al., "Regulation of LEF–1/TCF Transcription factors by Wnt and other signals," Current Opinion in Cell Biology, 1999, 11:233–240.

Eldar–Finkleman, H., et al., "Increased Glycogen Synthase Kinase–3 Activity in Diabetes–and Obesity–Prone C57BL/6J Mice", *Diabetes*, 1999, 48:1–5.

Eldar–Finkleman, H., et al., "Expression and characterization of glycogen synthase kinase–3 mutants and their effect on glycogen synthase activity in intact cells", *PNAS*, 1996, 93:10228–10233.

Eldar–Finkleman, H., and Krebs, E. G., "Phosphorylation of insulin receptor substrate 1 by glycogen synthase kinase 3 impairs insulin action", *PNAS*, 1997, 94:9660–9664.

Embi, N., et al., "Glycogen Synthase Kinase–3 from Rabbit Skeletal Muscle", *Eur. J. Biochem*, 1980, 107:519–527.

Faul, M. M., et al., "A General Approach to the Synthesis of Bisindolylmaleimides: Synthesis of Staurosporine Aglycone", *Synthesis*, 1995, 1511–1516.

Faul, M. M., et al., "Macrocyclic Bisindolylmaleimides: Synthesis by Inter–and Intramolecular Alkylation", *J. Org. Chem*, 1998, 63: 1961–1973.

Gat, U., et al., "De Novo Hair Follicle Morphogenesis and Hair Tumors in Mice Expressing a Truncated β–Catenin in Skin," Cell, 1998, 95:605–614.

Gould, P. L., "Salt selection for basic drugs", International J. Pharm., 1986, 33:201–217.

Gu, X., et al., "Increased Protein Kinase C and Isozyme Redistribution in Pressure–Overload Cardiac Hypertrophy in the Rat", *Circ. Res.*, 1994, 75:926–931.

Hancock, B. C., et al., "Characteristics and significance of the Amorphous State in Pharmaceutical Systems", Journal of Pharmaceutical Sciences, 1997 86:1–12.

Hara, H., et al., "Staurosporine, a Novel Protein Kinase C Inhibitor Prevents Postischemic Neuronal Damage in the Gerbil and Rat", *J. Cereb. Blood Flow Metab.*, 1990, 10:646–653.

Harrington, E.O., et al., "Enhancement of Migration by Protein Kinase Cα and Inhibition of Proliferation and Cell Cycle Progression by Protein Kinase Cδ in Capillary Endothelial Cells", *J. Biol. Chem.*, 1997, 272:7390–7397.

Hegemann, L., et al., "Effects of tiflucarbine as a dual protein kinase C/calmodulin antagonist on proliferation of human keratinocytes and release of reactive oxygen species from human leukocytes", *Arch. Dermatol. Res.*, 1991, 283:456–460.

Hoeflich, K. P., et al., "Requirement for glycogen synthase kinase –3β in cell survival and NF–κ activation", *Nature*, 2000, 406:86–90.

Hong, M., et al., "Lithium Reduces Tau Phosphorylation by Inhibition of Glycogen Synthase Kinase–3", *J. Biol. Chem.*, 1997, 272:25326–32.

Horn, F., et al., "Decreased Protein Kinase C Activity in Psoriatic Versus Normal Epidermis," *J. Invest. Dermatol.*, 1987, 88:220–222.

Hsieh, J., et al., "Human vitamin D receptor is selectively phosphorylated by protein kinase C on serine 51, a residue crucial to its trans–activation function", *Proc. Natl. Acad. Sci. USA*, 1991, 88:9315–9319.

Hsieh, J., et al., "Phosphorylation of the Human Vitamin D Receptor by Protein Kinase C", *J. Biol. Chem.*, 1993, 268,:15118–15126.

Huang, K. P., "The mechanism of protein kinase C activation," *Trends Neurosci.*, 1989, 12:425–432.

Ikeda, S., et al., "Axin, a negative regulator of the Wnt signaling pathway, forms a complex with GSK–3β–dependent phosphorylation of β–catenin," *EMBO J.*, 1998, 17:1371–1384.

Inoguchi, T., et al., "Preferential elevation of protein kinase C isoform βII and diacylglycerol levels in the aorta and heart of diabetic rats: Differential reversibility to glycemic control by islet cell transplantation," *Proc. Natl. Acad. Sci. USA*, 1992, 89:11059–11065.

Ishii, H., et al., "Amelioration of Vascular Dysfunctions in Diabetic Rats by an Oral PKC β Inhibitor", *Science*, 1996, 272:728–731.

Ishii, H., et al., "Protein kinase C activation and its role in the development of vascular complications in diabetes mellitus," *J. Mol. Med.*, 1998, 76:21–31.

Karasik, A., et al., "Increased Protein Kinase C Activity Is Linked to Reduced Insulin Receptor Autophosphorylation in Liver of Starved Rats," *J. Biol. Chem.*, 1990, 265:10226–10231.

Kelly, T. A., et. al., "Novel Non–Nucleoside Inhibitors of Human Immunodeficiency Virus Type 1 Reverse Transcriptase. 6. 2–Indol–3–yl–and 2–Azaindol–3–yl dipyridodiazepinones (1)," *J. Med Chem*. 1997, 40: 2430–2433.

Kobayashi, I., et al., "Platelet–activating factor modulates microvascular transport by stimulation of protein kinase C," *Amer. Phys. Soc.*, 1994, H1214–H1220.

Konig, A., et al., "The protein kinase C inhibitor RO 32–0432 enhances fludarabine–induced apoptosis in WSU–CLL chronic lymphocytic leukemia cells," *Blood*, 1997, 90, 10, Suppl. 1 Pt. 2).

Lee, T–S., et al., "Differential Regulation of Protein Kinase C and (Na,K)—Adenosine Triphosphatase Activities by Elevated Glucose Levels in Retinal Capillary Endothelial Cells," *J. Clin. Invest.*, 1989, 83:90–94.

Lee, T–S., et al., "Activation of protein kinase C by elevation of glucose concentration: Proposal for a mechanism in the development of diabetic vascular complications," *Proc. Natl. Acad. Sci. USA*, 1989, 86:5141–5145.

Leitges, M., et al., "Immunodeficiency in Protein Kinase Cβ–Deficient Mice," *Science*, 1996, 273:788–789.

Lijam N., et al., "Social Interaction and Sensorimotor Gating Abnormalities in Mice Lacking Dvll", *Cell*, 1997, 90:895–905.

Magee, D. I and Beck, E. J., "The use of the Ramberg–Backlund rearrangement for the formation of aza–macrocycles: a total synthesis of manzamine C," *Can. J. Chem.*, 2000, 78:1060–1066.

Malmberg, A. B., et al., "Preserved Acute Pain and Reduced Neuropathic Pain in Mice Lacking PKCγ," Science 1997, 278:279–283.

Manji, H. K., et al., "Modulation of CNS Signal Transduction Pathways and Gene Expression by Mood–Stabilizing Agents: Therapeutic Implications," *J. Clin. Psychiatry*, 1999, 60:27–39 (suppl 2 for review).

Matsumoto, H. and Sasaki, Y., "Staurosporine, A Protein Kinase C Inhibitor Interferes With Proliferation of Arterial Smooth Muscle Cells," *Biochem. Biophys. Res. Commun.*, 1989, 158:105–109.

Meyer, T., et al., "A Derivative of Staurosporine (CGP 41 251) Shows Selectivity For Protein Kinase C Inhibition and In Vitro Anti–Proliferation As Well As In Vivo Anti–Tumor Activity," *Int. J. Cancer*, 1989, 43:851–856.

Miletic, V., et al., "Loose ligation of the rat sciatic nerve is accompanied by changes in the subcellular content of protein kinase C beta II and gama in the spinal dorsal horn," *Neurosci. Lett.*, 2000, 288:199–202.

Muid, R. E., et al., "A novel conformationally restricted protein kinase C inhibitor, Ro 31–8425, inhibits human neutrophil superoxide generation by soluble, particulate and post–receptor stimuli," *FEBS Lett.*, 1990, 293:169–172.

Mulqueen, M. J., et al., "Oral, anti–inflammatory activity of a potent, selective, protein kinase C inhibitor," *Agents Actions*, 1992, 37:85–89.

Murray, N. R., et al., "Protein Kinase C Isotypes in Human Erythroleukemia (K562) Cell Proliferation and Differentiation," *J. Biol. Chem.*, 1993, 268: 15847–15853.

Nagpala, P.G., et al., "Protein Kinase C β(1) Overexpression Augments Phorbol Ester–Induced Increase in Endothelial Permeability," *J. Cell Physiol.*, 1996, 166:249–55.

Nechushtan, H., et al., "Inhibition of degranulation and interleukin–6 production in mast cells derived from mice deficient in protein kinase Cβ," *Blood*, 2000 (Mar.), 95(5):1752–1757.

Nonaka, S. and Chuang, D–M., "Neuroprotective effects of chronic lithium n focal cerebral ischemia in rats," *Neuroreport*, 1998, 9(9):2081–2084.

Pap, M. and Cooper, G. M., "Role of Glycogen Synthase Kinase–3 in the Phosphatidylinositol 3–Kinase/Akt Cell Survival Pathway," *J. Biol. Chem.*, 1998, 273:19929–19932.

Parker, P.J., et al., "Glycogen Synthase from Rabbit Skeletal Muscle; Effect of Insulin on the State of Phosphorylation of the Seven Phosphoserine Residues in vivo," *Eur. J. Biochem.*, 1983, 130:227–234.

Rabbi, M.F., et al., "The cAMP–Dependent Protein Kinase A and Protein Kinase C–β Pathways Synergistically Interact to Activate HIV–1 Transcription in Latently Infected Cells of Monocyte/Macrophage Lineage," *Virology*, 1998, 245(2):257–69.

Raynaud, F. and Evain–Brion, D., "Protein kinase C activity in normal and psoriatic cells: cultures of fibroblasts and lymphocytes," *Br. J. Dermatol.*, 1991, 124:542–546.

Ren, S. et al., "Protein kinase C–β mediates lipoprotein–induced generation of PAI–1 from vascular endothelial cells," *Am. J. Physiol.*, 2000, 278:E656–E662.

Rotenberg, S. A., "Protein Kinase C in Neoplastic Cells" Biochemical and Molecular Aspects of Selected Cancers, 1991 1(2):25–73.

Sauma, S., et al., "Protein Kinase Cβ1 and Protein Kinase Cβ2 Activate p57 Mitogen–activated Protein Kinase and Block Differentiation in Colon Carcinoma Cells(1)," *Cell Growth Differ.*, 1996, 7(5):587–94.

Shibata, S., et al., "Neuroprotective effect of protein kinase C inhibitors on oxygen/glucose free–induced decreases I 2–deoxyglucose uptake and CA1 field potentials in rat hippocampal slices," *Brain Res.*, 1992, 594:290–294.

Shimohama, S., et al., "Assessment of protein kinase C isozymes by two–site enzyme immunoassay in human brains and changes in Alzheimer's disease," *Neurology*, 1993, 43:1407–1413.

Slater, M.J., et al., "Indolocarbazoles: Potent, Selective Inhibitors of Human Cytomegalovirus Replication," *Biorg. & Med. Chem.*, 1999, 7:1067–1074.

Sonoki, H., et al., "The role of protein kinase C in left ventricular relaxation impaired by global ischemia," *Kokyu to Junkan*, 1989 37:669–674 (English Abstract attached).

Srivastava A.K. and Pandey S.K., "Potential mechanism (s) involved in the regulation of glycogen synthesis by insulin," *Mol. and Cellular Biochem.*, 1998, 182:135–141.

Strasser, R. H., et al., "Selective Expresion of Cardiac Protein Kinase C–Isoforms in Chronic Heart Failure and Myocardial Hypertrophy," *Circulation*, 1996, 94:I551.

Teicher, B.A., et al.,"Antiangiogenic and Antitumor Effects of a Protein Kinase Cβ Inhibitor in Human T98G Glioblastoma Multiforme Xenografts," *Clinical Cancer Research*, 2001 U:634–640.

Teicher, B.A., et al., "Therapeutic potentiation by a protein kinase Cb Inhibitor (LY333531) along with radiation or chemotherapy," *Proc. Am. Assoc. Cancer Res.*, 1998, 39(89 Meet.):384.

Tesfamariam, B., et al., "Elevated Glucose Impairs Endothelium–dependent Relaxation by Activating Protein Kinase C," *J. Clin. Invest.*, 1991, 87:1643–1648).

Toullec, D., et al., "The Bisindolylmaleimide GF 109203X Is a Potent and Selective Inhibitor of Protein Kinase C*," *J. Biol. Chem.*, 1991, 266:15771–15781.

Twomey B., et al., "The Effect of New Potent Selective Inhibitors of Protein Kinase C on the Neutrophil Respiratory Burst," *Biochem. Biophys. Res. Commun.*, 1990, 171:1087–1092.

Villar–Palasi C. and Larner J., "Insulin–mediated effect on the activity of UDPG–glycogen transglucosylase of muscle," *Biochim. Biophys. Acta*, 1960, 39: 171–173.

Wakasaki, H., et al., "Targeted overexpression of protein kinase C β2 isoform in myocardium causes cardiomyopathy" *Proc. Natl. Acad. Sci. USA*, 1997, 94: 9320–9325.

Wolf, B. A., et al., "Diacylglycerol Accumulation and Microvascular Abnormalities Induced by Elevated Glucose Levels," *J. Clin. Invest.*, 1991, 87:31–38.

Xia, P., et al., "Characterization of Vascular Endothelial Growth Factor's Effect on the Activation of Protein Kinase C, Its Isoforms, and Endothelial Cell Growth," *J. Clin. Invest.*, 1996, 98:2018.

Yan, S–F, et al., "Protein Kinase C–β and Oxygen Deprivation," *J. Biol. Chem.*, 2000, 275(16):11921–11928.

Zhao, J., et al., "The Expression of Constitutively Active Isotypes of Protein Kinase C to Investigate Preconditioning*," *J. Bio. Chem.*, 1998, 273:23072.

GenBank Accession #U93306 1998.

Guojian Xie et al.: "Protein Kinase C–alpha Inhibitors: Structure–activity Relationships in bis–indole series", Bioorganic & Medicinal Chemistry Letters, 1995, pp. 497–500, vol. 5, No. 5, XP004135732 Oxford, GB, ISSN: 0860–894X.

Ingeborg Hers et al.: "The protein kinase C inhibitors and bisindolylmaleimide I (GF 109203X) and IX (Ro 31–8220) are potent inhibitors of glycogen synthase kinase–3 activity": Febs Letters., 1999, pp. 433–436, vol. 460. XP004260484 Elsevier Science Publishers, Amsterdam NL, ISSN: 0014–5793.

Kleinschroth J., et al.: "Novel Indolocarbazole Protein Kinase C inhibitors with improved biochemical and physiochemical properties", Bioorganic & Medicinal Chemistry Letters,. 1995, pp. 55–60, vol. 5, No. 1, XP004135789, Oxford, GB, ISSN: 0960–894X.

PCT International Search report PCT/US01/47866 dated May 02, 2002.

MACROHETEROCYLIC COMPOUNDS USEFUL AS KINASE INHIBITORS

CROSS REFERENCE TO RELATED APPLICATIONS

This application claims priority from U.S. provisional application Ser. No. 60/254,161, filed Dec. 8, 2000, which is hereby incorporated by reference.

FIELD OF THE INVENTION

This invention is directed to certain novel macroheterocyclic compounds, methods for producing such compounds and methods for treating or ameliorating a kinase or dual-kinase mediated disorder. More particularly, this invention is directed to macroheterocyclic 1H-indole, 1H-pyrrolo[2,3-b]pyridine, 1H-pyrazolo[3,4-b]pyridine, and 1H-indazole compounds useful as selective kinase or dual-kinase inhibitors, methods for producing such compounds and methods for treating or ameliorating a kinase or dual-kinase mediated disorder.

BACKGROUND OF THE INVENTION

U.S. Pat. No. 5,624,949 to Heath, Jr., et. al., describes bis-indolemaleimide derivatives of the formula:

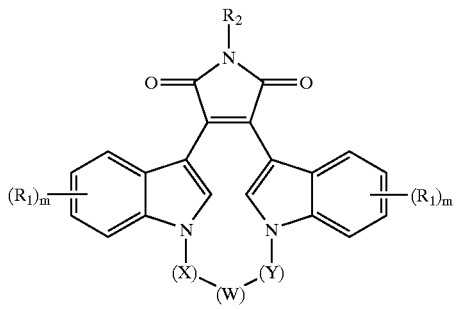

wherein W is —O—, —S—, —SO—, —SO$_2$—, —CO—, $C_2$-$C_6$ alkylene, substituted alkylene, $C_2$-$C_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$_3$—, —NOR$_3$—, —CONH— or —NHCO—; X and Y are independently $C_1$-$C_4$ alkylene, substituted alkylene, or together, X, Y and W combine to form (CH$_2$)$_n$—AA—; R$_1$ is independently hydrogen, halo, $C_1$-$C_4$ alkyl, hydroxy, $C_1$-$C_4$ alkoxy, haloalkyl, nitro, NR$_4$R$_5$ or —NHCO($C_1$-$C_4$) alkyl; R$_2$ is hydrogen, CH$_3$CO—, NH$_2$ or hydroxy; R$_3$ is hydrogen, (CH$_2$)$_m$aryl, $C_1$-$C_4$ alkyl, —COO($C_1$-$C_4$ alkyl), —CONR$_4$R$_5$, —C(C=NH)NH$_2$, —SO($C_1$-$C_4$ alkyl), —SO$_2$(NR$_4$R$_5$) or —SO$_2$($C_1$-$C_4$ alkyl); R$_4$ and R$_5$ are independently hydrogen, $C_1$-$C_4$ alkyl, phenyl, benzyl, or combine to the nitrogen to which they are bonded to form a saturated or unsaturated 5 or 6 member ring; AA is an amino acid residue; m is independently 0, 1, 2 or 3; and n is independently 2, 3, 4 or 5 as PKC inhibitors and as selective PKCβ-I and PKCβ-II inhibitors.

It is an object of the present invention to provide macroheterocyclic 1H-indole, 1H-pyrrolo[2,3-b]pyridine, 1H-pyrazolo[3,4-b]pyridine, and 1H-indazole compounds useful as a kinase or dual-kinase inhibitor (i.e., a compound capable of inhibiting two or more kinases such as, for example, a kinase selected from protein kinase C or glycogen synthase kinase-3; and, more particularly, a kinase selected from protein kinase C α, protein kinase C β-II, protein kinase C γ or glycogen synthase kinase-3β), methods for their production and methods for treating or ameliorating a kinase or dual-kinase mediated disorder.

SUMMARY OF THE INVENTION

The present invention provides a macroheterocyclic compound of Formula (I):

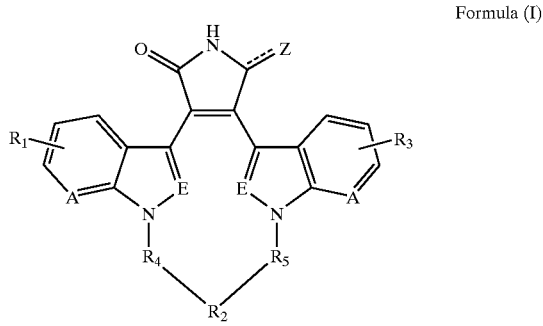

Formula (I)

wherein

A and E are independently selected from the group consisting of a hydrogen substituted carbon atom and a nitrogen atom; wherein

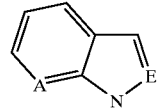

is independently selected from the group consisting of 1H-indole, 1H-pyrrolo[2,3-b]pyridine, 1H-pyrazolo[3,4-b]pyridine and 1H-indazole;

Z is selected from O; alternatively, Z is selected from dihydro; wherein each hydrogen atom is attached by a single bond;

R$_4$ and R$_5$ are independently selected from $C_{1-8}$alkyl, $C_{2-8}$alkenyl and $C_{2-8}$alkynyl optionally substituted with oxo;

R$_2$ is selected from the group consisting of —$C_{1-8}$alkyl-, —$C_{2-8}$alkenyl-, —$C_{2-8}$alkynyl-, —O—($C_{1-8}$)alkyl-O—, —O—($C_{2-8}$)alkenyl-O—, —O—($C_{2-8}$)alkynyl-O—, —C(O)—($C_{1-8}$)alkyl-C(O)— (wherein any of the foregoing alkyl, alkenyl and alkynyl linking groups are straight carbon chains optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, —C(O)O—($C_{1-8}$)alkyl, —$C_{1-8}$alkyl-C(O)O—($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy, hydroxy($C_{1-8}$)alkyl and oxo; and, wherein any of the foregoing alkyl, alkenyl and alkynyl linking groups are optionally substituted with one to two substituents independently selected from the group consisting of heterocyclyl, aryl, heteroaryl, heterocyclyl($C_{1-8}$)alkyl, aryl($C_{1-8}$)alkyl, heteroaryl($C_{1-8}$)alkyl, spirocycloalkyl and spiroheterocyclyl (wherein any of the foregoing cycloalkyl, heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein any of the foregoing heterocyclyl substituents are optionally substituted with oxo)), cycloalkyl, heterocyclyl, aryl, heteroaryl (wherein cycloalkyl, heterocyclyl, aryl and heteroaryl are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl ($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein heterocyclyl is optionally substituted with oxo), —(O—$(CH_2)_{1-6})_{0-5}$—O—, —O—$(CH_2)_{1-6}$—O—$(CH_2)_{1-6}$—O—, —O—$(CH_2)_{1-6}$—O—$(CH_2)_{1-6}$—O—$(CH_2)_{1-6}$—O—, —(O—$(CH_2)_{1-6})_{0-5}$—NR$_6$—, —O—$(CH_2)_{1-6}$—NR$_6$—$(CH_2)_{1-6}$—O—, —O—$(CH_2)_{1-6}$—O—$(CH_2)_{1-6}$—NR$_6$—, —(O—$(CH_2)_{1-6})_{0-5}$—S—, —O—$(CH_2)_{1-6}$—S—$(CH_2)_{1-6}$—O—, —O—$(CH_2)_{1-6}$—O—$(CH_2)_{1-6}$—S—, —NR$_6$—, —NR$_6$—NR$_7$—, —NR$_6$—$(CH_2)_{1-6}$—NR$_7$—, —NR$_6$—$(CH_2)_{1-6}$—NR$_7$—$(CH_2)_{1-6}$—NR$_8$—, —NR$_6$—C(O)—, —C(O)—NR$_6$—, —C(O)—$(CH_2)_{0-6}$—NR$_6$—$(CH_2)_{0-6}$—C(O)—, —NR$_6$—$(CH_2)_{0-6}$—C(O)—$(CH_2)_{1-6}$—C(O)—$(CH_2)_{0-6}$—NR$_7$—, —NR$_6$—C(O)—, —C(O)—NR$_6$—, —NR$_6$—C(NR$_7$)—NR$_8$—, —O—$(CH_2)_{1-6}$—NR$_6$—$(CH_2)_{1-6}$—S—, —S—$(CH_2)_{1-6}$—NR$_6$—$(CH_2)_{1-6}$—O—, —S—$(CH_2)_{1-6}$—NR$_6$—$(CH_2)_{1-6}$—S—, —NR$_6$—$(CH_2)_{1-6}$—S—$(CH_2)_{1-6}$—NR$_7$— and —SO$_2$— (wherein R$_6$, R$_7$ and R$_8$ are independently selected from the group consisting of hydrogen, $C_{1-8}$alkyl, $C_{1-8}$alkoxy($C_{1-8}$)alkyl, carboxyl($C_{1-8}$)alkyl, amino($C_{1-8}$)alkyl (wherein amino is substituted with a substituent independently selected from the group consisting of hydrogen and $C_{1-4}$alkyl), hydroxy($C_{1-8}$)alkyl, heterocyclyl($C_{1-8}$)alkyl, aryl($C_{1-8}$)alkyl and heteroaryl ($C_{1-8}$)alkyl (wherein the foregoing heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein heterocyclyl is optionally substituted with oxo));

with the proviso that, if A and E are selected from a hydrogen substituted carbon atom, then R$_2$ is selected from the group consisting of —C$_{2-8}$alkynyl-, —O—($C_{1-8}$)alkyl-O—, —O—($C_{2-8}$)alkenyl-O—, —O—($C_{2-8}$)alkynyl-O—, —C(O)—($C_{1-8}$)alkyl-C(O)— (wherein any of the foregoing alkyl, alkenyl and alkynyl linking groups are straight carbon chains optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl ($C_{1-8}$)alkyl, —C(O)O—($C_{1-8}$)alkyl, —$C_{1-8}$alkyl-C(O)O—($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy, hydroxy($C_{1-8}$)alkyl and oxo; and, wherein any of the foregoing alkyl, alkenyl and alkynyl linking groups are optionally substituted with one to two substituents independently selected from the group consisting of heterocyclyl, aryl, heteroaryl, heterocyclyl($C_{1-8}$)alkyl, aryl($C_{1-8}$)alkyl, heteroaryl-($C_{1-8}$)alkyl, spirocycloalkyl and spiroheterocyclyl (wherein any of the foregoing cycloalkyl, heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl ($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein any of the foregoing heterocyclyl substituents are optionally substituted with oxo)), cycloalkyl (wherein cycloalkyl is optionally substituted with one to four substituents independently selected from the group consisting of $C_{1-8}$alkyl, $C_{1-8}$alkoxy, $C_{1-8}$alkoxy($C_{1-8}$))alkyl, carboxyl, carboxyl($C_{1-8}$)alkyl, amino (substituted with a substituent independently selected from the group consisting of hydrogen and $C_{1-4}$alkyl), amino($C_{1-8}$) alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$) alkyl), —(O—$(CH_2)_{1-6})_{1-5}$—O—, —O—$(CH_2)_{1-6}$—O—$(CH_2)_{1-6}$—O—, —O—$(CH_2)_{1-6}$—O—$(CH_2)_{1-6}$—O—$(CH_2)_{1-6}$—O—, —(O—$(CH_2)_{1-6})_{1-5}$—NR$_6$—, —O—$(CH_2)_{1-6}$—NR$_6$—$(CH_2)_{1-6}$—O—, —O—$(CH_2)_{1-6}$—O—$(CH_2)_{1-6})_{0-5}$—S—, —O—$(CH_2)_{1-6}$—S—$(CH_2)_{1-6}$—O—, —O—$(CH_2)_{1-6}$—O—$(CH_2)_{1-6}$—S—, —NR$_6$—NR$_7$—, —NR$_6$—$(CH_2)_{1-6}$—NR$_7$—, —NR$_6$—$(CH_2)_{1-6}$—NR$_7$—$(CH_2)_{1-6}$—NR$_8$—, —NR$_9$—C(O)—, —C(O)—, —C(O)—NR$_9$—, —C(O)—$(CH_2)_{0-6}$—NR$_6$—$(CH_2)_{0-6}$—C(O)—, —NR$_6$—$(CH_2)_{0-6}$—C(O)—$(CH_2)_{1-6}$—C(O)—$(CH_2)_{0-6}$—NR$_7$—, —NR$_6$—C(O)—NR$_7$—, —NR$_6$—C(NR$_7$)—NR$_8$—, —O—$(CH_2)_{1-6}$—NR$_6$—$(CH_2)_{1-6}$—S—, —S—$(CH_2)_{1-6}$—NR$_6$—$(CH_2)_{1-6}$—O—, —S—$(CH_2)_{1-6}$—NR$_6$—$(CH_2)_{1-6}$—S— and —NR$_6$—$(CH_2)_{1-6}$—S—$(CH_2)_{1-6}$—NR$_7$— (wherein R$_6$, R$_7$ and R$_8$ are independently selected from the group consisting of hydrogen, $C_{1-8}$alkyl, $C_{1-8}$alkoxy($C_{1-8}$)alkyl, carboxyl($C_{1-8}$)alkyl, amino($C_{1-8}$)alkyl (wherein amino is substituted with a substituent independently selected from the group consisting of hydrogen and $C_{1-4}$alkyl), hydroxy($C_{1-8}$)alkyl, heterocyclyl($C_{1-8}$)alkyl, aryl($C_{1-8}$) alkyl and heteroaryl($C_{1-8}$)alkyl (wherein the foregoing heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein heterocyclyl is optionally substituted with oxo); and, wherein $R_8$ is selected from the group consisting of $C_{1-8}$alkyl, $C_{1-8}$alkoxy($C_{1-8}$)alkyl, carboxyl($C_{1-8}$)alkyl, amino($C_{1-8}$)alkyl (wherein amino is substituted with a substituent independently selected from the group consisting of hydrogen and $C_{1-4}$alkyl), hydroxy($C_{1-8}$)alkyl, heterocyclyl($C_{1-8}$)alkyl, aryl($C_{1-8}$)alkyl and heteroaryl($C_{1-8}$)alkyl (wherein the foregoing heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein heterocyclyl is optionally substituted with oxo)); and, $R_1$ and $R_3$ are independently selected from the group consisting of hydrogen, $C_{1-8}$alkyl, $C_{2-8}$alkenyl, $C_{2-8}$alkynyl (wherein alkyl, alkenyl and alkynyl are optionally substituted with a substituent selected from the group consisting of $C_{1-8}$alkoxy, alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), (halo)$_{1-3}$, (halo)$_{1-3}$($C_{1-8}$)alkyl, (halo)$_{1-3}$($C_{1-8}$)alkoxy, hydroxy, hydroxy($C_{1-8}$)alkyl and oxo), $C_{1-8}$alkoxy, $C_{1-8}$alkoxycarbonyl, (halo)$_{1-3}$($C_{1-8}$)alkoxy, $C_{1-8}$alkylthio, aryl, heteroaryl (wherein aryl and heteroaryl are optionally substituted with a substituent selected from the group consisting of $C_{1-8}$alkyl, $C_{1-8}$alkoxy, alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl), amino (substituted with a substituent independently selected from the group consisting of hydrogen and $C_{1-4}$alkyl), cyano, halogen, hydroxy and nitro;

and pharmaceutically acceptable salts thereof.

The present invention is directed to macroheterocyclic compounds useful as a selective kinase or dual-kinase inhibitor; preferably as inhibitors of kinases selected from protein kinase C or glycogen synthase kinase-3; and, more particularly, a kinase selected from protein kinase C α, protein kinase C β-II, protein kinase C γ or glycogen synthase kinase-3β.

The present invention is also directed to methods for producing the instant macroheterocyclic compounds and pharmaceutical compositions and medicaments thereof.

The present invention is further directed to methods for treating or ameliorating a kinase or dual-kinase mediated disorder. In particular, the method of the present invention is directed to treating or ameliorating a kinase mediated disorder such as, but not limited to, cardiovascular diseases, diabetes, diabetes-associated disorders, inflammatory diseases, immunological disorders, dermatological disorders, oncological disorders and CNS (Central Nervous System) disorders.

DETAILED DESCRIPTION OF THE INVENTION

In a preferred embodiment of the present invention, a compound of Formula (I) is a compound of Formula (Iaa):

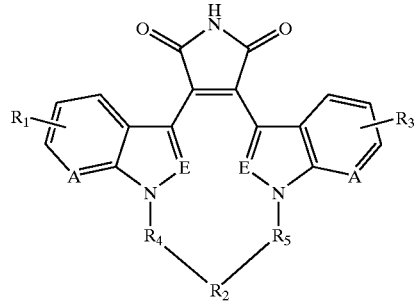

Formula (Iaa)

wherein

A and E are independently selected from the group consisting of a hydrogen substituted carbon atom and a nitrogen atom; wherein

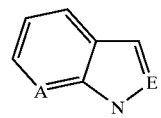

is independently selected from the group consisting of 1H-indole, 1H-pyrrolo[2,3-b]pyridine and 1H-indazole;

and, all other variables are as previously defined;

and, pharmaceutically acceptable salts thereof.

More preferably, a compound of Formula (I), as referenced in the summary, is a compound selected from the group consisting of:

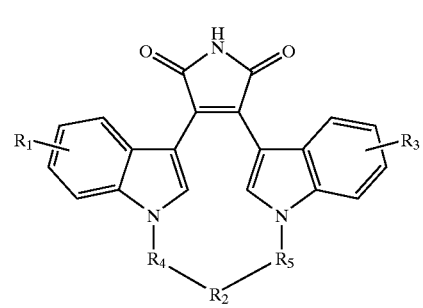

Formula (Ia)

Formula (Ib)
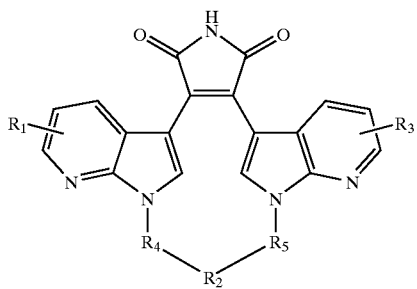
Formula (Ig)
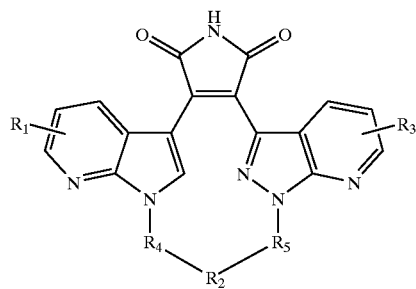
Formula (Ic)
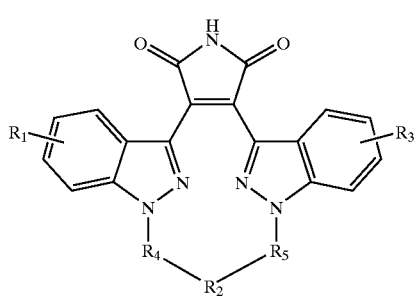
Formula (Ih)
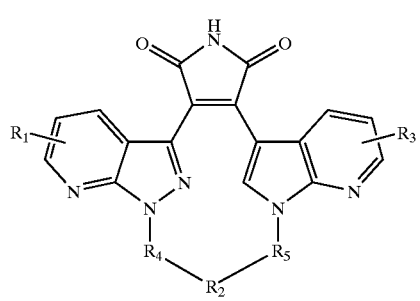
Formula (Id)
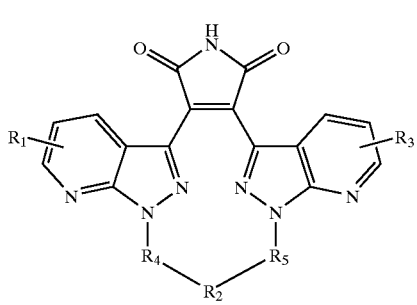
Formula (Ii)
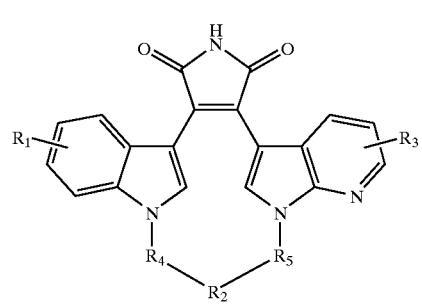
Formula (Ie)
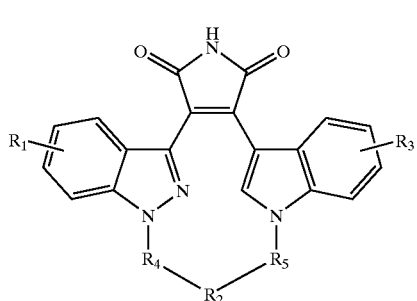
Formula (Ij)
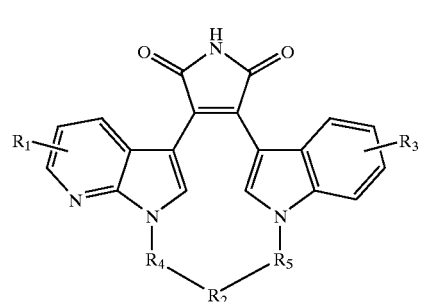
Formula (If)
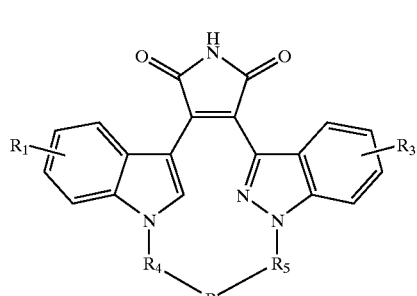
Formula (Ik)
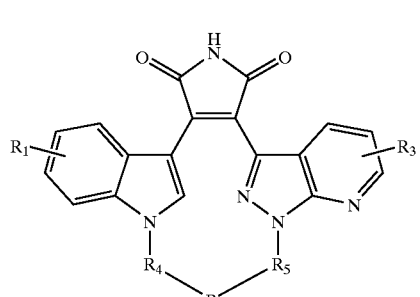

Formula (Il)
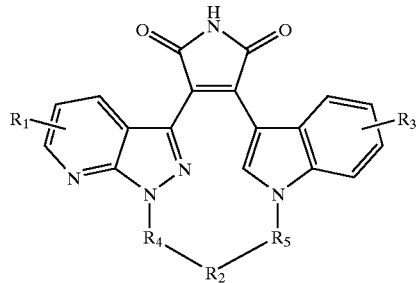
Formula (Ib)
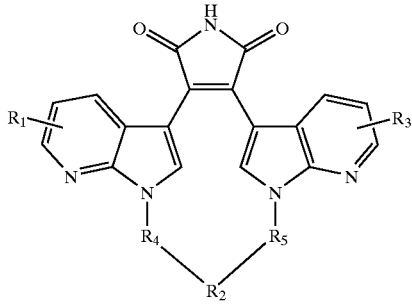
Formula (Im)
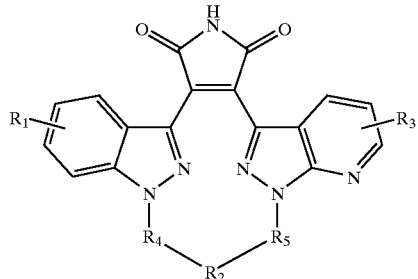
Formula (If)
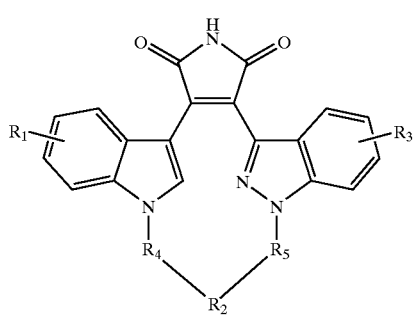
Formula (In)
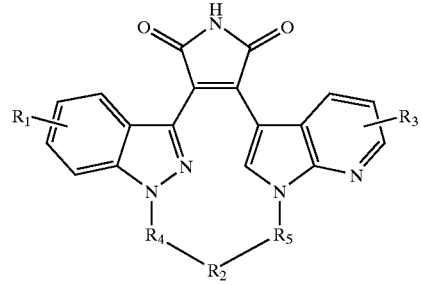
wherein all other variables are as previously defined; and, pharmaceutically acceptable salts thereof.
Formula (Ii)
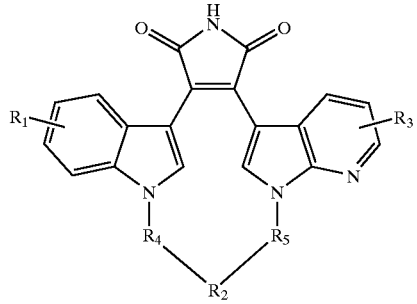
Most preferably, a compound of Formula (I) is a compound selected from the group consisting of:
Formula (Ia)
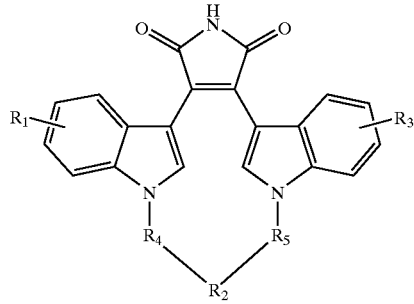
Formula (Ij)
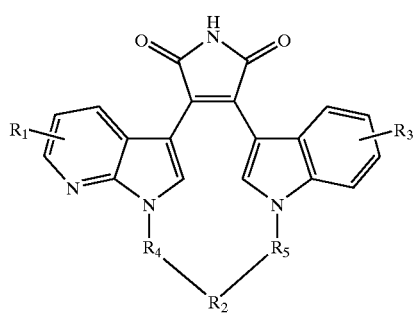

wherein all other variables are as previously defined; and, pharmaceutically acceptable salts thereof.

In a preferred embodiment of the present invention, $R_4$ and $R_5$ are independently selected from $C_{1-6}$alkyl, $C_{2-6}$alkenyl and $C_{2-6}$alkynyl optionally substituted with oxo.

More preferably, $R_4$ and $R_5$ are independently selected from $C_{1-6}$alkyl, $C_{2-6}$alkenyl and $C_{2-6}$alkynyl.

Most preferably, $R_4$ and $R_5$ are independently selected from $C_{1-6}$alkyl.

In a preferred embodiment of the present invention, $R_2$ is selected from the group consisting of —$C_{1-8}$alkyl-, —$C_{2-4}$alkenyl-, —$C_{2-4}$alkynyl-, —O—($C_{1-4}$)alkyl-O—, —O—($C_{2-4}$)alkenyl-O—, —O—($C_{2-4}$)alkynyl-O—, —C(O)—($C_{1-4}$)alkyl-C(O)— (wherein any of the foregoing alkyl, alkenyl and alkynyl linking groups are straight carbon chains optionally substituted with one to four substituents independently selected from the group consisting of $C_{1-4}$alkyl, $C_{1-4}$alkoxy, $C_{1-4}$alkoxy($C_{1-4}$)alkyl, carboxyl, carboxyl($C_{1-4}$)alkyl, —C(O)O—($C_{1-4}$)alkyl, —$C_{1-4}$alkyl-C(O)O—($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$($C_{1-4}$)alkoxy, hydroxy, hydroxy($C_{1-4}$)alkyl and oxo; and, wherein any of the foregoing alkyl, alkenyl and alkynyl linking groups are optionally substituted with one to two substituents independently selected from the group consisting of heterocyclyl, aryl, heteroaryl, heterocyclyl($C_{1-4}$)alkyl, aryl($C_{1-4}$)alkyl, heteroaryl($C_{1-4}$)alkyl, spirocycloalkyl and spiroheterocyclyl (wherein any of the foregoing cycloalkyl, heterocyclyl, aryl and heteroaryl substituents are optionally substituted with one to four substituents independently selected from the group consisting of $C_{1-4}$alkyl, $C_{1-4}$alkoxy, $C_{1-4}$alkoxy($C_{1-4}$)alkyl, carboxyl, carboxyl($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$($C_{1-4}$)alkoxy, hydroxy and hydroxy($C_{1-4}$)alkyl; and, wherein any of the foregoing heterocyclyl substituents are optionally substituted with oxo)), cycloalkyl, heterocyclyl, aryl, heteroaryl (wherein cycloalkyl, heterocyclyl, aryl and heteroaryl are optionally substituted with one to four substituents independently selected from the group consisting of $C_{1-4}$alkyl, $C_{1-4}$alkoxy, $C_{1-4}$alkoxy($C_{1-4}$)alkyl, carboxyl, carboxyl($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$($C_{1-4}$)alkoxy, hydroxy and hydroxy($C_{1-4}$)alkyl; and, wherein heterocyclyl is optionally substituted with oxo), —(O—(CH$_2$)$_{1-6}$)$_{0-5}$—O—, —O—(CH$_2$)$_{1-6}$—O—(CH$_2$)$_{1-6}$—O—, —O—(CH$_2$)$_{1-6}$—O—(CH$_2$)$_{1-6}$—O—(CH$_2$)$_{1-6}$—O—, —(O—(CH$_2$)$_{1-6}$)$_{0-5}$—NR$_6$—, —O—(CH$_2$)$_{1-6}$—NR$_6$—(CH$_2$)$_{1-6}$—O—, —O—(CH$_2$)$_{1-6}$—O—(CH$_2$)$_{1-6}$—NR$_6$—, —O—(CH$_2$)$_{1-6}$)$_{0-5}$—S—, —O—(CH$_2$)$_{1-6}$—S—(CH$_2$)$_{1-6}$—O—, —O—(CH$_2$)$_{1-6}$—O—(CH$_2$)$_{1-6}$—S—, —NR$_6$—NR$_7$—, —NR$_6$—(CH$_2$)$_{1-6}$—NR$_7$—, —NR$_6$—(CH$_2$)$_{1-6}$—NR$_7$—(CH$_2$)$_{1-6}$—NR$_8$—, —NR$_6$—(CO)—, —C(O)—NR$_6$—, —C(O)—(CH$_2$)$_{0-6}$—NR$_6$—(CH$_2$)$_{0-6}$—C(O)—, —NR$_6$—(CH$_2$)$_{0-6}$—C(O)—(CH$_2$)$_{0-6}$—NR$_7$—, —NR$_6$—C(O)—NR$_7$—, —NR$_6$—C(NR$_7$)—NR$_8$—, —O—(CH$_2$)$_{1-6}$—NR$_6$—(CH$_2$)$_{1-6}$—S—, —S—(CH$_2$)$_{1-6}$—NR$_6$—(CH$_2$)$_{1-6}$—O—, —S—(CH$_2$)$_{1-6}$—NR$_6$—(CH$_2$)$_{1-6}$—S—, —NR$_6$—(CH$_2$)$_{1-6}$—S—(CH$_2$)$_{1-6}$—NR$_7$— and —SO$_2$— (wherein $R_6$, $R_7$ and $R_8$ are independently selected from the group consisting of hydrogen, $C_{1-4}$alkyl, $C_{1-4}$alkoxy($C_{1-4}$)alkyl, carboxyl($C_{1-4}$)alkyl, amino($C_{1-4}$)alkyl (wherein amino is substituted with a substituent independently selected from the group consisting of hydrogen and $C_{1-4}$alkyl), hydroxy($C_{1-4}$)alkyl, heterocyclyl($C_{1-4}$)alkyl, aryl($C_{1-4}$)alkyl and heteroaryl($C_{1-4}$)alkyl (wherein the foregoing heterocyclyl, aryl and heteroaryl substituents are optionally substituted with one to four substituents independently selected from the group consisting of $C_{1-4}$alkyl, $C_{1-4}$alkoxy, $C_{1-4}$alkoxy($C_{1-4}$)alkyl, carboxyl, carboxyl($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$($C_{1-4}$)alkoxy, hydroxy and hydroxy($C_{1-4}$)alkyl; and, wherein heterocyclyl is optionally substituted with oxo));

with the proviso that, if A and E are selected from a hydrogen substituted carbon atom, then $R_2$ is selected from the group consisting of —$C_{2-4}$alkynyl-, —O—($C_{1-4}$)alkyl-O—, —O—($C_{2-4}$)alkenyl-O—, —O—($C_{2-4}$)alkynyl-O—, —C(O)—($C_{1-4}$)alkyl-C(O)— (wherein any of the foregoing alkyl, alkenyl and alkynyl linking groups are straight carbon chains optionally substituted with one to four substituents independently selected from the group consisting of $C_{1-4}$alkyl, $C_{1-4}$alkoxy, $C_{1-4}$alkoxy($C_{1-4}$)alkyl, carboxyl, carboxyl($C_{1-4}$)alkyl, —C(O)O—($C_{1-4}$)alkyl, —$C_{1-4}$alkyl-C(O)O—($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$($C_{1-4}$)alkoxy, hydroxy, hydroxy($C_{1-4}$)alkyl and oxo; and, wherein any of the foregoing alkyl, alkenyl and alkynyl linking groups are optionally substituted with one to two substituents independently selected from the group consisting of heterocyclyl, aryl, heteroaryl, heterocyclyl($C_{1-4}$)alkyl, aryl($C_{1-4}$)alkyl, heteroaryl($C_{1-4}$)alkyl, spirocycloalkyl and spiroheterocyclyl (wherein any of the foregoing cycloalkyl, heterocyclyl, aryl and heteroaryl substituents are optionally substituted with one to four substituents independently selected from the group consisting of $C_{1-4}$alkyl, $C_{1-4}$alkoxy, $C_{1-4}$alkoxy($C_{1-4}$)alkyl, carboxyl, carboxyl($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$($C_{1-4}$)alkoxy, hydroxy and hydroxy($C_{1-4}$)alkyl; and, wherein any of the foregoing heterocyclyl substituents are optionally substituted with oxo)), cycloalkyl (wherein cycloalkyl is optionally substituted with one to four substituents independently selected from the group consisting of $C_{1-4}$alkyl, $C_{1-4}$alkoxy, $C_{1-4}$alkoxy($C_{1-4}$)alkyl, carboxyl, carboxyl($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$ ($C_{1-4}$)alkoxy, hydroxy and hydroxy($C_{1-4}$)alkyl), —(O—(CH$_2$)$_{1-6}$)$_{1-5}$—O—, —O—(CH$_2$)$_{1-6}$—O—(CH$_2$)$_{1-6}$—O—, —O—(CH$_2$)$_{1-6}$—O—(CH$_2$)$_{1-6}$—O—(CH$_2$)$_{1-6}$O—, —(O—(CH$_2$)$_{1-6}$)$_{1-5}$—NR$_6$—, —O—(CH$_2$)$_{1-6}$—NR$_6$—(CH$_2$)$_{1-6}$—O—, —O—(CH$_2$)$_{1-6}$—O—(CH$_2$)$_{1-6}$—NR$_6$—, —(O—(CH$_2$)$_{1-6}$)$_{0-5}$—S—, —O—(CH$_2$)$_{1-6}$—S—(CH$_2$)$_{1-6}$—O—, —O—(CH$_2$)$_{1-6}$—S—, —NR$_6$—NR$_7$—, —NR$_6$—(CH$_2$)$_{1-6}$—NR$_7$—, —NR$_6$—(CH$_2$)$_{1-6}$—NR$_7$—(CH$_2$)$_{1-6}$—NR$_8$—, —NR$_9$—C(O)—, —C(O)—NR$_9$—, —C(O)—(CH$_2$)$_{0-6}$—NR$_6$—(CH$_2$)$_{0-6}$—C(O)—, —NR$_6$—(CH$_2$)$_{0-6}$—C(O)—(CH$_2$)$_{1-6}$—C(O)—(CH$_2$)$_{0-6}$—NR$_7$—, —NR$_6$—C(O)—NR$_7$—, —NR$_6$—C(NR$_7$)—NR$_8$—, —O—(CH$_2$)$_{1-6}$—NR$_6$—(CH$_2$)$_{1-6}$—S—, —S—(CH$_2$)$_{1-6}$—NR$_6$—(CH$_2$)$_{1-6}$—O—, —S—(CH$_2$)$_{1-6}$—NR$_6$—(CH$_2$)$_{1-6}$—S— and —NR$_6$—(CH$_2$)$_{1-6}$—S—(CH$_2$)$_{1-6}$—NR$_7$— (wherein R$_6$, R$_7$ and R$_8$ are independently selected from the group consisting of hydrogen, $C_{1-4}$alkyl, $C_{1-4}$alkoxy($C_{1-4}$)alkyl, carboxyl ($C_{1-4}$)alkyl, amino($C_{1-4}$)alkyl (wherein amino is substituted with a substituent independently selected from the group consisting of hydrogen and $C_{1-4}$alkyl), hydroxy($C_{1-4}$)alkyl, heterocyclyl($C_{1-4}$)alkyl, aryl($C_{1-4}$)alkyl and heteroaryl($C_{1-4}$)alkyl (wherein the foregoing heterocyclyl, aryl and heteroaryl substituents are optionally substituted with one to four substituents independently selected from the group consisting of $C_{1-4}$alkyl, $C_{1-4}$alkoxy, $C_{1-4}$alkoxy($C_{1-4}$)alkyl, carboxyl, carboxyl($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$($C_{1-4}$) alkoxy, hydroxy and hydroxy($C_{1-4}$)alkyl; and, wherein heterocyclyl is optionally substituted with oxo); and, wherein R$_9$ is selected from the group consisting of $C_{1-4}$alkyl, $C_{1-4}$alkoxy($C_{1-4}$)alkyl, carboxyl($C_{1-4}$)alkyl, amino($C_{1-4}$)alkyl (wherein amino is substituted with a substituent independently selected from the group consisting of hydrogen and $C_{1-4}$alkyl), hydroxy($C_{1-4}$)alkyl, heterocyclyl($C_{1-4}$)alkyl, aryl($C_{1-4}$)alkyl and heteroaryl ($C_{1-4}$)alkyl (wherein the foregoing heterocyclyl, aryl and heteroaryl substituents are optionally substituted with one to four substituents independently selected from the group consisting of $C_{1-4}$alkyl, $C_{1-4}$alkoxy, $C_{1-4}$alkoxy($C_{1-4}$)alkyl, carboxyl, carboxyl($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$($C_{1-4}$)alkoxy, hydroxy and hydroxy($C_{1-4}$)alkyl; and, wherein heterocyclyl is optionally substituted with oxo)).

More preferably, R$_2$ is selected from the group consisting of —$C_{1-8}$alkyl-(optionally substituted with one to three substituents independently selected from the group consisting of halogen, hydroxy and oxo); aryl, heteroaryl, —(O—(CH$_2$)$_{1-6}$)$_{0-5}$—O—, —O—(CH$_2$)$_{1-6}$—NR$_6$—(CH$_2$)$_{1-6}$—O—, —O—(CH$_2$)$_{1-6}$—S—(CH$_2$)$_{1-6}$—O— and —NR$_6$— (wherein R$_6$, R$_7$ and R$_8$ are independently selected from the group consisting of hydrogen, $C_{1-4}$alkyl and $C_{1-4}$alkoxy ($C_{1-4}$)alkyl);

with the proviso that, if A and E are selected from a hydrogen substituted carbon atom, then R$_2$ is selected from the group consisting of —(O—(CH$_2$)$_{1-6}$)$_{1-5}$—O—, —(O—(CH$_2$)$_{1-6}$)$_{1-5}$—NR$_6$—, —O—(CH$_2$)$_{1-6}$—NR$_6$—(CH$_2$)$_{1-6}$—O— and —NR$_6$—(CH$_2$)$_{1-6}$—NR$_7$—(CH$_2$)$_{1-6}$—NR$_8$— (wherein R$_6$, R$_7$ and R$_8$ are independently selected from the group consisting of hydrogen, $C_{1-4}$alkyl and hydroxy($C_{1-4}$)alkyl).

Most preferably, R$_2$ is selected from the group consisting of —$C_{1-8}$alkyl-(optionally substituted with one to two substituents independently selected from the group consisting of halogen, hydroxy and oxo); phenyl, pyridinyl, —(O—(CH$_2$)$_2$)$_{1-4}$—O—, —O—(CH$_2$)$_2$—NR$_6$—(CH$_2$)$_2$—O—, —O—(CH$_2$)$_2$—S—(CH$_2$)$_2$—O— and —NR$_6$— (wherein R$_6$, R$_7$ and R$_8$ are independently selected from the group consisting of hydrogen, $C_{1-3}$alkyl and $C_{1-2}$alkoxy($C_{1-2}$) alkyl);

with the proviso that, if A and E are selected from a hydrogen substituted carbon atom, then R$_2$ is selected from the group consisting of —(O—(CH$_2$)$_2$)$_{1-4}$—O—, —(O—(CH$_2$)$_2$)$_2$—NR$_6$—, —O—(CH$_2$)$_2$—NR$_6$—(CH$_2$)$_2$—O— and —NR$_6$—(CH$_2$)$_2$—NR$_7$—(CH$_2$)$_2$—NR$_8$— (wherein R$_6$, R$_7$ and R$_8$ are independently selected from the group consisting of hydrogen, $C_{1-3}$alkyl and hydroxy($C_{1-2}$)alkyl).

In a preferred embodiment of the present invention, R$_1$ and R$_3$ are independently selected from the group consisting of hydrogen, $C_{1-4}$alkyl, $C_{2-4}$alkenyl, $C_{2-4}$alkynyl (wherein alkyl, alkenyl and alkynyl are optionally substituted with a substituent selected from the group consisting of $C_{1-4}$alkoxy, alkoxy($C_{1-4}$)alkyl, carboxyl, carboxyl($C_{1-4}$)alkyl, amino (substituted with a substituent independently selected from the group consisting of hydrogen and $C_{1-4}$alkyl), amino ($C_{1-4}$)alkyl (wherein amino is substituted with a substituent independently selected from the group consisting of hydrogen and $C_{1-4}$alkyl), (halo)$_{1-3}$, (halo)$_{1-3}$($C_{1-4}$)alkyl, (halo)$_{1-3}$ ($C_{1-4}$)alkoxy, hydroxy, hydroxy($C_{1-4}$)alkyl and oxo), $C_{1-4}$alkoxy, $C_{1-4}$alkoxycarbonyl, (halo)$_{1-3}$($C_{1-4}$)alkoxy, $C_{1-4}$alkylthio, aryl, heteroaryl (wherein aryl and heteroaryl are optionally substituted with a substituent selected from the group consisting of $C_{1-4}$alkyl, $C_{1-4}$alkoxy, alkoxy($C_{1-4}$) alkyl, carboxyl, carboxyl($C_{1-4}$)alkyl, amino (substituted with a substituent independently selected from the group consisting of hydrogen and $C_{1-4}$alkyl), amino($C_{1-4}$)alkyl (wherein amino is substituted with a substituent independently selected from the group consisting of hydrogen and $C_{1-4}$alkyl), halogen, (halo)$_{1-3}$($C_{1-4}$)alkyl, (halo)$_{1-3}$($C_{1-4}$) alkoxy, hydroxy and hydroxy($C_{1-4}$)alkyl), amino (substituted with a substituent independently selected from the group consisting of hydrogen and $C_{1-4}$alkyl), cyano, halogen, hydroxy and nitro.

More preferably, R$_1$ and R$_3$ are independently selected from the group consisting of hydrogen, $C_{1-4}$alkyl (optionally substituted with a substituent selected from the group consisting of $C_{1-4}$alkoxy, amino (substituted with a substituent independently selected from the group consisting of hydrogen and $C_{1-4}$alkyl), (halo)$_{1-3}$, hydroxy and oxo), $C_{1-4}$alkoxy, $C_{1-4}$alkoxycarbonyl, (halo)$_{1-3}$($C_{1-4}$)alkoxy, amino (substituted with a substituent independently selected from the group consisting of hydrogen and $C_{1-4}$alkyl), halogen, hydroxy and nitro.

Most preferably, R$_1$ and R$_3$ are hydrogen.

Exemplified compounds of the present invention include a compound of Formula (Ia) selected from a compound of Formula (Ia1):

Formula (Ia1)

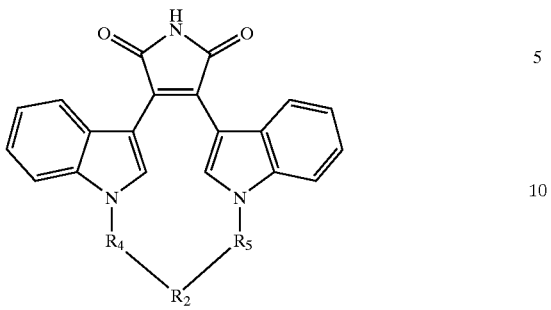

wherein $R_4$, $R_2$ and $R_5$ are dependently selected from:

| Cpd | $R_4$ | $R_2$ | $R_5$ |
|---|---|---|---|
| 4 | —(CH$_2$)$_2$— | —O—(CH$_2$)$_2$—O— | —(CH$_2$)$_2$— |
| 5 | —(CH$_2$)$_2$— | —O—(CH$_2$)$_2$—O—(CH$_2$)$_2$—O— | —(CH$_2$)$_2$— |
| 6 | —(CH$_2$)$_2$— | —O—(CH$_2$)$_2$—O—(CH$_2$)$_2$—O—(CH$_2$)$_2$—O— | —(CH$_2$)$_2$— |
| 7 | —(CH$_2$)$_2$— | —O—(CH$_2$)$_2$—O—(CH$_2$)$_2$—O—(CH$_2$)$_2$—O—(CH$_2$)$_2$—O— | —(CH$_2$)$_2$— |
| 12 | —(CH$_2$)$_2$— | —O—(CH$_2$)$_2$—N(Et)—(CH$_2$)$_2$—O— | —(CH$_2$)$_2$— |
| 13 | —(CH$_2$)$_2$— | —O—(CH$_2$)$_2$—N(Me)—(CH$_2$)$_2$—O— | —(CH$_2$)$_2$— |
| 14 | —(CH$_2$)$_2$— | —O—(CH$_2$)$_2$—N(i-Pr)—(CH$_2$)$_2$—O— | —(CH$_2$)$_2$— |
| 15 | —(CH$_2$)$_2$— | —N(Me)—(CH$_2$)$_2$—N(Me)—(CH$_2$)$_2$—N(Me)— | —(CH$_2$)$_2$— |
| 30 | —(CH$_2$)$_2$— | —O—(CH$_2$)$_2$—N(2-hydroxy-Et)—(CH$_2$)$_2$—O— | —(CH$_2$)$_2$— |
| 31 | —(CH$_2$)$_2$— | —O—(CH$_2$)$_2$—O—(CH$_2$)$_2$—N(Me)— | —(CH$_2$)$_3$— |

Exemplified compounds of the present invention include a compound of Formula (Ib) selected from a compound of Formula (Ib1):

Formula (Ib1)

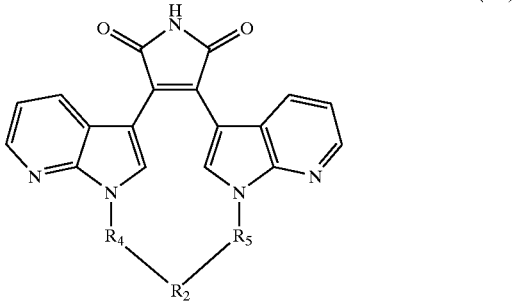

wherein $R_4$, $R_2$ and $R_5$ are dependently selected from:

Exemplified compounds of the present invention include a compound of Formula (If) selected from a compound of Formula (If1):

Formula (If1)

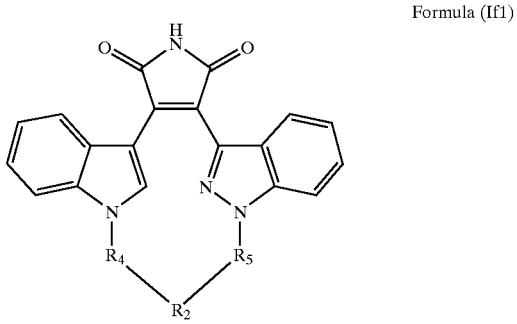

| Cpd | $R_4$ | $R_2$ | $R_5$ |
|---|---|---|---|
| 1 | —(CH$_2$)$_2$— | —O—(CH$_2$)$_2$—O—(CH$_2$)$_2$—O— | —(CH$_2$)$_2$— |
| 2 | —(CH$_2$)$_2$— | —O—(CH$_2$)$_2$—O—(CH$_2$)$_2$—O—(CH$_2$)$_2$—O— | —(CH$_2$)$_2$— |
| 3 | —(CH$_2$)$_2$— | —O—(CH$_2$)$_2$—O—(CH$_2$)$_2$—O—(CH$_2$)$_2$—O—(CH$_2$)$_2$—O— | —(CH$_2$)$_2$— |
| 18 | —(CH$_2$)$_2$— | —O—(CH$_2$)$_2$—N(Et)—(CH$_2$)$_2$—O— | —(CH$_2$)$_2$— |
| 19 | —(CH$_2$)$_2$— | —O—(CH$_2$)$_2$—S—(CH$_2$)$_2$—O— | —(CH$_2$)$_2$— |
| 20 | —(CH$_2$)$_5$— | —NH— | —(CH$_2$)$_5$— |
| 21 | —(CH$_2$)$_5$— | —N(Et)— | —(CH$_2$)$_5$— |
| 22 | —(CH$_2$)$_5$— | —NH— | —(CH$_2$)$_4$— |
| 23 | —(CH$_2$)$_5$— | —N(Et)— | —(CH$_2$)$_4$— |
| 24 | —(CH$_2$)$_4$— | -2,6-pyridinyl- | —(CH$_2$)$_4$— |
| 25 | —(CH$_2$)$_4$— | —C(O)—(CH$_2$)$_2$— | —(CH$_2$)$_4$— |
| 26 | —(CH$_2$)$_4$— | —C(O)— | —(CH$_2$)$_4$— |
| 27 | —CH$_2$— | —CH[R](OH)—(CH$_2$)$_6$—CH[R](OH)— | —CH$_2$— |
| 28 | —(CH$_2$)$_2$— | —O—(CH$_2$)$_2$—O— | —(CH$_2$)$_2$— | wherein $R_4$, $R_2$ and $R_5$ are dependently selected from:

| Cpd | $R_4$ | $R_2$ | $R_5$ |
|---|---|---|---|
| 16 | —(CH$_2$)$_2$— | —O—(CH$_2$)$_2$—N(Me)—(CH$_2$)$_2$—O— | —(CH$_2$)$_2$— |
| 17 | —(CH$_2$)$_2$— | —O—(CH$_2$)$_2$—N(Et)—(CH$_2$)$_2$—O— | —(CH$_2$)$_2$— |
| 29 | —(CH$_2$)$_2$— | —O—(CH$_2$)$_2$—N(2-OMe—Et)—(CH$_2$)$_2$—O— | —(CH$_2$)$_2$— |

Exemplified compounds of the present invention include a compound of Formula (Ii) selected from a compound of Formula (Ii1):

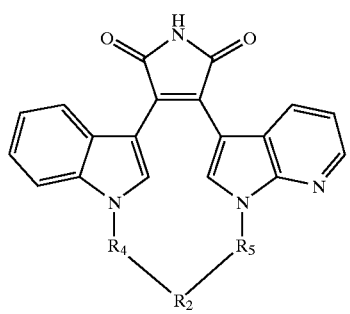

Formula (Ii1)

wherein $R_4$, $R_2$ and $R_5$ are dependently selected from:

| Cpd | $R_4$ | $R_2$ | $R_5$ |
|---|---|---|---|
| 8 | —CH$_2$— | -1,3-phenyl- | —CH$_2$— |
| 9 | —CH$_2$— | -2,6-pyridinyl- | —CH$_2$— |

Exemplified compounds of the present invention include a compound of Formula (Ij) selected from a compound of Formula (Ij1):

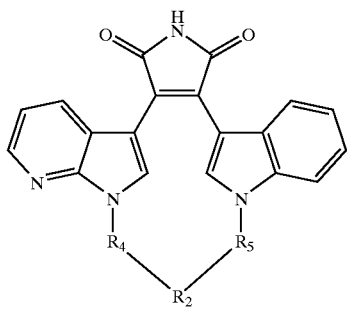

Formula (Ij1)

wherein $R_4$, $R_2$ and $R_5$ are dependently selected from:

| Cpd | $R_4$ | $R_2$ | $R_5$ |
|---|---|---|---|
| 10 | —(CH$_2$)$_2$— | —O—(CH$_2$)$_2$—O— | —CH$_2$— |
| 11 | —(CH$_2$)$_2$— | —O—(CH$_2$)$_2$—O—(CH$_2$)$_2$—O— | —CH$_2$— |

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201–217; J. Pharm. Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds, which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in racemic form or individual enantiomers may be prepared by standard techniques known to those skilled in the art, for example, by enantiospecific synthesis or resolution, formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

Unless specified otherwise, the term "alkyl" refers to a saturated straight or branched chain consisting solely of 1–8 hydrogen substituted carbon atoms; preferably, 1–6 hydrogen substituted carbon atoms; and, most preferably, 1–4 hydrogen substituted carbon atoms. The term "alkenyl" refers to a partially unsaturated straight or branched alkyl chain that contains at least one double bond. The term "alkynyl" refers to a partially unsaturated straight or branched alkyl chain that contains at least one triple bond. The term "alkoxy" refers to —O-alkyl, where alkyl is as defined supra. The term "alkylthio" refers to —S-alkyl, where alkyl is as defined supra. A carboxyl group is a carbonyl with a terminal OH group.

When the straight or branched alkyl chain functions as a linking group and is optionally substituted with amino, halogen, hydroxy or oxo substituents, the branched alkyl chain may be substituted on the linking alkyl chain, the branch of the linking alkyl chain or on both.

The term "cycloalkyl" refers to a saturated or partially unsaturated cyclic alkyl ring consisting of 3–8 hydrogen substituted carbon atoms. Examples include, and are not limited to, cyclopropyl, cyclopentyl, cyclohexyl or cycloheptyl. The term "spirocycloalkyl" refers to a cycloalkyl ring sharing a single ring carbon with another attached ring.

The term "heterocyclyl" refers to a saturated or partially unsaturated ring having five members of which at least one member is a N, O or S atom and which optionally contains one additional O atom or one, two or three additional N atoms, a saturated or partially unsaturated ring having six members of which one, two or three members are a N atom, a saturated or partially unsaturated bicyclic ring having nine members of which at least one member is a N, O or S atom and which optionally contains one, two or three additional N atoms and a saturated or partially unsaturated bicyclic ring having ten members of which one, two or three members are a N atom. Examples include, and are not limited to, pyrrolinyl, pyrrolidinyl, dioxolanyl, imidazolinyl, imidazolidinyl, pyrazolinyl, pyrazolidinyl, piperidinyl, morpholinyl or piperazinyl. The term "spiroheterocyclyl" refers to a heterocyclyl ring sharing a single ring carbon with another attached ring.

The term "aryl" refers to an aromatic monocyclic ring system containing 5–6 hydrogen substituted carbon atoms or an aromatic bicyclic ring system containing 9–14 hydrogen substituted carbon atoms. Examples include, and are not limited to, phenyl, naphthalenyl or anthracenyl.

The term "heteroaryl" refers to an aromatic monocyclic ring system containing five members of which at least one member is a N, O or S atom and which optionally contains one, two or three additional N atoms, an aromatic monocyclic ring having six members of which one, two or three members are a N atom, an aromatic bicyclic ring having nine members of which at least one member is a N, O or S atom and which optionally contains one, two or three additional N atoms and an aromatic bicyclic ring having ten members of which one, two or three members are a N atom. Examples include, and are not limited to, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, quinolinyl or isoquinolinyl.

The term "halo" or "halogen" refers to a fluoro, chloro, bromo or iodo atom.

"Independently" means that when a group is substituted with more than one substituent that the substituents may be the same or different. "Dependently" means that the substituents are specified in an indicated combination of structure variables.

An embodiment of the invention is a pharmaceutical composition comprising a pharmaceutically acceptable carrier and any of the compounds described above. Illustrative of the invention is a pharmaceutical composition made by mixing any of the compounds described above and a pharmaceutically acceptable carrier. Another illustration of the invention is a process for making a pharmaceutical composition comprising mixing any of the compounds described above and a pharmaceutically acceptable carrier. Further illustrative of the present invention are pharmaceutical compositions comprising one or more compounds of this invention in association with a pharmaceutically acceptable carrier.

As used herein, the term "composition" is intended to encompass a product comprising the specified ingredients in the specified amounts, as well as any product which results, directly or indirectly, from combinations of the specified ingredients in the specified amounts.

The compounds of the present invention are selective kinase or dual-kinase inhibitors useful in a method for treating or ameliorating a kinase or dual-kinase mediated disorder. In a preferred embodiment, the kinase is selected from protein kinase C or glycogen synthase kinase-3 and more preferably, the kinase is selected from protein kinase C α, protein kinase C β-II, protein kinase C γ or glycogen synthase kinase-3β. However, as demonstrated in the examples included herein, the compounds of this invention demonstrate inhibitory activity for a number of other kinases as well.

Protein Kinase C Isoforms

Protein kinase C(PKC) is known to play a key role in intracellular signal transduction (cell-cell signaling), gene expression and in the control of cell differentiation and growth. The PKC family is composed of twelve isoforms that are further classified into 3 subfamilies: the calcium dependent classical PKC isoforms alpha (α), beta-I (β-I), beta-II (β-II) and gamma (γ); the calcium independent PKC isoforms delta (δ), epsilon (ε), eta (η), theta (θ) and mu (μ); and, the a typical PKC isoforms zeta (ζ), lambda (λ) and iota (ι).

Certain disease states tend to be associated with elevation of particular PKC isoforms. The PKC isoforms exhibit distinct tissue distribution, subcellular localization and activation-dependent cofactors. For example, the α and β isoforms of PKC are selectively induced in vascular cells stimulated with agonists such as vascular endothelial growth factor (VEGF) (P. Xia, et al., *J. Clin. Invest.*, 1996, 98, 2018) and have been implicated in cellular growth, differentiation, and vascular permeability (H. Ishii, et al., *J. Mol. Med.*, 1998, 76, 21). The elevated blood glucose levels found in diabetes leads to an isoform-specific elevation of the β-II isoform in vascular tissues (Inoguchi, et al., *Proc. Natl. Acad. Sci. USA*, 1992, 89, 11059–11065). A diabetes-linked elevation of the β isoform in human platelets has been correlated with the altered response of the platelets to agonists (Bastyr III, E. J. and Lu, J., *Diabetes*, 1993, 42, (Suppl. 1) 97A). The human vitamin D receptor has been shown to be selectively phosphorylated by PKCβ. This phosphorylation has been linked to alterations in the functioning of the receptor (Hsieh, et al., *Proc. Natl. Acad. Sci. USA*, 1991, 88, 9315–9319; Hsieh, et al., *J. Biol. Chem.*, 1993, 268, 15118–15126). In addition, the work has shown that the β-II isoform is responsible for erythroleukemia cell proliferation while the a isoform is involved in megakaryocyte differentiation in these same cells (Murray, et al., *J. Biol. Chem.*, 1993, 268, 15847–15853).

Cardiovascular Diseases

PKC activity plays an important role in cardiovascular diseases. Increased PKC activity in the vasculature has been shown to cause increased vasoconstriction and hypertension (Bilder, G. E., et al., *J. Pharmacol. Exp. Ther.*, 1990, 252, 526–530). PKC inhibitors block agonist-induced smooth muscle cell proliferation (Matsumoto, H. and Sasaki, Y., *Biochem. Biophys. Res. Commun.*, 1989, 158, 105–109). PKC β triggers events leading to the induction of Egr-1

(Early Growth Factor-1) and tissue factor under hypoxic conditions (as part of the oxygen deprivation-mediated pathway for triggering procoagulant events) (Yan, S-F, et al., *J. Biol. Chem.*, 2000, 275, 16, 11921–11928). PKC β is suggested as a mediator for production of PAI-1 (Plasminogen Activator Inhibitor-1) and is implicated in the development of thrombosis and atherosclerosis (Ren, S, et al., *Am. J. Physiol.*, 2000, 278, (4, Pt. 1), E656–E662). PKC inhibitors are useful in treating cardiovascular ischemia and improving cardiac function following ischemia (Muid, R. E., et al., *FEBS Lett.*, 1990, 293, 169–172; Sonoki, H. et al., *Kokyu-To Junkan*, 1989, 37, 669–674). Elevated PKC levels have been correlated with an increase in platelet function in response to agonists (Bastyr III, E. J. and Lu, J., *Diabetes*, 1993, 42, (Suppl. 1)97A). PKC has been implicated in the biochemical pathway in the platelet-activating factor (PAF) modulation of microvascular permeability (Kobayashi, et al., *Amer. Phys. Soc.*, 1994, H1214–H1220). PKC inhibitors affect agonist-induced aggregation in platelets (Toullec, D., et al., *J. Biol. Chem.*, 1991, 266, 15771–15781). Accordingly, PKC inhibitors may be indicated for use in treating cardiovascular disease, ischemia, thrombotic conditions, atherosclerosis and restenosis.

Diabetes

Excessive activity of PKC has been linked to insulin signaling defects and therefore to the insulin resistance seen in Type II diabetes (Karasik, A., et al., *J. Biol. Chem.*, 1990, 265, 10226–10231; Chen, K. S., et al., *Trans. Assoc. Am. Physicians*, 1991, 104, 206–212; Chin, J. E., et al., *J. Biol. Chem.*, 1993, 268, 6338–6347).

Diabetes-Associated Disorders

Studies have demonstrated an increase in PKC activity in tissues known to be susceptible to diabetic complications when exposed to hyperglycemic conditions (Lee, T-S., et al., *J. Clin. Invest.*, 1989, 83, 90–94; Lee, T-S., et al., *Proc. Natl. Acad. Sci. USA*, 1989, 86, 5141–5145; Craven, P. A. and DeRubertis, F. R., *J. Clin. Invest.*, 1989, 87, 1667–1675; Wolf, B. A., et al., *J. Clin. Invest.*, 1991, 87, 31–38; Tesfamariam, B., et al., *J. Clin. Invest.*, 1991, 87, 1643–1648). For example, activation of the PKC-β-II isoform plays an important role in diabetic vascular complications such as retinopathy (Ishii, H., et al., *Science*, 1996, 272, 728–731) and PKCβ has been implicated in development of the cardiac hypertrophy associated with heart failure (X. Gu, et al., *Circ. Res.*, 1994, 75, 926; R. H. Strasser, et al., *Circulation*, 1996, 94, 1551). Overexpression of cardiac PKCβII in transgenic mice caused cardiomyopathy involving hypertrophy, fibrosis and decreased left ventricular function (H. Wakasaki, et al., *Proc. Natl. Acad. Sci. USA*, 1997, 94, 9320).

Inflammatory Diseases

PKC inhibitors block inflammatory responses such as the neutrophil oxidative burst, CD3 down-regulation in T-lymphocytes and phorbol-induced paw edema (Twoemy, B., et al., *Biochem. Biophys. Res. Commun.*, 1990, 171, 1087–1092; Mulqueen, M. J., et al. *Agents Actions*, 1992, 37, 85–89). PKC β has an essential role in the degranulation of bone marrow-derived mast cells, thus affecting cell capacity to produce IL-6 (Interleukin-6) (Nechushtan, H., et al., *Blood*, 2000 (March), 95, 5, 1752–1757). PKC plays a role in enhanced ASM (Airway Smooth Muscle) cell growth in rat models of two potential risks for asthma: hyperresponsiveness to contractile agonists and to growth stimuli (Ren, S, et al., *Am. J. Physiol.*, 2000, 278, (4, Pt. 1), E656–E662). PKC β-1 overexpression augments an increase in endothelial permeability, suggesting an important function in the regulation of the endothelial barrier (Nagpala, P. G., et al., *J. Cell Physiol.*, 1996, 2, 249–55). PKC β mediates activation of neutrophil NADPH oxidase by PMA and by stimulation of Fcγ receptors in neutrophils (Dekker, L. V., et al., *Biochem. J*, 2000, 347, 285–289). Thus, PKC inhibitors may be indicated for use in treating inflammation and asthma.

Immunological Disorders

PKC may be useful in treating or ameliorating certain immunological disorders. While one study suggests that HCMV (Human Cytomegalovirus) inhibition is not correlated with PKC inhibition (Slater, M. J., et al., *Biorg. & Med. Chem.*, 1999, 7, 1067–1074), another study showed that the PKC signal transduction pathway synergistically interacted with the cAMP-dependent PKA pathway to activate or increase HIV-1 transcription and viral replication and was abrogated with a PKC inhibitor (Rabbi, M. F., et al., *Virology*, 1998 (June 5), 245, 2, 257–69). Therefore, an immunological disorder may be treated or ameliorated as a function of the affected underlying pathway's response to up- or down-regulation of PKC.

PKC β deficiency also results in an immunodeficiency characterized by impaired humoral immune responses and a reduced B cell response, similar to X-linked immunodeficiency in mice and plays an important role in antigen receptor-mediated signal transduction (Leitges, M., et al., *Science* (Wash., D.C.), 1996, 273, 5276, 788–789). Accordingly, transplant tissue rejection may be ameliorated or prevented by suppressing the immune response using a PKC β inhibitor.

Dermatological Disorders

Abnormal activity of PKC has been linked to dermatological disorders characterized by abnormal proliferation of keratinocytes, such as psoriasis (Horn, F., et al., *J. Invest. Dermatol.*, 1987, 88, 220–222; Raynaud, F. and Evain-Brion, D., *Br. J. Dermatol.*, 1991, 124, 542–546). PKC inhibitors have been shown to inhibit keratinocyte proliferation in a dose-dependent manner (Hegemann, L., et al., *Arch. Dermatol. Res.*, 1991, 283, 456–460; Bollag, W. B., et al., *J. Invest. Dermatol.*, 1993, 100, 240–246).

Oncological Disorders

PKC activity has been associated with cell growth, tumor promotion, uncontrolled cell growth and cancer (Rotenberg, S. A. and Weinstein, I. B., *Biochem. Mol. Aspects Sel. Cancer*, 1991, 1, 25–73; Ahmad, et al., *Molecular Pharmacology*, 1993, 43, 858–862); PKC inhibitors are known to be effective in preventing tumor growth in animals (Meyer, T., et al., *Int. J. Cancer*, 1989, 43, 851–856; Akinagaka, S., et al., *Cancer Res.*, 1991, 51, 4888–4892). PKC β-1 and β-2 expression in differentiated HD3 colon carcinoma cells blocked their differentiation, enabling them to proliferate in response to basic FGF (Fibroblast Growth Factor) like undifferentiated cells, increasing their growth rate and activating several MBP (Myelin-Basic Protein) kinases, including p57 MAP (Mitogen-Activated Protein) kinase (Sauma, S., et al., *Cell Growth Differ.*, 1996, 7, 5, 587–94). PKC α inhibitors, having an additive therapeutic effect in combination with other anti-cancer agents, inhibited the growth of lymphocytic leukemia cells (Konig, A., et al., *Blood*, 1997, 90, 10, Suppl. 1 Pt. 2). PKC inhibitors enhanced MMC (Mitomycin-C) induced apoptosis in a time-dependent fashion in a gastric cancer cell-line, potentially indicating use as agents for chemotherapy-induced apoptosis (Danso, D., et al., *Proc. Am. Assoc. Cancer Res.*, 1997, 38, 88 Meet., 92). Therefore, PKC inhibitors may be indicated for use in ameliorating cell and tumor growth, in treating or ameliorating cancers (such as leukemia or colon cancer) and as adjuncts to chemotherapy.

PKC α (by enhancing cell migration) may mediate some proangiogenic effects of PKC activation while PKC δ may direct antiangiogenic effects of overall PKC activation (by inhibiting cell growth and proliferation) in capillary endothelial cells, thus regulating endothelial proliferation and angiogenesis (Harrington, E. O., et al., *J. Biol. Chem.*, 1997, 272, 11, 7390–7397). PKC inhibitors inhibit cell growth and induce apoptosis in human glioblastoma cell lines, inhibit the growth of human astrocytoma xenografts and act as radiation sensitizers in glioblastoma cell lines (Begemann, M., et al., *Anticancer Res.* (Greece), 1998 (July–August), 18, 4A, 2275–82). PKC inhibitors, in combination with other anti-cancer agents, are radiation and chemosensitizers useful in cancer therapy (Teicher, B. A., et al., *Proc. Am. Assoc. Cancer Res.*, 1998, 39, 89 Meet., 384). PKC β inhibitors (by blocking the MAP kinase signal transduction pathways for VEGF (Vascular Endothelial Growth Factor) and bFGF (basic Fibrinogen Growth Factor) in endothelial cells), in a combination regimen with other anti-cancer agents, have an anti-angiogenic and antitumor effect in a human T98G glioblastoma multiforme xenograft model (Teicher, B. A., et al., *Clinical Cancer Research*, 2001 (March), 7, 634–640). Accordingly, PKC inhibitors may be indicated for use in ameliorating angiogenesis and in treating or ameliorating cancers (such as breast, brain, kidney, bladder, ovarian or colon cancers) and as adjuncts to chemotherapy and radiation therapy.

Central Nervous System Disorders

PKC activity plays a central role in the functioning of the CNS (Huang, K. P., *Trends Neurosci.*, 1989, 12, 425–432) and PKC is implicated in Alzheimer's disease (Shimohama, S., et al., *Neurology*, 1993, 43, 1407–1413) and inhibitors have been shown to prevent the damage seen in focal and central ischemic brain injury and brain edema (Hara, H., et al., *J. Cereb. Blood Flow Metab.*, 1990, 10, 646–653; Shibata, S., et al., *Brain Res.*, 1992, 594, 290–294). Accordingly, PKC inhibitors may be indicated for use in treating Alzheimers disease and in treating neurotraumatic and ischemia-related diseases.

The long-term increase in PKC γ (as a component of the phosphoinositide $2^{nd}$ messenger system) and muscarinic acetylcholine receptor expression in an amygdala-kindled rat model has been associated with epilepsy, serving as a basis for the rat's permanent state of hyperexcitability (Beldhuis, H. J. A., et al., *Neuroscience*, 1993, 55, 4, 965–73). Therefore, PKC inhibitors may be indicated for use in treating epilepsy.

The subcellular changes in content of the PKC γ and PKC β-II isoenzymes for animals in an in-vivo thermal hyperalgesia model suggests that peripheral nerve injury contributes to the development of persistent pain (Miletic, V., et al., *Neurosci. Lett.*, 2000, 288, 3, 199–202). Mice lacking PKCγ display normal responses to acute pain stimuli, but almost completely fail to develop a neuropathic pain syndrome after partial sciatic nerve section (Chen, C., et al., *Science* (Wash., D.C.), 1997, 278, 5336, 279–283). PKC modulation may thus be indicated for use in treating chronic pain and neuropathic pain.

PKC has demonstrated a role in the pathology of conditions such as, but not limited to, cardiovascular diseases, diabetes, diabetes-associated disorders, inflammatory diseases, immunological disorders, dermatological disorders, oncological disorders and central nervous system disorders.

Glycogen Synthase Kinase-3

Glycogen synthase kinase-3 (GSK-3) is a serine/threonine protein kinase composed of two isoforms (α and β) which are encoded by distinct genes. GSK-3 is one of several protein kinases which phosphorylate glycogen synthase (GS) (Embi, et al., *Eur. J. Biochem*, 1980, 107, 519–527). The α and β isoforms have a monomeric structure of 49 and 47 kD respectively and are both found in mammalian cells. Both isoforms phosphorylate muscle glycogen synthase (Cross, et al., *Biochemical Journal*, 1994, 303, 21–26) and these two isoforms show good homology between species (human and rabbit GSK-3α are 96% identical).

Diabetes

Type II diabetes (or Non-Insulin Dependent Diabetes Mellitus, NIDDM) is a multifactorial disease. Hyperglycemia is due to insulin resistance in the liver, muscle and other tissues coupled with inadequate or defective secretion of insulin from pancreatic islets. Skeletal muscle is the major site for insulin-stimulated glucose uptake. In this tissue, glucose removed from the circulation is either metabolised through glycolysis and the TCA (tricarboxylic acid) cycle or stored as glycogen. Muscle glycogen deposition plays the more important role in glucose homeostasis and Type II diabetic subjects have defective muscle glycogen storage. The stimulation of glycogen synthesis by insulin in skeletal muscle results from the dephosphorylation and activation of glycogen synthase (Villar-Palasi C. and Lamer J., *Biochim. Biophys. Acta*, 1960, 39, 171–173, Parker P. J., et al., *Eur. J. Biochem.*, 1983, 130, 227–234, and Cohen P., *Biochem. Soc. Trans.*, 1993, 21, 555–567). The phosphorylation and dephosphorylation of GS are mediated by specific kinases and phosphatases. GSK-3 is responsible for phosphorylation and deactivation of GS, while glycogen bound protein phosphatase 1 (PP1 G) dephosphorylates and activates GS. Insulin both inactivates GSK-3 and activates PP1G (Srivastava A. K. and Pandey S. K., *Mol. and Cellular Biochem.*, 1998, 182, 135–141).

Studies suggest that an increase in GSK-3 activity might be important in Type II diabetic muscle (Chen, et al., *Diabetes*, 1994, 43, 1234–1241). Overexpression of GSK-3α and constitutively active GSK-3β (S9A, S9e) mutants in HEK-293 cells resulted in suppression of glycogen synthase activity (Eldar-Finkelman, et al., *PNAS*, 1996, 93, 10228–10233) and overexpression of GSK-3β in CHO cells, expressing both insulin receptor and insulin receptor substrate 1 (IRS-1) resulted in impairment of insulin action (Eldar-Finkelman and Krebs, *PNAS*, 1997, 94, 9660–9664). Recent evidence for the involvement of elevated GSK-3 activity and the development of insulin resistance and Type II diabetes in adipose tissue has emerged from studies undertaken in diabetes and obesity prone C57BL/6J mice (Eldar-Finkelman, et al., *Diabetes*, 1999, 48, 1662–1666).

Inflammatory Diseases

Studies on fibroblasts from the GSK-3β knockout mouse indicate that inhibition of GSK-3 may be useful in treating inflammatory disorders or diseases through the negative regulation of NFkB activity (Hoeflich K. P., et al., *Nature*, 2000, 406, 86–90).

Dermatological Disorders

The finding that transient β-catenin stabilization may play a role in hair development (Gat, et al., *Cell*, 1998, 95, 605–614) suggests that GSK-3 inhibitors could also be used in the treatment of baldness.

Central Nervous System Disorders

In addition to modulation of glycogen synthase activity, GSK-3 also plays an important role in the CNS disorders. GSK-3 inhibitors may be of value as neuroprotectants in the treatment of acute stroke and other neurotraumatic injuries (Pap and Cooper, *J. Biol. Chem.*, 1998, 273, 19929–19932). Lithium, a low mM inhibitor of GSK-3, has been shown to protect cerebellar granule neurons from death (D'Mello, et al., *Exp. Cell Res.*, 1994, 211, 332–338) and chronic lithium treatment has demonstrable efficacy in the middle cerebral artery occlusion model of stroke in rodents (Nonaka and Chuang, *Neuroreport*, 1998, 9(9), 2081–2084).

Tau and β-catenin, two known in vivo substrates of GSK-3, are of direct relevance in consideration of further aspects of the value of GSK-3 inhibitors in relation to treatment of chronic neurodegenerative conditions. Tau hyperphosphorylation is an early event in neurodegenerative conditions such as Alzheimer's disease and is postulated to promote microtubule disassembly. Lithium has been reported to reduce the phosphorylation of tau, enhance the binding of tau to microtubules and promote microtubule assembly through direct and reversible inhibition of GSK-3 (Hong M. et al *J. Biol. Chem.*, 1997, 272(40), 25326–32). β-catenin is phosphorylated by GSK-3 as part of a tripartite axin protein complex resulting in β-catenin degradation (Ikeda, et al., *EMBO J.*, 1998, 17, 1371–1384). Inhibition of GSK-3 activity is involved in the stabilization of catenin and promotes β-catenin-LEF-1/TCF transcriptional activity (Eastman, Grosschedl, *Curr. Opin. Cell Biol.*, 1999, 11, 233). Studies have also suggested that GSK-3 inhibitors may also be of value in the treatment of schizophrenia (Cotter D., et al. *Neuroreport*, 1998, 9, 1379–1383; Lijam N., et al., *Cell*, 1997, 90, 895–905) and manic depression (Manji, et al., *J. Clin. Psychiatry*, 1999, 60, (Suppl 2)27–39 for review).

Accordingly, compounds found useful as GSK-3 inhibitors could have further therapeutic utility in the treatment of diabetes, inflammatory diseases, dermatological disorders and central nervous system disorders.

A preferred method of the present invention is a method for treating or ameliorating a kinase or dual-kinase mediated disorder in a subject in need thereof comprising administering to the subject a therapeutically effective amount of an instant compound or pharmaceutical composition thereof. The therapeutically effective amount of the compounds of Formula (I) exemplified in such a method is from about 0.001 mg/kg/day to about 300 mg/kg/day.

Embodiments of the present invention include the use of a compound of Formula (I) for the preparation of a medicament for treating or ameliorating a kinase or dual-kinase mediated disorder in a subject in need thereof wherein a preferred method step comprises administering the kinase to dual-kinase inhibitor to a patient.

In accordance with the methods of the present invention, an individual compound of the present invention or a pharmaceutical composition thereof can be administered separately at different times during the course of therapy or concurrently in divided or single combination forms. The instant invention is therefore to be understood as embracing all such regimes of simultaneous or alternating treatment and the term "administering" is to be interpreted accordingly.

Embodiments of the present method include a compound or pharmaceutical composition thereof advantageously co-administered in combination with other agents for treating, reducing or ameliorating the effects of a kinase or dual-kinase mediated disorder. For example, in the treatment of diabetes, especially Type II diabetes, a compound of Formula (I) or pharmaceutical composition thereof may be used in combination with other agents, especially insulin or antidiabetic agents including, but not limited to, insulin secretagogues (such as sulphonylureas), insulin sensitizers including, but not limited to, glitazone insulin sensitizers (such as thiazolidinediones) or biguamides or a glucosidase inhibitors.

The combination product is a product that comprises the co-administration of a compound of Formula (I) or a pharmaceutical composition thereof and an additional agent for treating or ameliorating a kinase or dual-kinase mediated disorder, and the term combination product further comprises a product that is sequentially administered where the product comprises a compound of Formula (I) or pharmaceutical composition thereof and an additional agent for treating or ameliorating a kinase or dual-kinase mediated disorder, administration of a pharmaceutical composition containing a compound of Formula (I) or pharmaceutical composition thereof and an additional agent for treating or ameliorating a kinase or dual-kinase mediated disorder or the essentially simultaneous administration of a separate pharmaceutical composition containing a compound of Formula (I) or pharmaceutical composition thereof and a separate pharmaceutical composition containing an additional agent for treating or ameliorating a kinase or dual-kinase mediated disorder.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The ubiquitous nature of the PKC and GSK isoforms and their important roles in physiology provide incentive to produce highly selective PKC and GSK inhibitors. Given the evidence demonstrating linkage of certain isoforms to disease states, it is reasonable to assume that inhibitory compounds that are selective to one or two PKC isoforms or to a GSK isoform relative to the other PKC and GSK isoforms and other protein kinases are superior therapeutic agents. Such compounds should demonstrate greater efficacy and lower toxicity by virtue of their specificity. Accordingly, it will be appreciated by one skilled in the art that a particular compound of Formula (I) is selected where it is therapeutically effective for a particular kinase or dual-kinase mediated disorder based on the modulation of the disorder through the demonstration of selective kinase or dual-kinase inhibition in response to that compound. Experiments exemplifying selective kinase or dual-kinase inhibition are provided in the examples. The usefulness of a compound of Formula (I) as a selective kinase or dual-kinase inhibitor can be determined according to the methods disclosed herein and based on the data obtained to date, it is anticipated that a particular compound will be useful in inhibiting one or more kinase or dual-kinase mediated disorders and therefore is uesfull in one or more kinase or dual-kinase mediated disorders.

Therefore, the term "kinase or dual-kinase mediated disorders" as used herein, includes, and is not limited to, cardiovascular diseases, diabetes, diabetes-associated disorders, inflammatory diseases, immunological disorders, dermatological disorders, oncological disorders and CNS disorders.

Cardiovascular diseases include, and are not limited to, acute stroke, heart failure, cardiovascular ischemia, thrombosis, atherosclerosis, hypertension, restenosis, retinopathy of prematurity or age-related macular degeneration.

Diabetes includes insulin dependent diabetes or Type II non-insulin dependent diabetes mellitus. Diabetes-associated disorders include, and are not limited to, impaired glucose tolerance, diabetic retinopathy, proliferative retinopathy, retinal vein occlusion, macular edema, cardiomyopathy, nephropathy or neuropathy. Inflammatory diseases include, and are not limited to, vascular permeability, inflammation, asthma, rheumatoid arthritis or osteoarthritis. Immunological disorders include, and are not limited to, transplant tissue rejection, HIV-1 or immunological disorders treated or ameliorated by PKC modulation. Dermatological disorders include, and are not limited to, psoriasis, hair loss or baldness. Oncological disorders include, and are not limited to, cancer or tumor growth (such as breast, brain, kidney, bladder, ovarian or colon cancer or leukemia) and other diseases associated with uncontrolled cell proliferation such as recurring benign tumors as well as including proliferative angiopathy and angiogenesis; and, includes use for compounds of Formula (I) as an adjunct to chemotherapy and radiation therapy. CNS disorders include, and are not limited to, chronic pain, neuropathic pain, epilepsy, chronic neurodegenerative conditions (such as dementia or Alzheimer's disease), mood disorders (such as schizophrenia), manic depression or neurotraumatic, cognitive decline and ischemia-related diseases (as a result of head trauma (from acute ischemic stroke, injury or surgery) or transient ischemic stroke (from coronary bypass surgery or other transient ischemic conditions)).

Pharmaceutical compositions contemplated within this invention can be prepared according to conventional pharmaceutical techniques. A pharmaceutically acceptable carrier may be used in the composition of the invention. The composition may take a wide variety of forms depending on the form of preparation desired for administration including, but not limited to, intravenous (both bolus and infusion), oral, nasal, transdermal, topical with or without occlusion, intraperitoneal, subcutaneous, intramuscular or parenteral, all using forms well known to those of ordinary skill in the pharmaceutical arts. In preparing the compositions in oral dosage form, one or more of the usual pharmaceutical carriers may be employed, such as water, glycols, oils, alcohols, flavoring agents, preservatives, coloring agents, syrup and the like in the case of oral liquid preparations (for example, suspensions, elixirs and solutions), or carriers such as starches, sugars, diluents, granulating agents, lubricants, binders, disintegrating agents and the like in the case of oral solid preparations (for example, powders, capsules and tablets).

As is also known in the art, the compounds may alternatively be administered parenterally via injection of a formulation consisting of the active ingredient dissolved in an inert liquid carrier. The injectable formulation can include the active ingredient mixed with an appropriate inert liquid carrier. Acceptable liquid carriers include vegetable oils such as peanut oil, cotton seed oil, sesame oil, and the like, as well as organic solvents such as solketal, glycerol, formal, and the like. As an alternative, aqueous parenteral formulations may also be used. For example, acceptable aqueous solvents include water, Ringer's solution and an isotonic aqueous saline solution. Further, a sterile non-volatile oil can usually be employed as solvent or suspending agent in the aqueous formulation. The formulations are prepared by dissolving or suspending the active ingredient in the liquid carrier such that the final formulation contains from 0.005 to 10% by weight of the active ingredient. Other additives including a preservative, an isotonizer, a solubilizer, a stabilizer and a pain-soothing agent may adequately be employed.

Furthermore, compounds of the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

Because of their ease of administration, tablets and capsules represent an advantageous oral dosage unit form, wherein solid pharmaceutical carriers are employed. If desired, tablets may be sugar-coated or enteric-coated by standard techniques.

For liquid forms the active drug component can be combined in suitably flavored suspending or dispersing agents such as the synthetic and natural gums, including for example, tragacanth, acacia, methyl-cellulose and the like. Other dispersing agents that may be employed include glycerin and the like.

The compounds of the present invention can also be administered in the form of liposome delivery systems, such as small unilamellar vesicles, large unilamellar vesicles and multilamellar vesicles. Liposomes containing delivery systems as well known in the art are formed from a variety of phospholipids, such as cholesterol, stearylamine or phosphatidylcholines.

The instant pharmaceutical composition will generally contain a per dosage unit (e.g., tablet, capsule, powder, injection, teaspoonful and the like) from about 0.001 to about 100 mg/kg. In one embodiment, the instant pharmaceutical composition contains a per dosage unit of from about 0.01 to about 50 mg/kg of compound, and preferably from about 0.05 to about 20 mg/kg. Methods are known in the art for determining therapeutically effective doses for the instant pharmaceutical composition. The therapeutically effective amount for administering the pharmaceutical composition to a human, for example, can be determined mathematically from the results of animal studies.

| Abbreviations | |
|---|---|
| "Ph" or "PH" | Phenyl |
| "Boc" | t-Butoxycarbonyl |
| "PdCl$_2$(PPh$_3$)$_2$" | Dichlorobis(triphenylphosphine)palladium(II) |
| "TFA" | Trifluoroacetic acid |
| "DIEA" | N,N-diisopropylethylamine |
| "HMDS" | Hexamethyldisilazane |
| "Cpd" | Compound |
| "THF" | Tetrahydrofuran |
| "DMF" | N,N-Dimethylformamide |
| "TMSCHN$_2$" | trimethylsilyldiazomethane |
| "DMC" | dichloromethane |
| "DCC" | dicyclohexane carbodiimide |
| "HOBT" | hydroxybenzyl triazole |
| rt | room temperature |

A wavy line indicates bond attachment to a larger structure that is not shown but is otherwise identical to the larger compound of which the compound fragment is drawn.

Nomenclature

Compounds are named according to nomenclature well known in the art and such nomenclature is exemplified using ring numbering as follows:

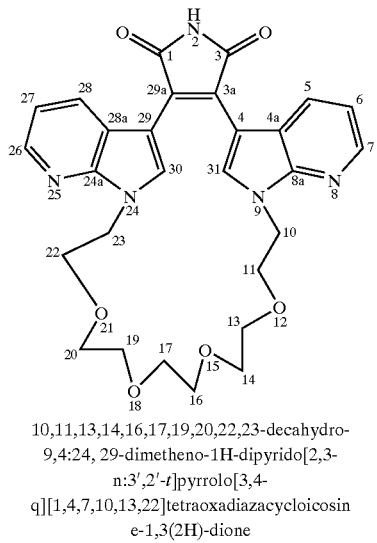

10,11,13,14,16,17,19,20,22,23-decahydro-
9,4:24, 29-dimetheno-1H-dipyrido[2,3-
n:3′,2′-t]pyrrolo[3,4-
q][1,4,7,10,13,22]tetraoxadiazacycloicosin
e-1,3(2H)-dione

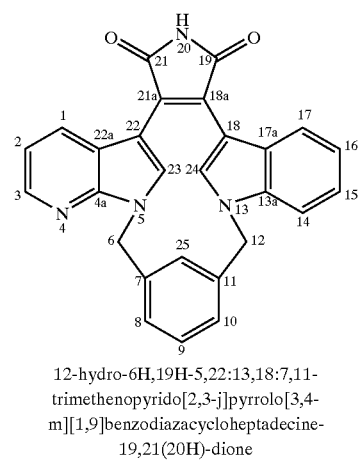

12-hydro-6H,19H-5,22:13,18:7,11-
trimethenopyrido[2,3-j]pyrrolo[3,4-
m][1,9]benzodiazacycloheptadecine-
19,21(20H)-dione

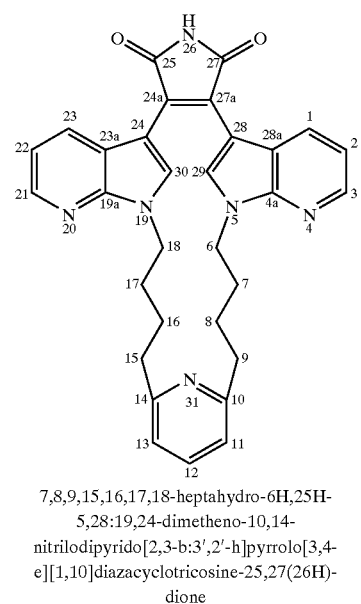

7,8,9,15,16,17,18-heptahydro-6H,25H-
5,28:19,24-dimetheno-10,14-
nitrilodipyrido[2,3-b:3′,2′-h]pyrrolo[3,4-
e][1,10]diazacyclotricosine-25,27(26H)-
dione

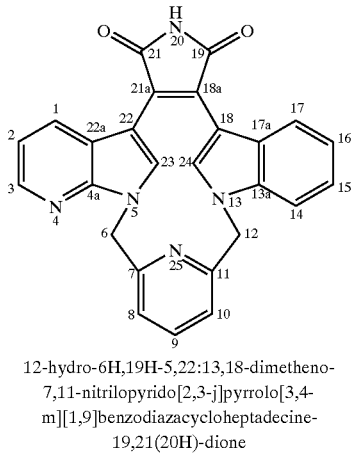

12-hydro-6H,19H-5,22:13,18-dimetheno-
7,11-nitrilopyrido[2,3-j]pyrrolo[3,4-
m][1,9]benzodiazacycloheptadecine-
19,21(20H)-dione Names can be generated using a nomenclature system based on these examples or may be generated using commercial chemical naming software such as the ACD/Index Name (Advanced Chemistry Development, Inc., Toronto, Ontario).

EXAMPLES

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Scheme A

Preparation of Bis(1H-Pyrazolo[3,4-B]Pyridine)Maleimide Compounds of Formula (Ic) and Bis(1H-Pyrrolo[2,3-B] Pyridine)Maleimide Compounds of Formula (Ia)

Compound A1 (wherein A is selected from nitrogen and E is selected from carbon for compounds of Formula (Ia) and A and E are selected from nitrogen for compounds of Formula (Ic)) was dissolved in a suitable solvent and then cooled. Trimethyltin chloride was added under an inert atmosphere to react with Compound A1 (below) and then BuLi was added. The reaction was washed with an aqueous solvent and the product Compound A2 was purified. Compound A2 was reacted with a 2,3-dichloromaleimide Compound A3 in the presence of $PdCl_2(PPh_3)_2$ and LiCl in a suitable solvent. The product Compound A4 may then be purified by column chromatography.

Scheme B

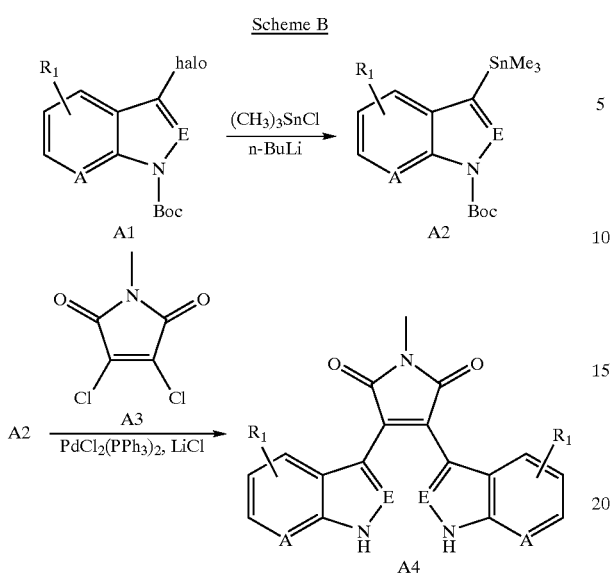

Preparation of Indolyl-(Pyrrolo[2,3-B]Pyridine)Maleimide Compounds of Formula (Ig) and Indolyl-(1H-Pyrazolo[3,4-B]Pyridine)Maleimide Compounds of Formula (Ih)

Chloro-indoylmaleimide Compound A2 (wherein A is selected from nitrogen and E is selected from carbon for compounds of Formula (Ig) and A and E are selected from nitrogen for compounds of Formula (Ih)) and Compound B1 were diluted in a suitable solvent and reacted in the presence of LiCl and dichlorobis(triphenylphosphine)palladium(II) in an inert atmosphere. The Compound A2 protecting group was removed from an intermediate of Compound B1 by reaction with TFA in a suitable solvent to yield the product Compound B2.

Scheme C

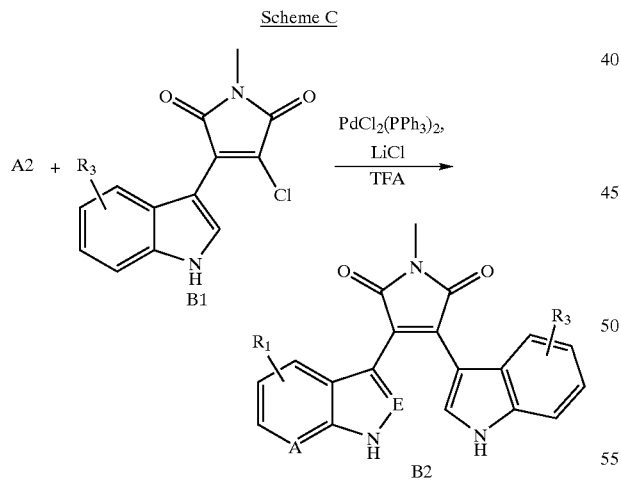

Preparation of Polyalkoxy Macrocycles

A hydroxy polyalkoxy chain Compound C1 may be reacted with TsCl or MsCl to produce a polyalkoxy chain Compound C2 or Compound C3, respectively (prepared as described in Bender, S. L. and Gauthier, D. R., Tetrahedron Lett., 1996, 37(1), 13–16).

The Compound A4 (wherein A and E are independently selected from the group consisting of a carbon atom and a nitrogen atom) was dissolved in a suitable solvent with $Cs_2CO_3$ at an elevated temperature. The polyalkoxy chain Compound C2 or Compound C3 was dissolved in a suitable solvent and was added slowly to the reaction mixture. The reaction was then extracted and purified to yield the product Compound C4.

Using equivalent methods, $T_fO(CF_3SO_3)$ or $T_sO$ (toluleneSO$_3$) may be coupled to the Compound C4 ring nitrogen. The Compound C4 was dissolved in an alcohol, then a base and heated to reflux. The reaction was acidified to form a precipitated Compound C5. Compound C5 was dissolved in a suitable solvent containing HMDS and heated for a time and at a temperature sufficient to produce Compound C6. The product Compound C6 may then be purified by column chromatography.

Scheme D

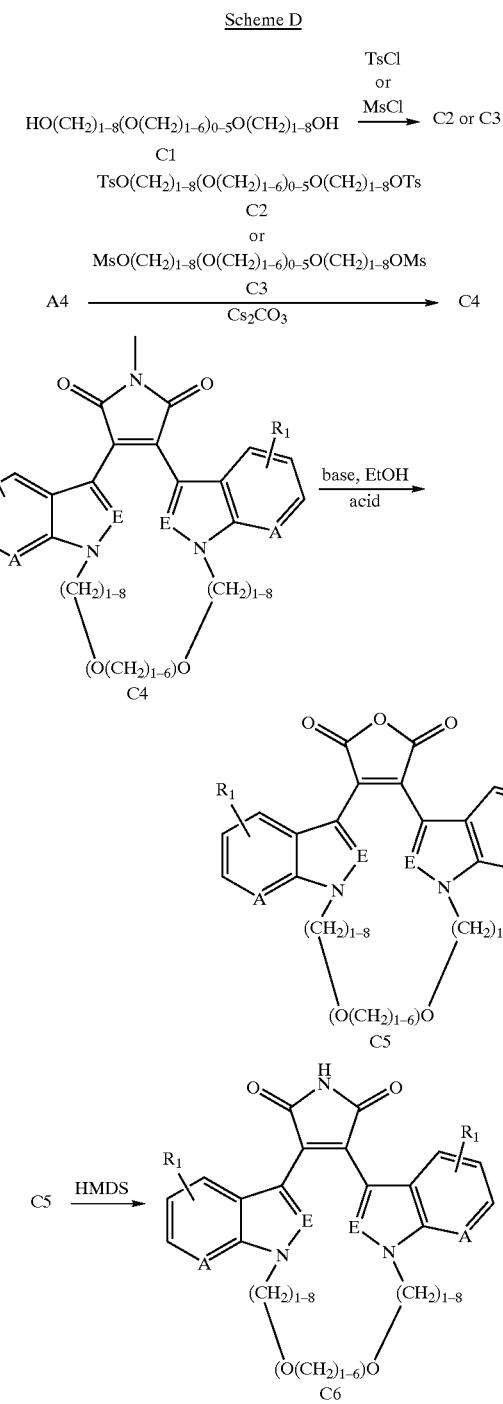

Preparation of Alkyl-(Heteroaryl/Aryl)-Alkyl Macrocycles

The Compound A4 (wherein A and E are independently selected from the group consisting of a carbon atom and a nitrogen atom) was diluted in a suitable solvent containing $Cs_2CO_3$ and reacted at an elevated temperature with Compound D1 (dibromo$(CH_2)_{1-4}$alkyl; wherein X is a carbon or a nitrogen atom). Those skilled in the art of organic synthesis will appreciate that the term "elevated temperature" is used herein to refer to temperatures that are preferably greater than 22° C. and preferably below the reflux temperature. It is understood that those in the art will be able to vary the time and temperature of these reactions to optimize product production. The product was extracted and purified to yield Compound D2. The product Compound D2 was dissolved in an alcohol and base and was heated to reflux. Then the reaction was acidified to form a precipitated intermediate which was dissolved in a suitable solvent containing HMDS and was heated. The product Compound D3 was purified by column chromatography.

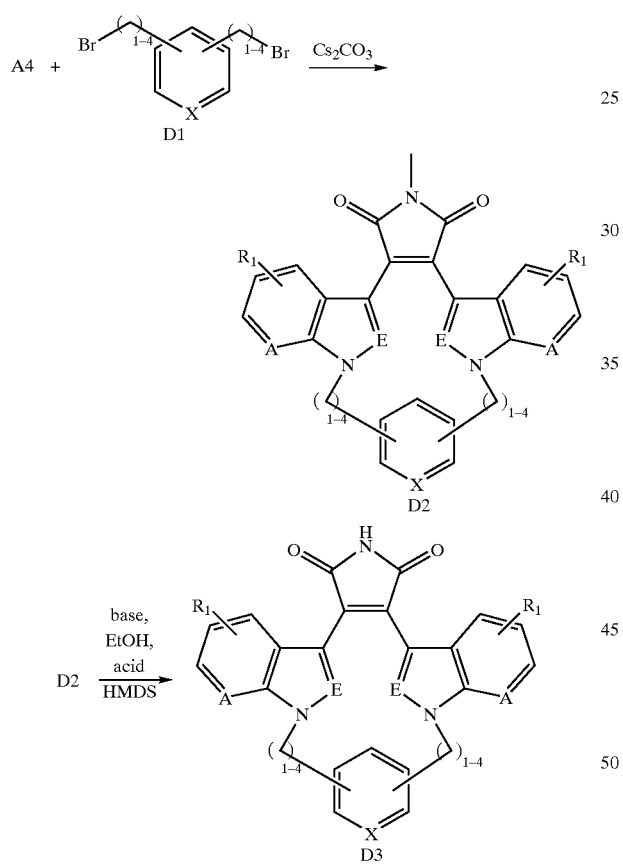

Multiheteroatom Symmetrical Macrocycles

The Compound A4 (wherein A and E are independently selected from the group consisting of a carbon atom and a nitrogen atom) was diluted in a suitable solvent containing $Cs_2CO_3$ and reacted at elevated temperature with a Compound E1 (wherein a is $(CH_2)_{1-6}$alkyl). The product was extracted and purified to yield a Compound E2. The Compound E2 was reacted with $R_6NH_2$ in the presence of DIEA (N,N-diisopropylethylamine) in THF at an elevated temperature, then cooled and evaporated to give a Compound E3. The Compound E3 was dissolved in an alcohol and base and heated to reflux. The reaction was then acidified and evaporated. The resulting solid was treated with ammonium acetate at elevated temperatures, cooled, and extracted to provide Compound E4.

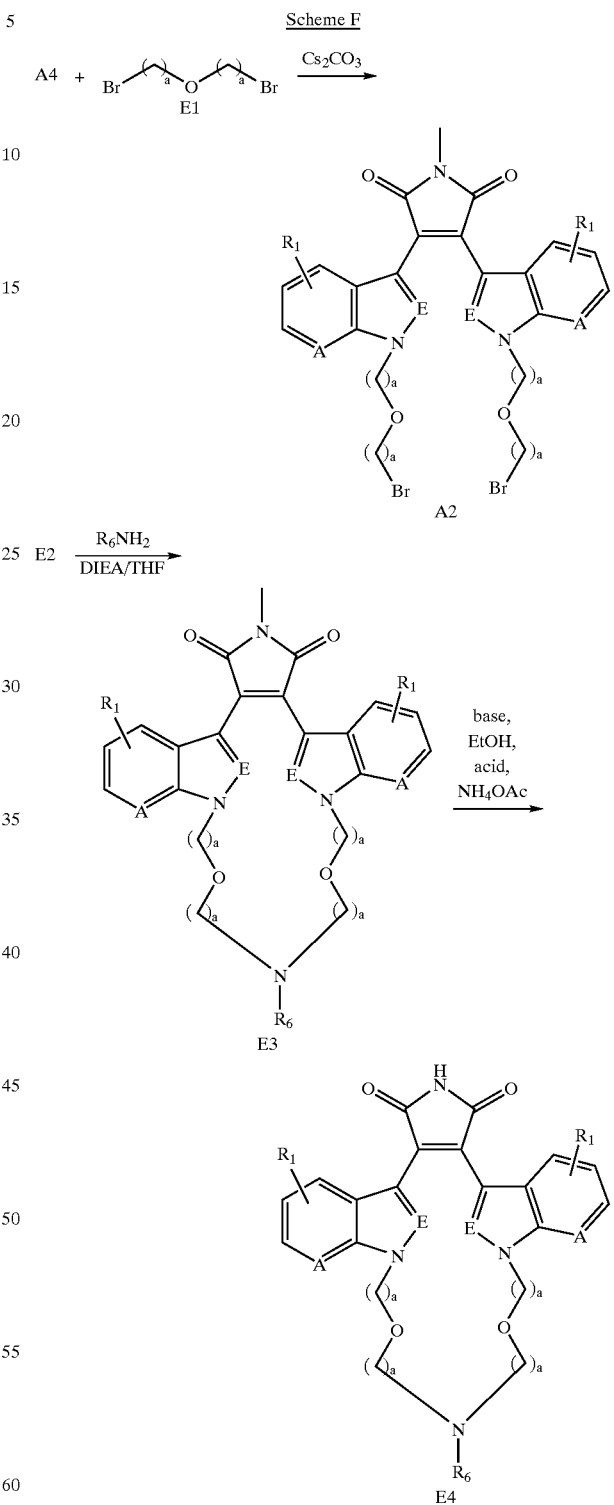

Symmetrical Polyalkylamine Macrocycles

The Compound A4 (wherein A and E are independently selected from the group consisting of a carbon atom and a nitrogen atom) was diluted in a suitable solvent containing $Cs_2CO_3$ and reacted at elevated temperature with a Compound F1 (dihalo(CH$_2$)$_{1-6}$alkyl). The product was extracted and purified to yield a Compound F2. The Compound F2 was reacted with a Compound F3 NHR$_6$(CH$_2$)$_{1-6}$NR$_7$(CH$_2$)$_{1-6}$NHR$_8$ in the presence of DIEA (N,N-diisopropylethylamine) and KI in THF at an elevated temperature. The product was cooled and evaporated to give a Compound F4. The Compound F4 was dissolved in an alcohol and base and heated to reflux. The reaction was then acidified and evaporated. The resulting solid was treated with ammonium acetate at elevated temperatures, cooled and extracted to form Compound F5

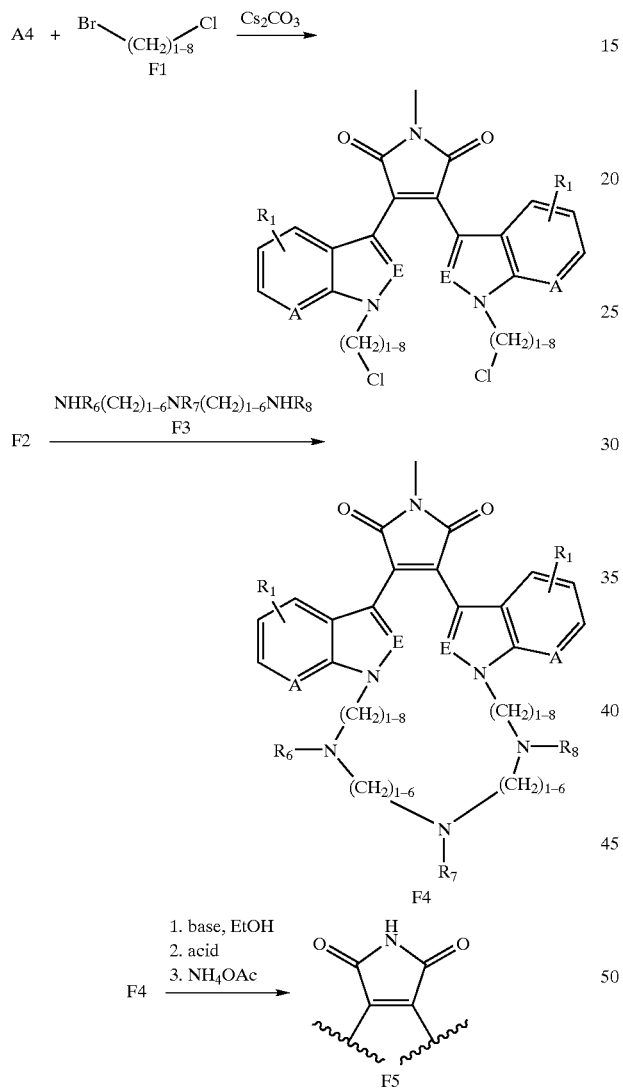

Alternatively, the Compound F2 was reacted with a Compound F6 NHR$_6$(CH$_2$)$_{1-6}$NHR$_7$ or Compound F8 NHR$_6$ to give a product Compound F7 having 2 nitrogen atoms within the macrocyclic ring or a product Compound F9 having 1 nitrogen atom within the macrocyclic ring. Following the procedures previously disclosed, the unsubstituted imide Compound F10 and Compound F11 may be obtained from Compound F7 and Compound F9, respectively.

Scheme G

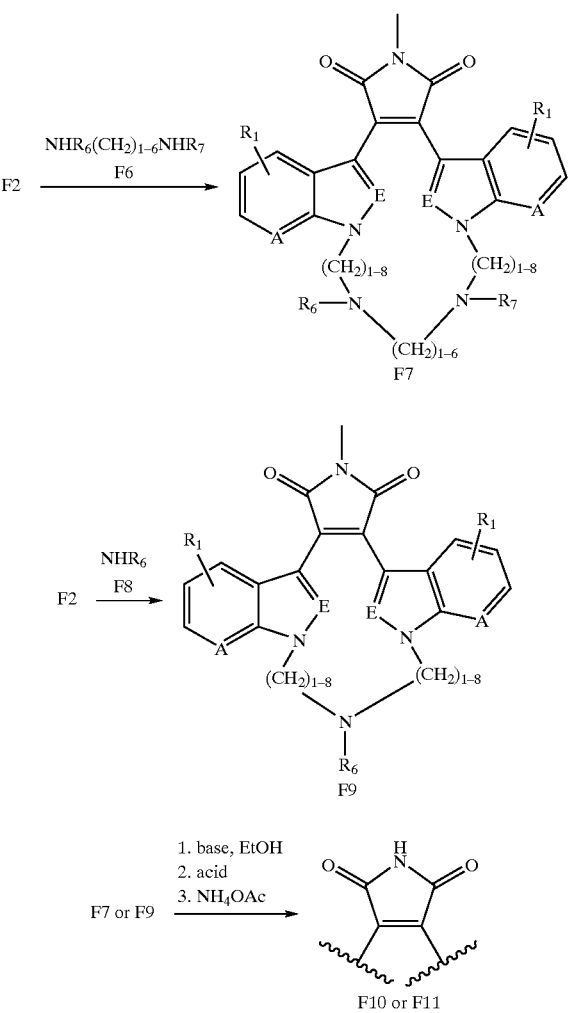

Asymmetrical Macrocycles

A mixture of Compound G1 (wherein A and E are independently selected from the group consisting of a carbon atom and a nitrogen atom) and Compound G2 (wherein b and c are independently selected from (CH$_2$)$_{0-5}$alkyl) were dissolved in a suitable solvent and then reacted at an elevated temperature in the presence of cesium carbonate. The reaction was filtered, evaporated and the residue was purified to give Compound G3. Compound G4 was dissolved in an appropriate solvent under an inert atmosphere and HOBT and DCC were added. The reaction was stirred and ammonium hydroxide was slowly added and the reaction was stirred again. The reaction was filtered and the filtrate was collected and extracted with an aqueous solvent. Sodium chloride was added to the aqueous solution and the aqueous solution was extracted with ethyl acetate. The ethyl acetate extract was dried and evaporated to provide a solid. The solid product was triturated with diethyl ether and filtered to yield a Compound G5. A Compound G6 was added to Compound G5 with cesium carbonate and the mixture was dissolved in a suitable solvent and stirred at an elevated temperature. The reaction was filtered, the filtrate was evaporated and the residue purified to give Compound G7.

The ester Compound G3 and amide Compound G7 were dissolved in a suitable solvent under an inert atmosphere and were cooled. Then 1.0 M potassium t-butoxide in THF was slowly added to the reaction mixture. The resulting mixture was stirred under cool conditions, allowed to warm and then stirred again. Then concentrated HCl was added and the reaction was stirred again. The mixture was partitioned between EtOAc and H₂O. Two layers were separated and the aqueous layer was extracted with EtOAc. The combined extracts were washed with water, saturated aq. NaHCO₃ and brine, then dried and evaporated to give a Compound G8. The Compound G8 was dissolved in a solvent containing pyridine and then Ms₂O was added. The reaction was stirred at elevated temperatures and then the mixture was cooled to ambient temperature. Solvent and acid were added and the mixture was stirred and then extracted. The organic phase was washed with acid, water and brine and then was dried and evaporated to yield Compound G9. A solution of Compound G9, DIEA (N,N-diisopropylethylamine) and Compound G10 $R_6NH_2$ was stirred at elevated temperature. The volatiles were removed under vacuo and the residue was purified to give the target product Compound G11.

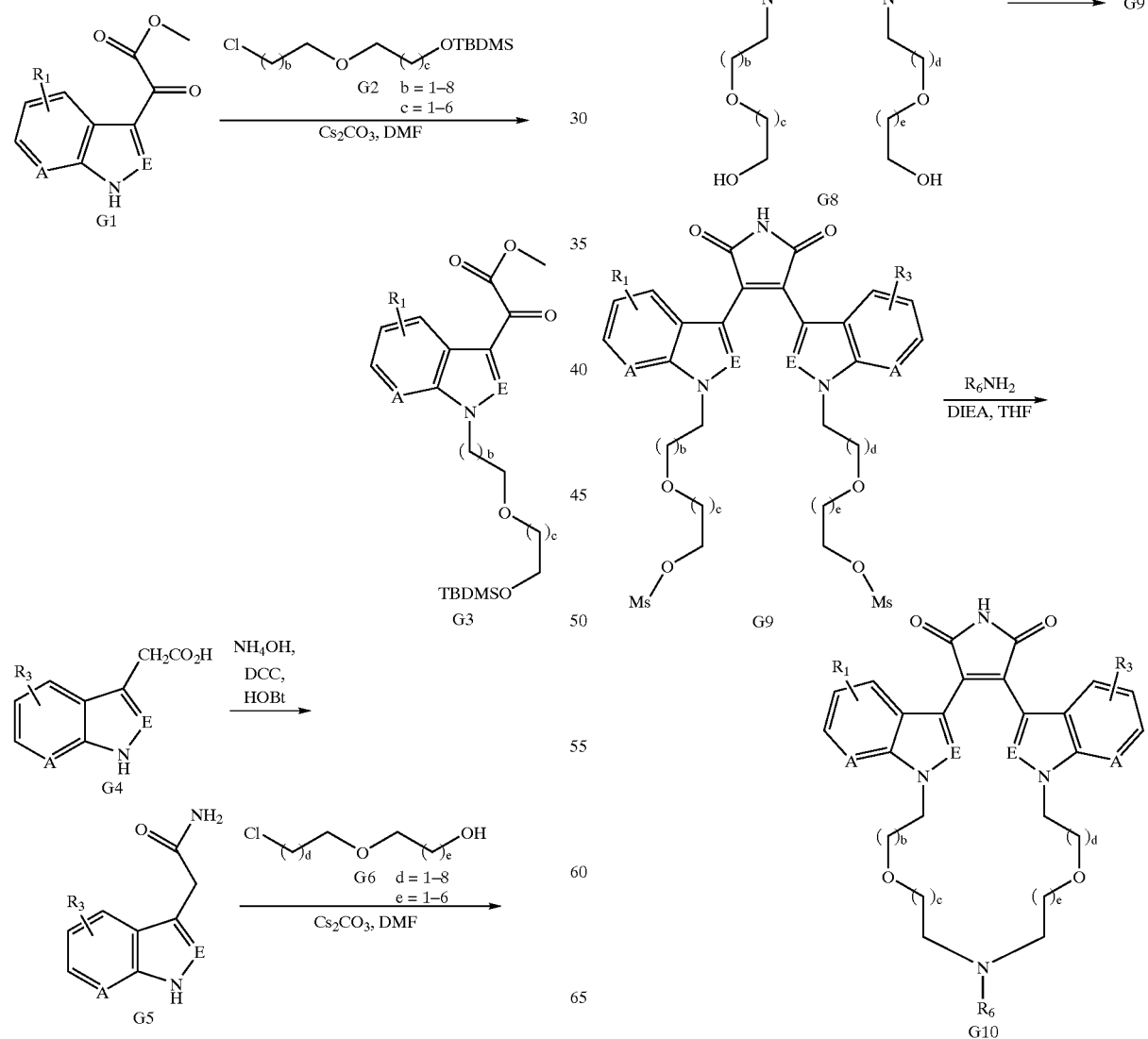

Specific Synthetic Examples

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

$^1$H NMR spectra were measured on a Bruker AC-300 (300 MHz) spectrometer using tetramethylsilane as an internal standard. Elemental analyses were obtained by Quantitative Technologies Inc. (Whitehouse, N.J.), and the results were within 0.4% of the calculated values unless otherwise mentioned. Melting points were determined in open capillary tubes with a Thomas-Hoover apparatus and were uncorrected. The optical rotations were measured at 25° C. with an Autopol III polarimeter. Electrospray mass spectra (MS-ES) were recorded on a Hewlett Packard 59987A spectrometer. High resolution mass spectra (HRMS) were obtained on a Micromass Autospec. E. spectrometer.

Example 1

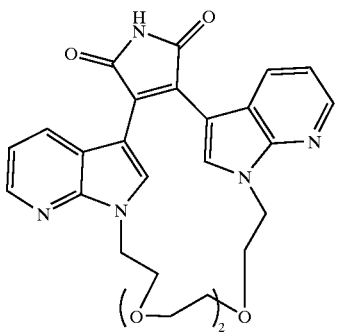

Compound 1

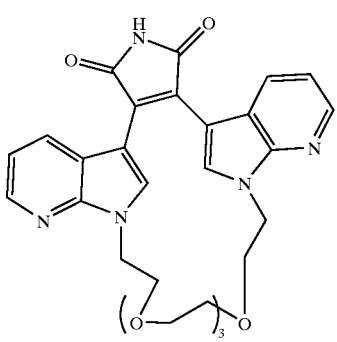

Compound 2

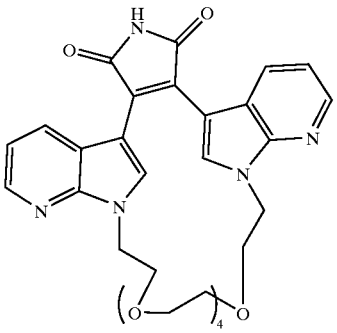

Compound 3

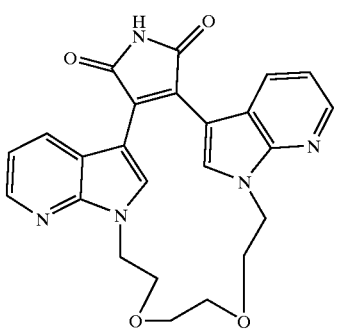

Compound 28

6,7,9,10,12,13,15,16-octahydro-23H-5,26:17,22-dimetheno-5H-dipyrido[2,3-k:3',2'-q]pyrrolo[3,4-n][1,4,7,10,19]trioxadiazacyclohenicosine-23,25(24H)-dione(Compound 1);

10,11,13,14,16,17,19,20,22,23-decahydro-9,4:24,29-dimetheno-1H-dipyrido[2,3-n:3',2'-t]pyrrolo[3,4-q][1,4,7,10,13,22] tetraoxadiazacyclotetracosine-1,3(2H)-dione (Compound 2);

10,11,13,14,16,17,19,20,22,23,25,26-dodecahydro-9,4:27,32-dimetheno-1H-dipyrido[2,3-q:3',2'-w]pyrrolo[3,4-t][1,4,7,10,13,16,25] pentaoxadiazacycloheptacosine-1,3(2H)-dione(Compound 3);

6,7,9,10,12,13-hexahydro-20H-5,23:14,19-dimetheno-5H-dipyrido[2,3-h:3',2'-n] pyrrolo[3,4-k][1,4,7,16]dioxadiazacyclooctadecine-20,22(21H)-dione(Compound 28)

Trimethyl tin chloride (26.5 mL, 1 M in THF, 26.5 mmol) was added to a THF solution (15 mL) of 7-aza-1-(tert-butyloxycarbonyl)-3-iodoindole Compound 1a (1.82 g, 5.3 mmol, Kelly, T. A., *J. Med Chem.* 1997, 40, 2430) at −78° C. under nitrogen. After 10 min, n-BuLi (10 mL, 1.6 M in hexane, 16 mmol) was added dropwise at −78° C. and the reaction was allowed to warm up to 20° C. overnight. Water (4 mL) was added and the solvent was removed under vacuum. The residue was diluted with hexane (250 mL) and the organic layer was washed with water, dried (Na$_2$SO$_4$) and concentrated. The product was purified by column chromatography (SiO$_2$) to give 1.198 g (60%) of organostannane Compound 1b as an oil. $^1$H NMR (300 MHz, CDCl$_3$) δ 8.45 (d, J=4.9 Hz, 1H), 7.77 (d, J=7.6 Hz, 1H), 7.48 (s, 1H), 7.13 (dd, J=7.7, 4.8 Hz, 1H), 1.65 (s, 9H), 0.36 (m, 9H); MS (ES) m/z 405 (M+Na).

A mixture of Compound 1b (185 mg, 0.486 mmol), 2,3-dichloromaleimide Compound 1c (29 mg, 0.162 mmol, prepared as described in *J. Org. Chem*, 1998, 63, 1961), PdCl$_2$(PPh$_3$)$_2$ (5.4 mg, 0.0077 mmol) and LiCl (32 mg, 0.77 mmol) in anhydrous toluene (2 mL) was stirred at 95° C. overnight. The solvent was removed under vacuum. The product was purified by column chromatography (SiO$_2$) to give 23 mg of Compound 1d as an orange-red solid: $^1$H NMR (300 MHz, DMSO-$d_6$) δ 12.35 (s, 2H), 8.12 (brd, J=3.9 Hz, 2H), 7.92 (s, 2H), 7.08 (d, J=7.7 Hz, 2H), 6.73 (m, 2H), 3.06 (s, 3H); MS (ES) m/z 344 (M+H$^+$).

Preparation of Cpd 1

Tetraethylenebismesylate Compound 1f (0.252 g, 0.72 mmol) in DMF (5.4 mL) was added via syringe pump for 3 h to a suspension of $Cs_2CO_3$ (0.51 g 1.56 mmol) and starting material Compound 1d (0.162 g, 0.48 mmol) in DMF (24 mL) at 100° C. After addition was completed the reaction mixture was cooled to 20° C. and stirred for 3 h. The reaction mixture was diluted with $NH_4Cl_{(aq)}$ and the product was extracted into $CH_2Cl_2$. The organic layer was washed with water, dried ($Na_2SO_4$) and concentrated. Product was purified by column chromatography ($CH_2Cl_2$/Acetone) to give 0.075 g (31%) of Compound 1i as a reddish orange solid; $^1$H NMR (300 MHz, CDCl$_3$) δ 8.32 (m, 2H), 7.80 (s, 2H), 7.61 (d, J=7.1 Hz, 2H), 6.99 (m, 2H), 4.50 (t, J=4.5 Hz, 4H), 3.71 (t, J=4.5 Hz, 4H), 3.22 (m, 11H); MS (ES) m/z 502 (M+H$^+$).

A mixture of Compound 1i (0.083 g, 0.16 mmol) in EtOH (1 mL) and 10 N KOH (1.6 mmol) was heated to a gentle reflux at 78° C. overnight. The reaction mixture was cooled to 0° C. and acidified with 1 N HCl. $CH_2Cl_2$ was added and the organic layer was separated and washed with water, dried ($Na_2SO_4$) and concentrated to provide the product Compound 1m (0.074 g, 81%) as a red solid which was used directly. A MeOH solution (0.05 mL) containing HMDS (0.24 g, 1.5 mmol) was added to a solution of Compound 1m (0.074 g, 0.15 mmol) in DMF (1.0 mL). The reaction was heated at 80° C. for 6 h. Upon completion the reaction was cooled and the solvent was evaporated under vacuum. The product was purified by column chromatography ($CH_2Cl_2$/Acetone) to give 0.067 g (91%) of Compound 1 as an orange solid; $^1$H NMR (300 MHz, CDCl$_3$) δ 8.32 (d, J=4.3 Hz, 2H), 7.81 (s, 2H), 7.60 (d, J=7.8 Hz, 2H), 7.49 (s, 1H), 7.00 (m, 2H), 4.50 (t, J=4.5 Hz, 4H), 3.71 (t, J=4.5 Hz, 4H), 3.23 (m, 8H); MS (ES) m/z 488 (M+H$^+$).

Preparation of Cpd 2

Pentaethylenebismesylate Compound 1 g (0.3 g, 0.76 mmol) in DMF (6 mL) was added via syringe pump for 4 h to a suspension of $Cs_2CO_3$ (0.41 g, 1.27 mmol) and starting material Compound 1d (0.2 g, 0.58 mmol) in DMF (18 mL) at 100° C. After addition was completed, the reaction mixture was cooled to 20° C. and stirred for 3 h. The reaction mixture was diluted with $NH_4Cl_{(aq)}$ after it was cooled to 0° C. in an ice bath. The product was extracted into $CH_2Cl_2$. The organic layer was washed with water, dried ($Na_2SO_4$) and concentrated. The product was purified by column chromatography ($CH_2Cl_2$/Acetone) to give 0.126 g (39%) of Compound 1j as an orange solid; $^1$H NMR (300 MHz, CDCl$_3$) δ 8.32 (m, 2H), 7.80 (s, 2H), 7.57 (dd, J=8.0, 1.5 Hz, 2H), 7.00 (m, 2H), 4.44 (t, J=4.6 Hz, 4H), 3.77 (t, J=4.6 Hz, 4H), 3.43 (m, 12H), 3.20 (s, 3H); MS (ES) m/z 546 (M+H$^+$).

A mixture of Compound 1j (0.094 g, 0.17 mmol) in EtOH (1 mL) and 10 N KOH (1.7 mmol) was heated to a gentle reflux at 78° C. overnight. The reaction mixture was cooled to 0° C. and acidified with 1 N HCl. $CH_2Cl_2$ was added and the organic layer was separated and washed with water, dried ($Na_2SO_4$) and concentrated. The product Compound 1n (0.075 g, 81%) was obtained as an orange solid and used directly. A MeOH solution (0.05 mL) containing HMDS (0.23 g, 1.4 mmol) was added to a solution of Compound 1n (0.075 g, 0.14 mmol) in DMF (1.0 mL). The reaction was heated at 80° C. for 5½ h. Upon completion the reaction was cooled and the solvent was evaporated under vacuum. Product was purified by column chromatography ($CH_2Cl_2$/Acetone) to give 0.038 g (51%) of Compound 2 as an orange solid. $^1$H NMR (300 MHz, CDCl$_3$) δ 8.32 (d, J=4.5 Hz, 2H), 7.83 (s, 2H), 7.66 (s, 1H), 7.57 (d, J=7.9 Hz, 2H), 6.99 (m, 2H), 4.45 (t, J=4.7 Hz, 4H), 3.77 (t, J=4.7 Hz, 4H), 3.45 (m, 12H); MS (ES) m/z 532 (M+H$^+$).

Preparation of Cpd 3

Hexaethylenebismesylate Compound 1 h (0.33 g, 0.76 mmol) in DMF (6 mL) was added via syringe pump for 3 h to a suspension of $Cs_2CO_3$ (0.41 g, 1.27 mmol) and starting material Compound 1d (0.2 g, 0.58 mmol) in DMF (18 mL) at 100° C. After addition was completed the reaction mixture was cooled to 20° C. and stirred for 3 h. The reaction mixture was diluted with $NH_4Cl_{(aq)}$ after it was cooled to 0° C. in ice bath. The product was extracted into $CH_2Cl_2$. The organic layer was washed with water, dried ($Na_2SO_4$) and concentrated. Product was purified by column chromatography ($CH_2Cl_2$/Acetone) to give 0.81 g (24%) of Compound 1k as an orange solid. $^1$H NMR (300 MHz, CDCl$_3$) δ 8.27 (m, 2H), 7.89 (s, 2H), 7.42 (dd, J=9.4, 1.4 Hz, 2H), 6.89 (m, 2H), 4.47 (t, J=4.8 Hz, 4H), 3.80 (t, J=4.8 Hz, 4H), 3.46 (s, 8H), 3.41 (s, 8H), 3.20 (s, 3H); MS (ES) m/z 590 (M+H$^+$).

A mixture of Compound 1k (0.073 g, 0.12 mmol) in EtOH (1 mL) and 10 N KOH (1.2 mmol) was heated to a gentle reflux at 78° C. overnight. The reaction mixture was cooled to 0° C. and acidified with 1 N HCl. $CH_2Cl_2$ was added and the organic layer was separated and washed with water, dried ($Na_2SO_4$) and concentrated. The product was purified by column chromatography ($CH_2Cl_2$/Acetone) to give Compound 1o (0.05 g, 70%) as an orange solid and used directly. A MeOH solution (0.05 mL) containing HMDS (0.14 g, 0.087 mmol) was added to a solution of Compound 1o (0.05 g, 0.087 mmol) in DMF (1.0 mL). The reaction was heated at 80° C. for 5 h. Upon completion the reaction was cooled and the solvent was evaporated under vacuum. Product was purified by column chromatography ($CH_2Cl_2$/Acetone) to give 0.044 g (88%) of Compound 3 as an orange solid; $^1$H NMR (300 MHz, CDCl$_3$) δ 8.29 (m, 2H), 7.90 (s, 2H), 7.80 (s, 1H), 7.42 (dd, J=8.0, 1.4 Hz, 2H), 6.90 (m, 2H), 4.48 (t, J=4.9 Hz, 4H), 3.81 (t, J=4.9 Hz, 4H), 3.47 (s, 8H), 3.43 (s, 8H); MS (ES) m/z 576 (M+H$^+$).

Preparation of Cpd 28

A solution of tri(ethylene glycol) (4.97 g, 33.1 mmol) in $CH_2Cl_2$ (40 mL) was cooled to −40° C. Triethylamine (13.8 mL, 99.3 mmol) was added, followed by a $CH_2Cl_2$ (15 mL) solution of MsCl (6.4 mL, 82.8 mmol). The mixture was stirred at 0° C. for 1 h, and poured into ice water (150 mL). The layers were separated and the aqueous phase was extracted with $CH_2Cl_2$ (3×15 mL). The organic layers were combined, washed sequentially with 5% HCl (15 mL), water (15 mL), 5% NaHCO$_3$ (15 mL) and water (15 mL), dried ($Na_2SO_4$) and concentrated under reduced pressure to give Compound 1e (as per the procedure described in *Liebigs Ann. Chem.*, 1994, 12, 1199–1209) (9.13 g, 90%) as yellow oil: $^1$H NMR (300 MHz, CDCl$_3$) δ 4.36–4.39 (m, 4H), 3.76–3.79 (m, 4H), 3.68 (s, 4H), 3.07 (s, 6H).

A mixture of Compound 1d (40 mg, 71% pure, 0.12 mmol), $Cs_2CO_3$ (115 mg, 0.35 mmol) and DMF (6 mL) was heated to 100° C. The triethylenebismesylate Compound 1e (54 mg, 0.18 mmol) in solution with DMF (1.5 mL) was added via syringe pump over 0.5 h. After the addition was complete, the mixture was stirred at 20° C. for 15 h, quenched with aqueous NH$_4$Cl (6 mL) and extracted with EtOAc (2×25 mL). The layers were separated and the organic phase was washed with water (15 m), then dried (Na$_2$SO$_4$) and concentrated. Purification with column chromatography on silica gel (eluting with CH$_2$Cl$_2$/acetone) gave Compound 11 (25 mg, 67%) as an orange solid: $^1$H NMR (300 MHz, CDCl$_3$) δ 8.35 (dd, J=4.7, 1.4 Hz, 2H), 8.11 (dd, J=8.0, 1.5 Hz, 2H), 7.63 (s, 2H), 7.12–7.16 (dd, J=8.0, 4.7 Hz, 2H), 4.42 (t, J=4.6 Hz, 4H), 3.77 (t, J=4.8 Hz, 4H), 3.45 (s, 4H), 3.20 (s, 3H); MS (ES) m/z 458 (M+H$^+$).

A mixture of Compound 11 (47 mg, 0.10 mmol), ethanol (2 mL) and 10 N KOH (0.1 mL) was heated to 80° C. for 15 h. After the solvent was removed, the residue was diluted with water (2 mL) and made acidic with 1N HCl to pH 2. The mixture was extracted with CH$_2$Cl$_2$ (4×15 mL) and the organic layers were combined, dried (Na$_2$SO$_4$) and concentrated to provide the product Compound 1p. Compound 1p was dissolved in DMF (1 mL) and a mixture of HMDS (1,1,1,3,3,3-hexamethyldisilazane) (0.25 mL, 1.0 mmol) and methanol (0.06 mL) was added. The mixture was heated to 80° C. for 5.5 h, then cooled to 20° C. and concentrated under reduced pressure. Purification by column chromatography on silica gel (eluting with CH$_2$Cl$_2$/acetone) gave Compound 28 (27 mg, 60%) as a red solid: $^1$H NMR (300 MHz, CDCl$_3$) δ 8.35 (dd, J=4.7, 1.5 Hz, 2H), 8.10 (dd, J=8.0, 1.5 Hz, 2H), 7.65 (s, 2H), 8.12–8.17 (dd, 8.0, 4.7 Hz, 2H), 4.41 (t, J=4.9 Hz, 4H), 3.77 (t, J=4.9 Hz, 4H), 3.44 (s, 4H); MS (ES) m/z 444 (M+H$^+$).

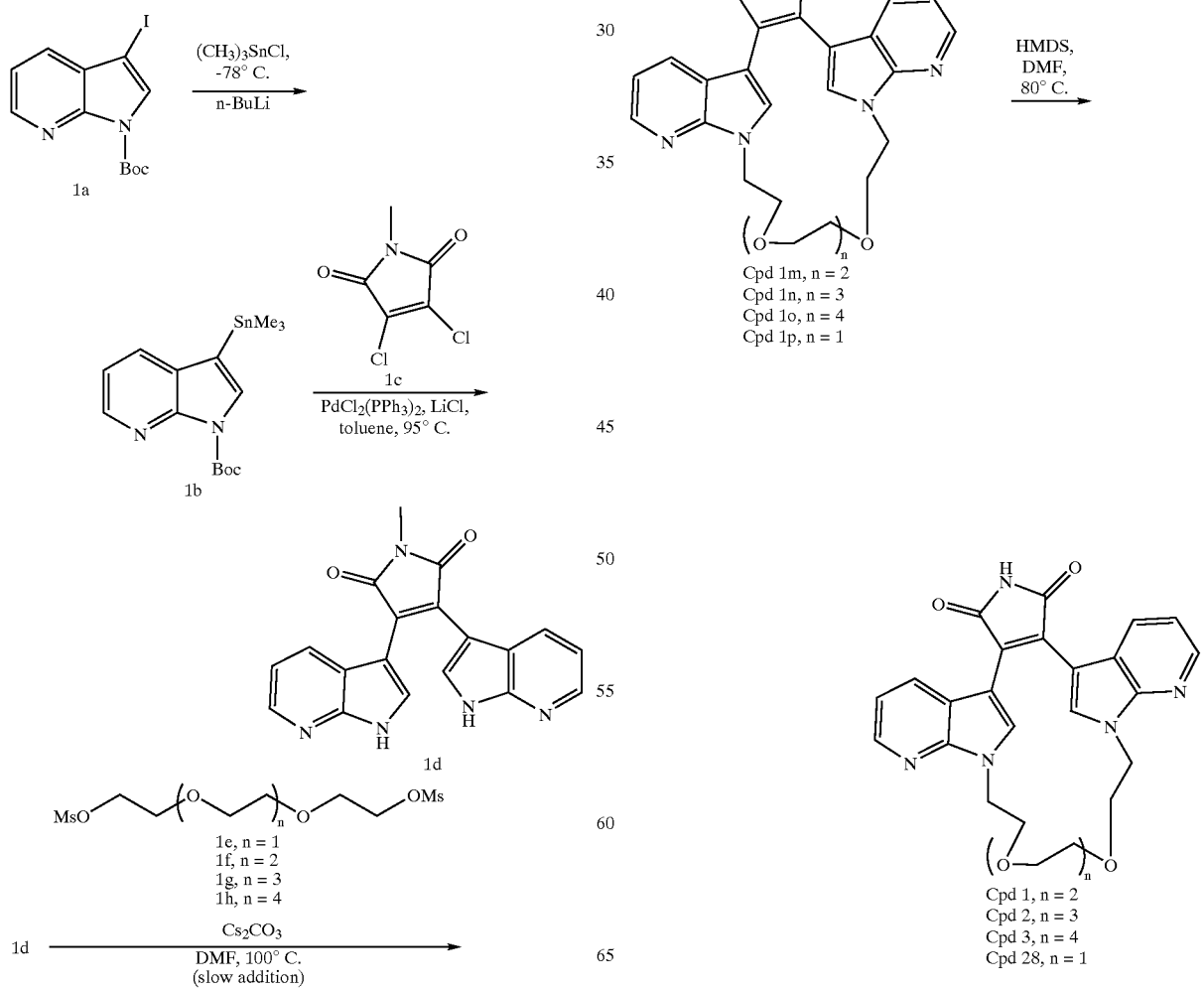

Example 2

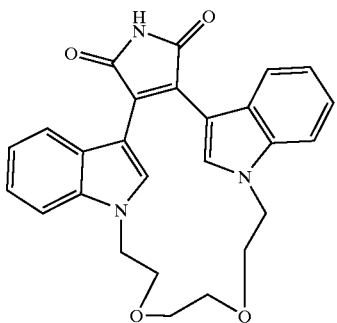
Compound 4

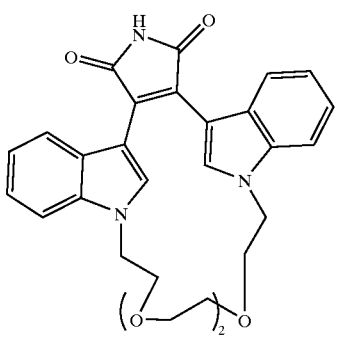
Compound 5

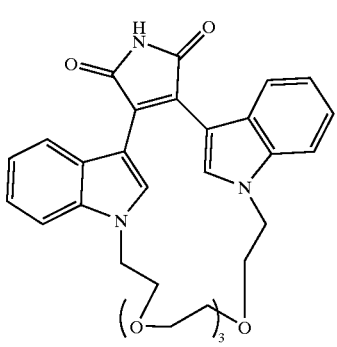
Compound 6

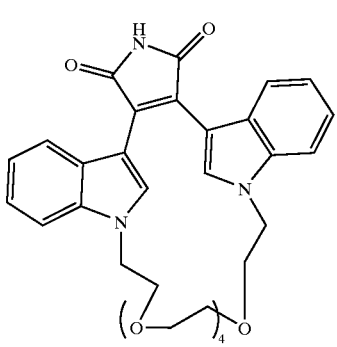
Compound 7

6,7,9,10,12,13-hexahydro-20H-5,23:14,19-dimetheno-5H-dibenzo[h,n]pyrrolo[3,4-k][1,4,7,16]dioxadiazacyclooctadecine-20,22(21H)-dione(Compound 4);

6,7,9,10,12,13,15,16,-octahydro-23H-5,26:17,22-dimetheno-5H-dibenzo[k,q]pyrrolo[3,4-n][1,4,7,10,19] trioxadiazacycloheneicosine-23,25(24H)-dione(Compound 5);

10,11,13,14,16,17,19,20,22,23-decahydro-9,4:24,29-dimetheno-1H-dibenzo[n,t]pyrrolo[3,4-q][1,4,7,10,13,22] tetraoxadiazacyclotetracosine-1,3(2H)-dione(Compound 6);

10,11,13,14,16,17,19,20,22,23,25,26-dodecahydro-9,4:27,32-dimetheno-1H-dibenzo[q,w]pyrrolo[3,4-t][1,4,7,10,13,16,25]pentaoxadiazacycloheptacosine-1,3(2H)-dione (Compound 7);

Preparation of Cpd 4

Triethylenebismesylate Compound 1e (0.58 g, 1.9 mmol) in DMF (15 mL) was delivered via syringe pump for 3 hours to a suspension of $Cs_2CO_3$ (1.0 g, 3.2 mmol) and starting material Compound 2a (0.5 g, 1.5 mmol, prepared as described in *Synthesis*, 1995, 511) in DMF (40 mL) at 100° C. Next the reaction mixture was cooled to 20° C. and stirred for 3 h. The reaction mixture was diluted with $NH_4Cl_{(aq)}$ and the product was extracted into $CH_2Cl_2$. The organic layer was washed with water, dried ($Na_2SO_4$) and concentrated. Product was purified by column chromatography ($CH_2Cl_2$/Acetone) to give 0.29 g (43%) of Compound 2c as a reddish brown solid; $^1H$ NMR (300 MHz, $CDCl_3$) δ 7.79 (d, J=8.0 Hz, 2H), 7.41 (s, 2H), 7.23 (m, 6H), 4.20 (t, J=4.5 Hz, 4H), 3.68 (t, J=4.5 Hz, 4H), 3.34 (s, 4H), 3.19 (s, 3H); MS (ES) m/z 456 (M+H$^+$).

A mixture of Compound 2b (0.1 g, 0.22 mmol) in EtOH (1 mL) and 10 N KOH (2.2 mmol) was heated to a gentle reflux at 78° C. overnight. The reaction mixture was cooled to 0° C. and acidified with 1 N HCl. A dark red precipitate was formed. $CH_2Cl_2$ was added and the organic layer was separated and washed with water, dried ($Na_2SO_4$) and concentrated. The product Compound 2f (0.088 g, 91%) was obtained as a dark red solid and used directly. A MeOH solution (0.05 mL) containing HMDS (0.32 g, 1.97 mmol) was added to a solution of Compound 2f (0.088 g, 0.2 mmol) in DMF (1.5 mL). The reaction was heated at 80° C. for 6 h. Upon completion the reaction was cooled and the solvent was evaporated under vacuum. The product was purified by column chromatography ($CH_2Cl_2$/Acetone) to give 0.32 g (36%) of Compound 4 as a dark red solid after recrystallization from ($CH_2Cl_2$/Hexane); $^1H$ NMR (300 MHz $CDCl_3$) δ 7.77 (d, J=8.1 Hz, 2H), 7.43 (s, 2H), 7.26 (m, 6H), 4.20 (m, 4H), 3.69 (m, 4H), 3.34 (s, 4H); MS (ES) m/z 442 (M+H$^+$).

Preparation of Cpd 5

Triethylenebismesylate Compound 1f (1.9 mmol) in DMF (15 mL) was delivered via syringe pump for 3 hours to a suspension of $Cs_2CO_3$ (1.0 g, 3.2 mmol) and starting material Compound 2a (0.5 g, 1.5 mmol) in DMF (40 mL) at 100° C. The reaction mixture was cooled to 20° C. and stirred for 2 h. The reaction mixture was diluted with $NH_4Cl_{(aq)}$ and the product was extracted into $CH_2Cl_2$. The organic layer was washed with water, dried ($Na_2SO_4$) and concentrated. Product was purified by column chromatography ($CH_2Cl_2$/Acetone) to give 0.457 g (62%) of Compound 2c; $^1H$ NMR (300 MHz, $CDCl_3$) δ 7.60 (s, 2H), 7.33 (brt, J=9.3 Hz, 4H), 7.19 (t, J=7.7 Hz, 2H), 6.99 (t, J=7.7 Hz, 2H), 4.25 (t, J=4.3 Hz, 4H), 3.66 (m, 4H), 3.18 (m, 11H); MS (ES) m/z 500 (M+H$^+$); Anal. Calcd. for $C_{29}H_{29}N_3O_5 \cdot 0.45H_2O$: C, 68.61; H, 5.94; N, 8.28. Found: C, 68.86; H, 6.12; N, 7.91

A mixture of Compound 2c (0.1 g, 0.2 mmol) in EtOH (1 mL) and 10 N KOH (2.0 mmol) was heated to a gentle reflux at 78° C. overnight. The reaction mixture was cooled to 0° C. and acidified with 1 N HCl. A dark red precipitate was formed. $CH_2Cl_2$ was added and the organic layer was separated and washed with water, dried ($Na_2SO_4$) and concentrated. The product Compound 2g (0.097 g, 100%) was obtained as a dark red solid and used directly. A MeOH solution (0.05 mL) containing HMDS (0.32 g, 1.97 mmol) was added to a solution of Compound 2g (0.097 g, 0.2 mmol) in DMF (1.5 mL). The reaction was heated at 80° C. for 6 h. Upon completion, the reaction was cooled and the solvent was evaporated under vacuum. The product was purified by column chromatography ($CH_2Cl_2$/Acetone) to give 0.78 g (80%) of Compound 5 as an orange solid after recrystallization from ($CH_2Cl_2$/Hexane); $^1H$ NMR (300 MHz, $CDCl_3$) δ 7.61 (s, 2H), 7.34 (m, 5H), 7.19 (t, J=7.0 Hz, 2H), 6.99 (t, J=7.0 Hz, 2H), 4.25 (t, J=4.5 Hz, 4H), 3.66 (t, J=4.5 Hz, 4H), 3.18 (s, 8H); MS (ES) m/z 486 (M+H$^+$). Anal. Calcd for $C_{28}H_{27}N_3O_5$: C, 69.26; H, 5.60; N, 8.65. Found: C, 69.49; H, 5.86; N, 8.34.

Preparation of Cpd 6

Pentaethylenebismesylate Compound 1g (0.75 g, 1.9 mmol) in DMF (15 mL) was added via syringe pump overnight to a suspension of $Cs_2CO_3$ (1.0 g, 3.2 mmol) and starting material Compound 2a (0.5 g, 1.5 mmol) in DMF (40 mL) at 100° C. The reaction mixture was cooled to 20° C. and stirred for 2 h. The reaction mixture was diluted with $NH_4Cl_{(aq)}$ and the product was extracted into $CH_2Cl_2$. The organic layer was washed with water, dried ($Na_2SO_4$) and concentrated. The product was purified by column chromatography ($CH_2Cl_2$/Acetone) to give 0.44 g (56%) of Compound 2d, $^1H$ NMR (300 MHz, $CDCl_3$) δ 7.56 (s, 2H), 7.32 (t, J=7.5 Hz, 4H), 7.21 (t, J=7.1 Hz, 2H), 7.01 (t, J=7.7 Hz, 2H), 4.22 (t, J=4.9 Hz, 4H), 3.72 (t, J=4.9 Hz, 4H), 3.47 (s, 4H), 3.42 (m, 4H), 3.34 (m, 4H), 3.20 (s, 3H); MS (ES) m/z 544 (M+H$^+$).

A mixture of Compound 2d (0.12 g, 0.22 mmol) in EtOH (1 mL) and 10 N KOH (2.2 mmol) was heated to a gentle reflux at 78° C. overnight. The reaction mixture was cooled to 0° C. and acidified with 1 N HCl. A dark red precipitate was formed. $CH_2Cl_2$ was added and the organic layer was separated and washed with water, dried ($Na_2SO_4$) and concentrated. The product Compound 2h (0.12 g, 100%) was obtained as a dark red solid and used directly. A MeOH solution (0.05 mL) containing HMDS (0.36 g, 2.3 mmol) was added to a solution of Compound 2h (0.12 g, 0.23 mmol) in DMF (1.5 mL) was added a MeOH solution (0.05 mL) containing HMDS (0.36 g, 2.3 mmol). The reaction was heated at 80° C. for 6 h. Upon completion the reaction was cooled and the solvent was evaporated under vacuum. Product was purified by column chromatography ($CH_2Cl_2$/Acetone) to give 0.066 g (55%) of Compound 6 as an orange solid; $^1H$ NMR (300 MHz, $CDCl_3$) δ 7.58 (s, 2H), 7.42 (s, 1H), 7.33 (m, 4H), 7.23 (t, J=6.6 Hz, 2H), 7.02 (t, J=7.0 Hz, 2H), 4.22 (t, J=4.9 Hz, 4H), 3.72 (t, J=4.9 Hz, 4H), 3.48 (s, 4H), 3.43 (m, 4H), 3.35 (m, 4H); MS (ES) m/z 530 (M+H$^+$). Anal. Calcd for $C_{30}H_{31}N_3O_6$·0.7$H_2O$: C, 66.46; H, 6.02; N, 7.75. Found: C, 66.35; H, 6.17; N, 7.50.

Preparation of Cpd 7

Hexaethylenebismesylate Compound 1h (0.84 g, 1.9 mmol) in DMF (15 mL) was added via syringe pump overnight to a suspension of $Cs_2CO_3$ (1.0 g, 3.2 mmol) and starting material Compound 2a (0.5 g, 1.5 mmol) in DMF (40 mL) at 100° C. The reaction mixture was cooled to 20° C. and stirred for 2 h. The reaction mixture was diluted with $NH_4Cl_{(aq)}$ and the product was extracted into $CH_2Cl_2$. The organic layer was washed with water, dried ($Na_2SO_4$) and concentrated. Product was purified by column chromatography ($CH_2Cl_2$/Acetone) to give 0.18 g (21%) of Compound 2e; $^1H$ NMR (300 MHz, $CDCl_3$) δ 7.63 (s, 2H), 7.40 (d, J=8.1 Hz, 2H), 7.17 (m, 4H), 6.92 (t, J=7.5 Hz, 2H), 4.25 (t, J=5.1 Hz, 4H), 3.75 (t, J=5.1 Hz, 4H), 3.40 (m, 16H), 3.20 (s, 3H); MS (ES) m/z 588 (M+H$^+$).

A mixture of Compound 2e (0.13 g, 0.22 mmol) in EtOH (1 mL) and 10 N KOH (2.2 mmol) was heated to a gentle reflux at 78° C. overnight. The reaction mixture was cooled to 0° C. and acidified with 1 N HCl. A dark red precipitate was formed. $CH_2Cl_2$ was added and the organic layer was separated and washed with water, dried ($Na_2SO_4$) and concentrated. The product Compound 2i (0.12 g, 92%) was obtained as a dark red solid and used directly. A MeOH solution (0.05 mL) containing HMDS (0.34 g, 2.1 mmol) was added to a solution of Compound 2i (0.12 g, 0.21 mmol) in DMF (1.5 mL). The reaction was heated at 80° C. for 5 h. Upon completion the reaction was cooled and the solvent was evaporated under vacuum. Product was purified by column chromatography ($CH_2Cl_2$/Acetone) to give 0.096 g (80%) of Compound 7 as a red solid; $^1H$ NMR (300 MHz, $CDCl_3$) δ 7.64 (s, 2H), 7.36 (s, 3H), 7.17 (m, 4H), 6.93 (t, J=7.8 Hz, 2H), 4.26 (t, J=5.1 Hz, 4H), 3.75 (t, J=5.1 Hz, 4H), 3.43 (m, 16H); MS (ES) m/z 574 (M+H$^+$). Anal. Calcd for $C_{32}H_{35}N_3O_7$: C, 67.00; H, 6.15; N, 7.33. Found: C, 66.63; H, 6.26; N, 7.21.

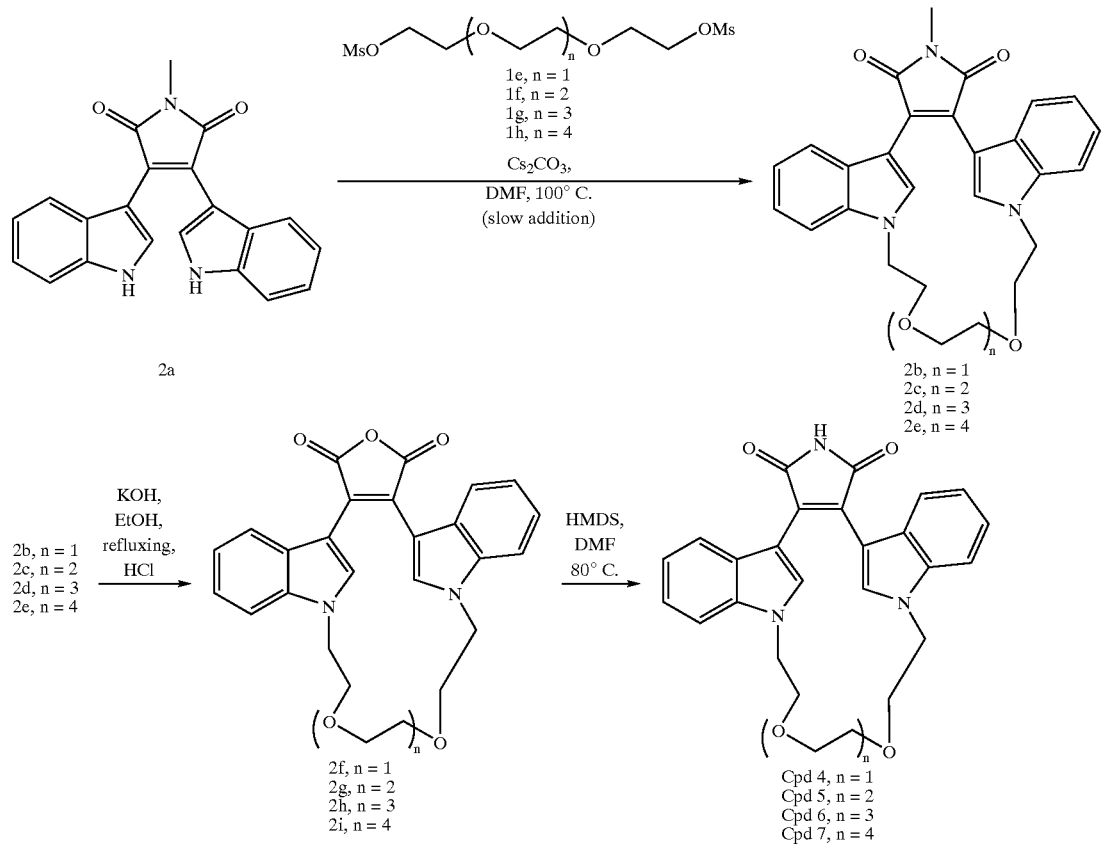

Example 3

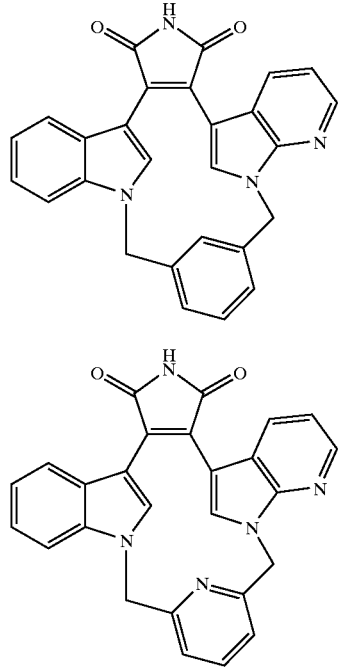

Compound 8

Compound 9

12-hydro-6H,19H-5,22:13,18:7,11-trimethenopyrido[2,3-j]pyrrolo[3,4-m][1,9]benzodiazacycloheptadecine-19,21(20H)-dione(Compound 8);
12-hydro-6H,19H-5,22:13,18-dimetheno-7,11-nitrilopyrido[2,3-j]pyrrolo[3,4-m][1,9]benzodiazacycloheptadecine-19,21(20H)-dione(Compound 9)

Preparation of Cpd 8

A mixture of chloro-indolylmaleimide Compound 3b (0.929 g, 3.57 mmol, prepared as described in Synthesis, 1995, 1511), organostannane Compound 3a (1.59 g, 3.57 mmol), lithium chloride (2.06 g, 49 mmol) and dichlorobis(triphenylphosphine)palladium(II) (0.34 g, 0.49 mmol) in toluene (45 mL) was heated at 95° C. under nitrogen overnight. The reaction mixture was concentrated under vacuum and $CH_2Cl_2$ (7.5 mL) and TFA (2.5 mL) were added. The reaction mixture was stirred at room temperature for 2.5 h, then concentrated under vacuum. The residue was purified by column chromatography ($CH_2Cl_2$/acetone) to give a mixture of an orange product and a 7-azaindole intermediate. The crude product was triturated in ether to remove the 7-azaindole and an orange solid of Compound 3c (0.376 g, 31%) was collected through filtration; $^1$H NMR (300 MHz, Acetone-$d_6$) δ 8.05 (d, J=4.0 Hz, 1H), 7.88 (s, 1H), 7.85 (s, 1H), 7.35 (d, J=8.2 Hz, 1H), 7.23 (d, J=8.1 Hz, 1H), 6.97 (t, J=7.8 Hz, 1H), 6.68 (m, 3H), 3.13 (s, 3H); FAB-HRMS (M+H$^+$). Calcd. for $C_{20}H_{15}N_4O_2$ 343.1195, found 343.1205.

A dihalo substituted aryl/heteroaryl Compound 3d (such as α,α'-dibromo-m-xylene; wherein X is a carbon atom and halo is a bromo atom) (200 mg, 0.756 mmol) in DMF (10 mL) was added over a 2 h period with a syringe pump to a slurry of Compound 3c (246 mg, 0.72 mmol) and $Cs_2CO_3$ (394 mg, 1.2 mmol) in DMF (20 mL) at 100° C. was held at 100° C. for 20 h. The mixture was concentrated under vacuum. Water was added and the residue was extracted with ethyl acetate and then with $CH_2Cl_2$. The extracts were combined, dried ($Na_2SO_4$) and concentrated. The product was purified by column chromatography ($CH_2Cl_2$/acetone as solvent) to give 135 mg (42%) of Compound 3e as a brick-red solid after recrystallization from ethyl acetate/hexanes; $^1$H NMR (300 MHz, CDCl$_3$) δ 8.38 (d, J=4.1 Hz, 1H), 8.21 (d, J=8.2 Hz, 1H), 7.83 (d, J=7.8 Hz, 1H), 7.44 (d, J=8.1 Hz, 1H), 7.25 (m, 6H), 7.09 (s, 1H), 7.03 (s, 1H) 6.69 (s, 1H), 5.42 (s, 2H), 5.16 (s, 2H), 3.23 (s, 3H); FAB-HRMS (M+H$^+$) Calcd. for $C_{27}H_{19}N_4O_2$ 445.1664, found 445.1660.

A mixture of Compound 3e (135 mg, 0.304 mmol) and 10 N KOH (0.85 mL) in ethanol (5 mL) was heated at a gentle reflux overnight. The reaction mixture was cooled in an ice bath, 1 N HCl (10 mL) was added and the mixture was stirred at 0° C. for 1 h. The reaction mixture was partitioned between $CH_2Cl_2$ (40 mL) and $NaHCO_{3(aq)}$ (40 mL). The separated aqueous layer was extracted again with $CH_2Cl_2$ (2×20 mL). The combined organic layers were dried ($Na_2SO_4$) and concentrated under vacuum to give a crude anhydride Compound 3g (48 mg). A MeOH (0.12 mL) solution containing hexamethyldisilazane (HMDS) (0.68 g, 4.2 mmol) was added to a solution of Compound 3g in DMF (2 mL). The reaction mixture was heated overnight at 80° C. The cooled reaction mixture was concentrated under vacuum, the product was purified by column chromatography ($CH_2Cl_2$/acetone as solvent) to give 28 mg (21%) of Compound 8 as a brick red solid after recrystallization from ether; $^1$H NMR (300 MHz, Methanol-$d_4$) δ 8.28 (m, 1H), 8.22 (d, J=8.0 Hz, 1H), 7.69 (d, J=7.8 Hz, 1H), 7.54 (d, J=8.2 Hz, 1H), 7.18 (m, 9H), 6.68 (s, 1H), 5.35 (s, 2H), 5.19 (s, 2H); FAB-HRMS (M+H$^+$) Calcd. for $C_{27}H_{19}N_4O_2$ 431.1508, found 431.1506.

Preparation of Cpd 9

A dihalo substituted aryl/heteroaryl Compound 3d (such as 2,6-bis(chloromethyl)pyridine; wherein X is a nitrogen atom and halo is a chloro atom) (133 mg, 0.756 mmol) in DMF (20 mL) was added over a 2 h period with a syringe pump to a slurry of Compound 3c (246 mg, 0.72 mmol) and $Cs_2CO_3$ (394 mg, 1.2 mmol) in DMF (20 mL) at 100° C. and was held at 100° C. for 20 h. The reaction mixture was concentrated under vacuum. Water was added and the residue was extracted with ethyl acetate and then with $CH_2Cl_2$. The extracts were combined, dried ($Na_2SO_4$) and concentrated. The product was purified by column chromatography ($CH_2Cl_2$/acetone as solvent) to give 103 mg (32%) of Compound 3f as a brick-red solid after being recrystallized from ethyl acetate/hexanes; $^1$H NMR (300 MHz, CDCl$_3$) δ 8.30 (m, 2H), 7.94 (bd, J=8.3 Hz, 1H), 7.64 (t, J=7.6 Hz, 1H), 7.42 (s, 1H), 7.27 (m, 7H), 5.56 (s, 2H), 5.28 (s, 2H), 3.25 (s, 3H); FAB-HRMS (M+H$^+$) Calcd. for $C_{27}H_{20}N_5O_2$ 446.1617, found 446.1630.

A mixture of Compound 3f (87 mg, 0.194 mmol) and 10 N KOH (0.55 mL) in ethanol (3 mL) was heated at a gentle reflux overnight. The reaction mixture was cooled in an ice bath. 12 N HCl (1 mL) and $CH_2Cl_2$ (6 mL) were added and the reaction mixture was stirred at 0° C. for 1 h. The reaction mixture was partitioned between $CH_2Cl_2$ (40 mL) and $NaHCO_{3(aq)}$ (40 mL). The separated aqueous layer was extracted again with $CH_2Cl_2$ (2×20 mL). The combined organic layers were dried ($Na_2SO_4$) and concentrated under vacuum to give an anhydride Compound 3h (66 mg). A MeOH (0.12 mL) solution containing HMDS (0.678 g, 2.1 mmol) was added to a solution of Compound 3h in DMF (4 mL). The reaction mixture was heated overnight at 80° C. The cooled reaction mixture was concentrated under vacuum, the product was purified by column chromatography ($CH_2Cl_2$/acetone as solvent) to give 50 mg (60%) of Compound 9 as a purple solid; $^1$H NMR (300 MHz, Acetone-$d_6$) δ 9.82 (bs, 1H), 8.27 (m, 2H), 7.85 (m, 2H), 7.61–7.39 (m, 5H), 7.17 (m, 3H), 5.67 (s, 2H), 5.52 (s MS(ES) m/z 432 (M+H$^+$). Anal. Calcd. for $C_{25}H_{17}N_5O_2 \cdot H_2O$: C, 69.48; H, 4.26; N, 15.58, Found: C, 69.20; H, 4.04; N, 15.45.

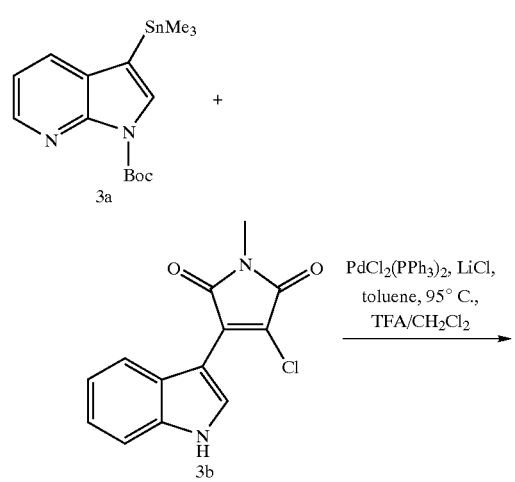
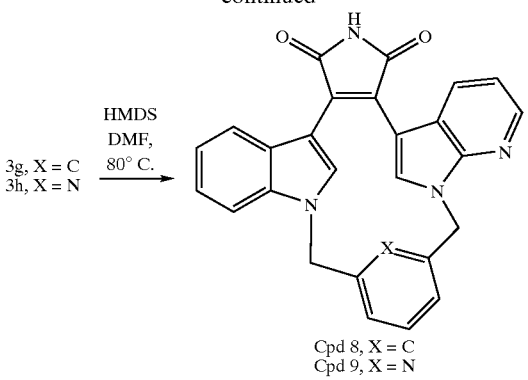
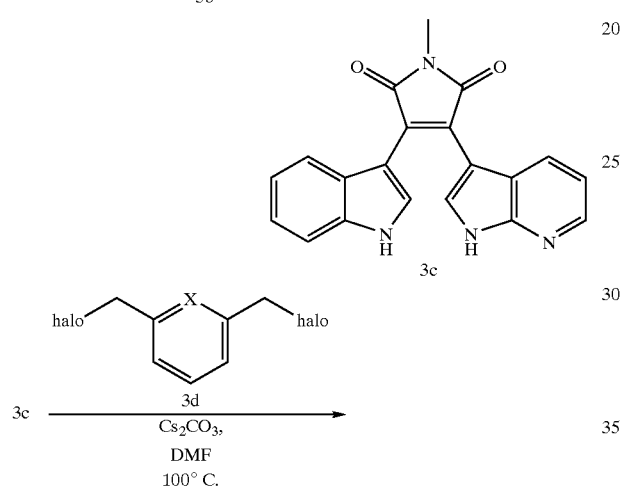
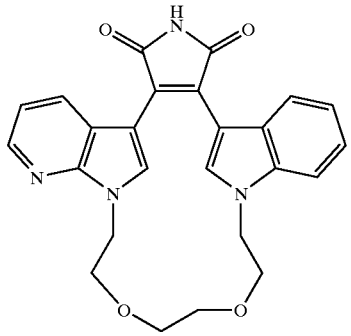

Example 4

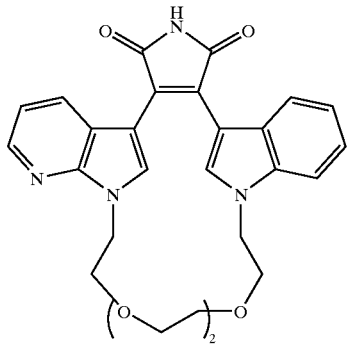

Compound 10

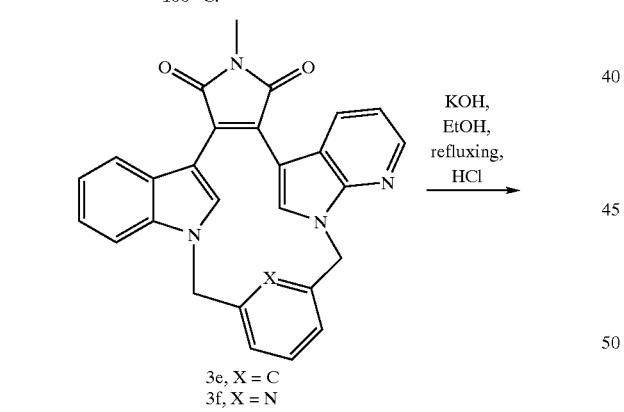
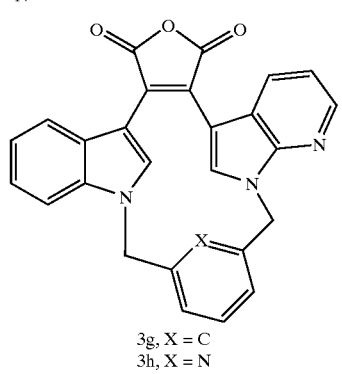

Compound 11

6,7,9,10,12,13-hexahydro-20H-5,23:14,19-dimetheno-5H-pyrido[2,3-k]pyrrolo[3,4-n][4,7,1,10]benzodioxadiazacyclooctadecine-20,22(21H)-dione (Compound 10; 6,7,9,10,12,13,15,16-octahydro-23H-5,26:17,22-dimetheno-5H-pyrido[2,3-n]pyrrolo[3,4-q][4,7,10,1,13]benzotrioxadiazacycloheneicosine-23,25(24H)-dione (Compound 11)

Preparation of Cpd 10

Bismesylate Compound 1e (220 mg, 0.72 mmol) in DMF (10 mL) was added over a 2 h period with a syringe pump to a slurry of Compound 3c (246 mg, 0.72 mmol) and $Cs_2CO_3$ (394 mg, 1.2 mmol) in DMF (20 mL) at 100° C. and was held at 100° C. for 20 h. The mixture was concentrated under vacuum. Water was added and the residue was extracted with $CH_2Cl_2$ then dried ($Na_2SO_4$) and concentrated. The product was purified by column chromatography ($CH_2Cl_2$/acetone as solvent) to give 160 mg (49%) of Compound 4a as a brick red solid; $^1$H NMR (300 MHz, CDCl$_3$) δ 8.33 (d, J=4.8 Hz, 1H), 8.25 (d, J=7.0 Hz, 1H), 7.65 (d, J=7.8 Hz, 1H), 7.59 (s, 1H), 7.45 (s, 1H), 7.34 (d, J=8.1 Hz, 1H), 7.26 (m, 1H), 7.16 (m, 2H), 4.37 (t, J=4.5 Hz, 2H), 4.27 (t, J=4.7 Hz, 2H), 3.76 (t, J=4.8 Hz, 2H), 3.69 (t, J=4.5 Hz, 2H), 3.38 (m, 4H), 3.20 (s, 3H). MS(ES) m/z 457 (M+H$^+$). Anal. Calcd for C$_{26}$H$_{24}$N$_4$O$_4$.1.5H$_2$O: C, 64.59; H, 5.63; N, 11.59, Found: C, 64.99; H, 5.27; N, 11.44.

A mixture of Compound 4a (124 mg, 0.271 mmol) and 10 N KOH (0.77 mL) in ethanol (4.2 mL) was heated at a gentle reflux overnight. The reaction mixture was cooled in an ice bath, 12 N HCl (2.3 mL) and CH$_2$Cl$_2$ (3 mL) were added and the reaction mixture was stirred at 0° C. for 20 min. The reaction mixture was partitioned between CH$_2$Cl$_2$ (40 mL) and NaHCO$_{3(aq)}$ (40 mL). The separated aqueous layer was extracted again with CH$_2$Cl$_2$ (2×20 mL). The combined organic layers were dried (Na$_2$SO$_4$) and concentrated under vacuum to give a crude anhydride Compound 4c (120 mg). A MeOH (0.2 mL) solution containing HMDS (1.19 g, 7.46 mmol) was added to a solution of the anhydride in DMF (7 mL). The reaction mixture was heated overnight at 80° C. The cooled reaction mixture was concentrated under vacuum and the product was purified by column chromatography (CH$_2$Cl$_2$/acetone as solvent) to give 39 mg (33%) of Compound 10 as an orange solid; $^1$H NMR (300 MHz, DMSO-d$_6$) δ 11.05 (bs, 1H), 8.29 (d, J=3.3 Hz, 1H), 8.11 (d, J=7.9 Hz, 1H), 7.74 (s, 1H), 7.62 (s, 1H), 7.54 (d, J=8.4 Hz, 2H), 7.18 (m, 2H), 7.05 (t, J=7.8 Hz, 1H), 4.36 (m, 4H), 3.68 (m, 4H), 3.39 (m, 4H). FAB-HRMS (M+H$^+$) Calcd. for C$_{25}$H$_{23}$N$_4$O$_4$ 443.1719, found 443.1713.

Preparation of Cpd 11

Bismesylate Compound 1f (252 mg, 0.72 mmol) in DMF (10 mL) was added over a 2 h period with a syringe pump to a slurry of Compound 3c (246 mg, 0.72 mmol) and Cs$_2$CO$_3$ (394 mg, 1.2 mmol) in DMF (20 mL) at 100° C. and was held at 100° C. for 20 h. The mixture was concentrated under vacuum. Water was added and the residue was extracted with CH$_2$Cl$_2$, dried (Na$_2$SO$_4$) and concentrated. The product was purified by column chromatography (CH$_2$Cl$_2$/acetone as solvent) to give 100 mg (27%) of Compound 4b as an orange solid after recrystallization from ethyl acetate/hexanes; $^1$H NMR (300 MHz, CDCl$_3$) δ 8.34 (d, J=3.7 Hz, 1H), 8.05 (d, J=7.1 Hz, 1H), 7.78 (s, 1H), 7.62 (s, 1H), 7.40 (d, J=8.2 Hz, 1H), 7.14 (m, 2H), 6.90 (m, 2H), 4.44 (m, 2H). 4.35 (m, 2H), 3.77 (m, 2H), 3.60 (m, 2H), 3.38 (m, 4H), 3.20 (s, 3H), 3.02 (m, 4H). MS(ES) m/z 501 (M+H$^+$). Anal. Calcd for C$_{28}$H$_{28}$N$_4$O.0.5H$_2$O: C, 66.00; H, 5.74; N, 11.00, Found: C, 65.88; H, 5.75; N, 10.93.

A mixture of Compound 4b (58 mg, 0.116 mmol) and 10 N KOH (0.33 mL) in ethanol (1.8 mL) was heated at a gentle reflux overnight. The reaction mixture was cooled in an ice bath, 12 N HCl (1 mL) and CH$_2$Cl$_2$ (6 mL) were added and the reaction mixture was stirred at 0° C. for 20 min. The reaction mixture was partitioned between CH$_2$Cl$_2$ (40 mL) and NaHCO$_{3(aq)}$ (40 mL). The separated aqueous layer was extracted again with CH$_2$Cl$_2$ (2×20 mL). The combined organic layers were dried (Na$_2$SO$_4$) and concentrated under vacuum to give a crude anhydride Compound 4c (60 mg). A MeOH (0.1 mL) solution containing HMDS (0.51 g, 3.2 mmol) was added to a solution of the anhydride in DMF (3 mL). The reaction mixture was heated overnight at 80° C. The cooled reaction mixture was concentrated under vacuum and then the product was purified by column chromatography (CH$_2$Cl$_2$/acetone as solvent) to give 47 mg (83%) of Compound 11 as an orange solid; $^1$H NMR (300 MHz, Acetone-d$_6$) δ 9.66 (bs, 1H), 8.31 (d, J=4.0 Hz, 1H), 7.98 (d, J=8.1 Hz, 1H), 7.83 (s, 1H), 7.64 (s, 1H), 7.56 (d, J=8.4 Hz, 1H), 7.12 (m, 2H), 6.87 (d, J=4.0 Hz, 2H), 4.43 (m, 4H), 3.83 (m, 2H), 3.61 (m, 2H), 3.33 (m, 4H), 3.07 (s, 4H). Anal. Calcd for C$_{27}$H$_{26}$N$_4$O$_5$.0.7H$_2$O: C, 64.97; H, 5.53; N, 11.22, Found: C, 65.40; H, 5.64; N, 10.80; FAB-HRMS (M+H$^+$) Calcd. C$_{27}$H$_{27}$N$_4$O$_5$ 487.1981, found 487.1964.

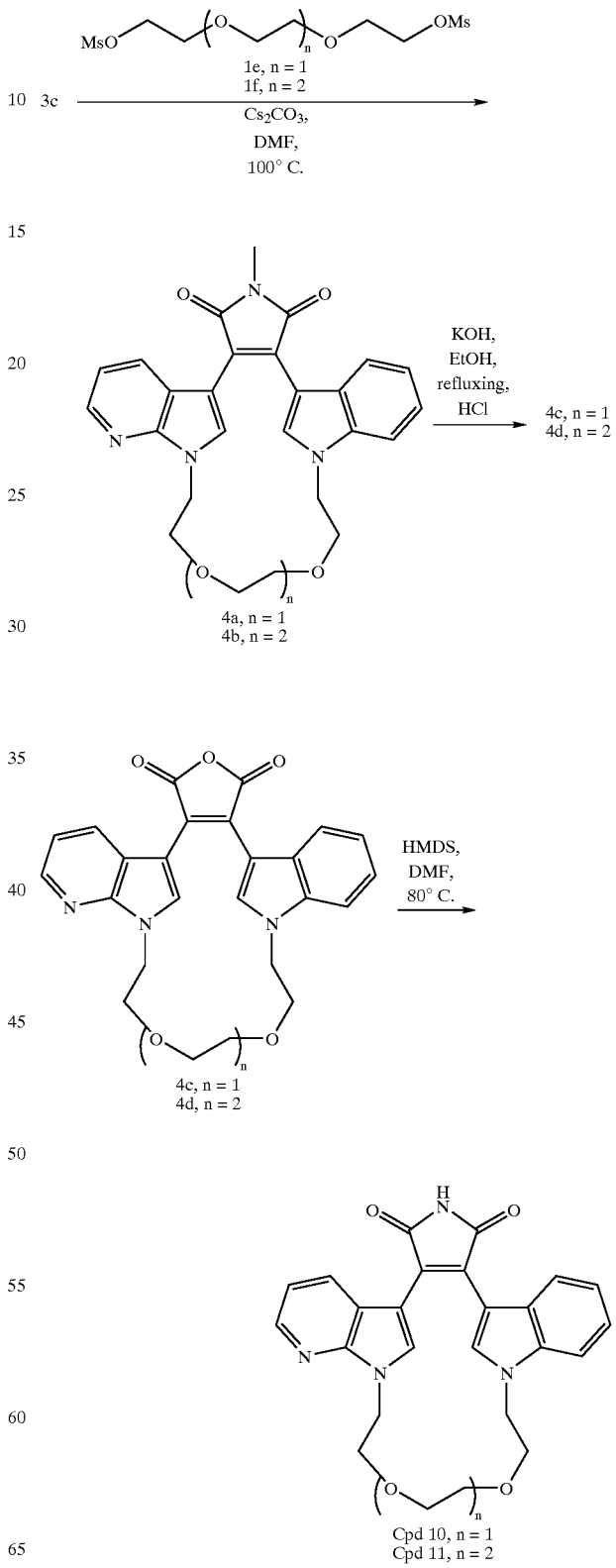

Example 5

Compound 12

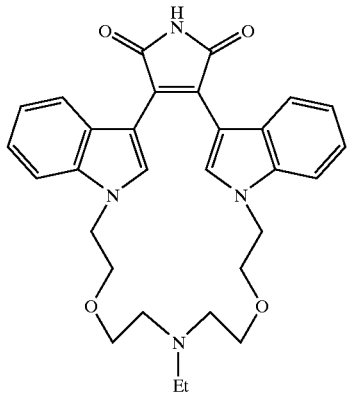

Compound 13

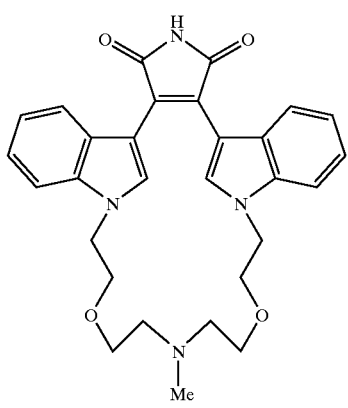

Compound 14

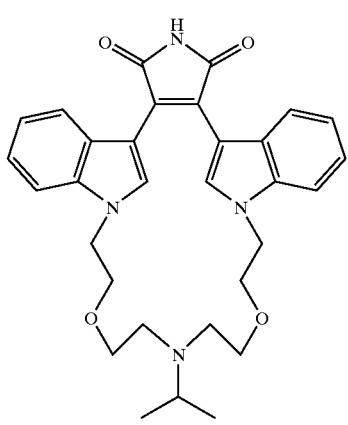

11-ethyl-6,7,10,11,12,13,15,16-octahydro-23H-5,26:17,22-dimetheno-5H,9H-dibenzo[k,q]pyrrolo[3,4-n][1,7,4,10,19]dioxatriazacycloheneicosine-23,25 (24H)-dione (Compound 12);
6,7,10,11,12,13,15,16-octahydro-11-methyl-23H-5,26:17,22-dimetheno-5H,9H-dibenzo[k,q]pyrrolo[3,4-n][1,7,4,10,19]dioxatriazacycloheneicosine-23,25 (24H)-dione (Compound 13);
6,7,10,11,12,13,15,16-octahydro-11-(1-methylethyl)-23H-5,26:17,22-dime theno-5H,9H-dibenzo[k,q]pyrrolo[3,4-n][1,7,4,10,19]dioxatriazacycloheneicosine-23,25(24H)-dione (Compound 14)

Preparation of Cpd 12

A suspension of 10.0 g (53 mmol) of Compound 5a in 350 mL of a dichloromethane:methanol 6:1 mixture was stirred and cooled in an ice bath while adding 79 mL of a 2.0 M solution of TMSCHN$_2$ in hexane dropwise over a 1 hr period. The mixture was allowed to warm to room temperature and stirring continued over night. The resulting light yellow solid was filtered and washed with ether to yield 7.5 g (70%) of Compound 5b. $^1$H NMR (DMSO-d$_6$) δ 12.5 (s, 1H), 8.45 (d, 1H), 8.2 (d, 1H), 7.55 (d, 1H), 7.3 (m, 2H), 3.95 (s, 3H). 1.0 M potassium tert-butoxide (51.6 mL, 51.6 mmol) was added dropwise over 1 hr to a mixture of Compound 5b (3.84 g, 18.9 mmol) and 3-indolyl acetamide Compound 5c (3.00 g, 17.2 mmol) in dry THF (30 mL) previously cooled to 0° C. Next the reaction mixture was stirred at 0° C. for 15 min, then at room temperature for 3 h. The reaction was quenched with conc. hydrochloric acid (24 mL) with vigorous stirring for 5 min. The reaction mixture was diluted with ethyl acetate and washed with water. The ethyl acetate layer was washed with water, then brine, then dried (MgSO$_4$), and evaporated in vacuo to give a solid Compound 5d (6.89 g). Compound 5d (6.79 g) was dissolved in dry acetone (170 mL) followed by the addition of pulverized potassium carbonate (3.15 g, 22.8 mmol) and dimethyl sulfate (2.16 mL, 22.8 mmol). The reaction was heated to reflux for 5 h. The reaction was cooled to room temperature and evaporated in vacuo to a red solid. The red solid was stirred in ethyl acetate/methanol (10:1, 550 mL), dried (Na$_2$SO$_4$) and evaporated in vacuo. The crude product was chromatographed (silica gel, EtOAc/Hexane, from 1:4 to 2:3) to give a solid Compound 5e (1.78 g, 30% overall yield from Compound 5c). $^1$HNMR (DMSO-d$_6$) δ 3.04 (s, 3H), 6.60–6.72 (m, 2H), 6.81 (d, 2H, J=10.45 Hz), 6.95–7.00 (m, 2H), 7.36 (d, 2H, J=7.99 Hz), 7.75 (d, 2H, J=2.59 Hz), 11.67 (s 2H). ES-MS m/z 341 (MH$^+$).

Compound 5e (1.50 g, 4.40 mmol) was dissolved in dry DMF (300 mL) followed by the addition of 2-bromoethyl ether (5.53 mL, 44.0 mmol) and cesium carbonate (5.73 g, 17.6 mmol). The reaction was stirred at 80° C. for 8 hr. and then additional 2-bromoethyl ether (1.12 mL, 8.80 mm) was added and the reaction stirred at 80° C. for 4 hr. The reaction was cooled to room temperature and filtered through celite. The filtrate was diluted with ethyl acetate (20 mL), washed with water (2×), then brine (1×), then dried (Na$_2$SO$_4$), and evaporated in vacuo. The crude product was chromatographed (silica gel, EtOAc/Hexane, from 1:4 to 1:1) to give Compound 5g (1.06 g, 37%). $^1$HNMR (CDCl$_3$) δ 3.18 (s, 3H), 3.32–3.36 (m, 4H), 3.59–3.66 (m, 4H), 3.81–3.85 (m, 4H), 4.31 (t, 4H, J=5.42), 6.73 (t, 2H, J=7.22), 6.98 (d, 2H, J=8.02), 7.07–7.12 (m, 2H), 7.31 (d, 2H, J=8.25), 7.72 (s, 2H, H-2). ES-MS m/z 644 (MH$^+$). A solution of Compound 5g (0.40 g, 0.62 mmol), diisopropylethylamine (1.29 mL, 7.4 mmol), and ethylamine (2.0 M in THF, 1.85 mL, 3.7 mmol) in dry THF (103 mL) was stirred at 90° C. overnight. The reaction was cooled to room temperature and additional diisopropylethylamine (0.64 mL, 3.7 mmol) and 2.0 M ethylamine Compound 5h in THF (0.92 mL, 1.85 mmol) were added. The mixture was stirred at 90° C. overnight. The reaction mixture was cooled to room temperature and evaporated in vacuo to give a Compound 5k (0.59 g). The crude Compound 5k (0.59 g) was suspended in EtOH (24 mL) followed by the addition of potassium hydroxide (0.93 g, 16.5 mmol). The reaction was stirred at reflux overnight. The reaction was cooled to room temperature and evaporated in vacuo. The remaining residue was dissolved in water (55 mL) and acidified with 10% citric acid. The mixture was stirred at room temperature for 10 min and was evaporated in vacuo. The resulting solid was treated with neat ammonium acetate (60 g) and stirred at 140° C. for 3 hrs. The reaction was cooled to room temperature, diluted with water, basified with 20% sodium hydroxide to pH=10, and extracted with ethyl acetate (2×80 mL). The organic layer was washed with water (60 mL), then brine (60 mL), then dried (Na$_2$SO$_4$), and evaporated in vacuo. The crude product was chromatographed (silica gel, DCM/MeOH/NH$_4$OH, from 95:3:2 to 93:5:2) to produce the target Compound 12 (38.5 mg). $^1$HNMR (CD$_3$OD) δ 0.95–1.00 (m, 3H), 2.42–2.45 (m, 4H), 2.51–2.58 (q, 2H), 3.14–3.18 (m, 4H), 3.61–3.64 (m, 4H), 4.25–4.28 (m, 4H), 6.89–6.94 (m, 2H), 7.10–7.19 (m, 4H), 7.44 (d, 2H, J=8.23), 7.61 (s, 2H). ES-MS m/z 513 (MH$^+$).

Preparation of Cpd 13

Using the procedure for the preparation of Compound 12 and the appropriate reagents and starting materials known to those skilled in the art, Compound 13 was prepared: $^1$HNMR (CD$_3$OD) δ 2.16 (s, 3H), 2.29–2.32 (m, 4H), 3.1–3.20 (m, 4H), 3.65–3.67 (m, 4H), 4.30–4.33 (m, 4H), 6.93–6.95 (m, 2H), 7.17–7.21 (m, 4H), 7.47 (d, 2H, J=8.29 Hz), 7.65 (s, 2H). ES-MS m/z 499 (MH$^+$).

Preparation of Cpd 14

Using the procedure for the preparation of Compound 12 and the appropriate reagents and starting materials known to those skilled in the art, Compound 14 was prepared: ES-MS m/z 527 (MH$^+$).

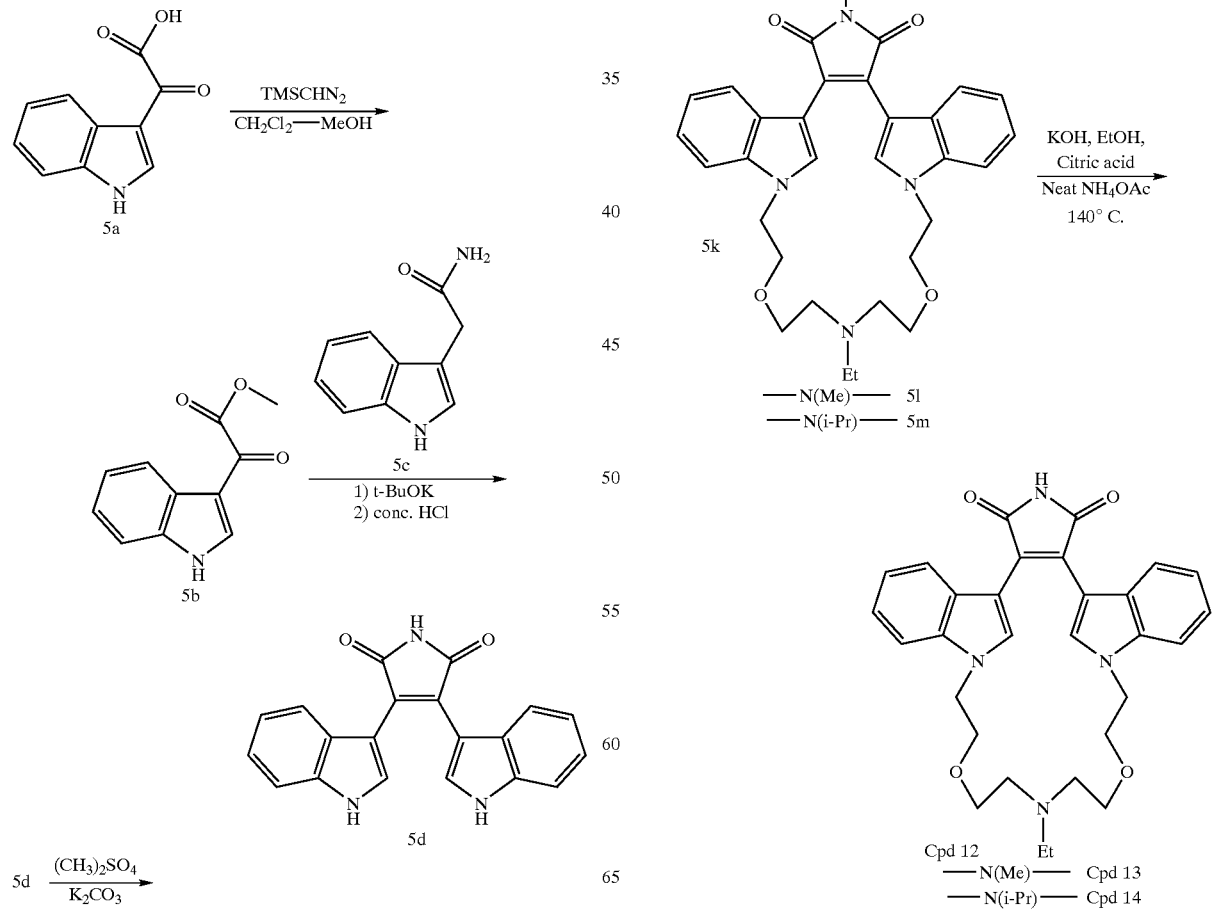

Example 6

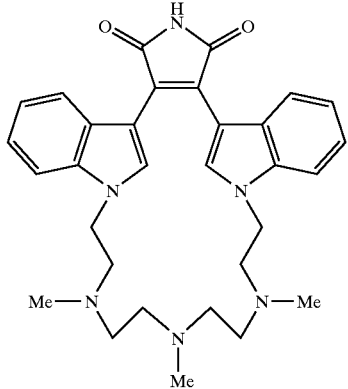

7,8,9,10,11,12,13,14,15,16-decahydro-8,11,14-trimethyl-6H,23H-5,26:17,22-dimethenodibenzo[n,t]pyrrolo[3,4-q][1,4,7,10,13]pentaazacycloheneicosine-23,25(24H)-dione (Compound 15)

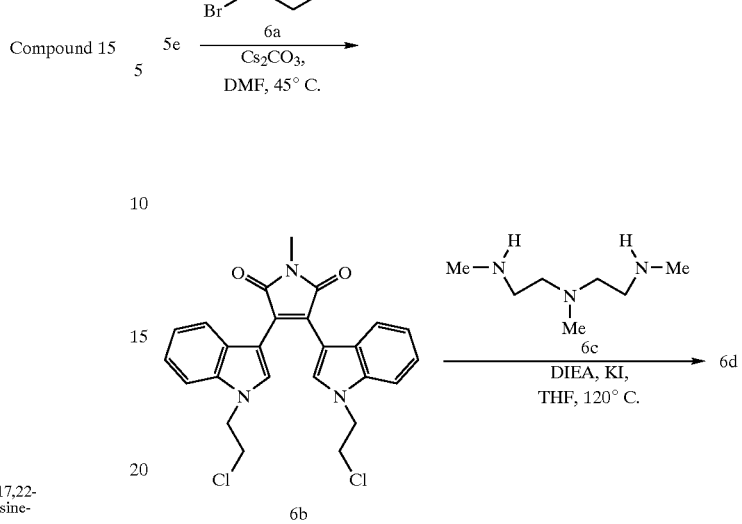

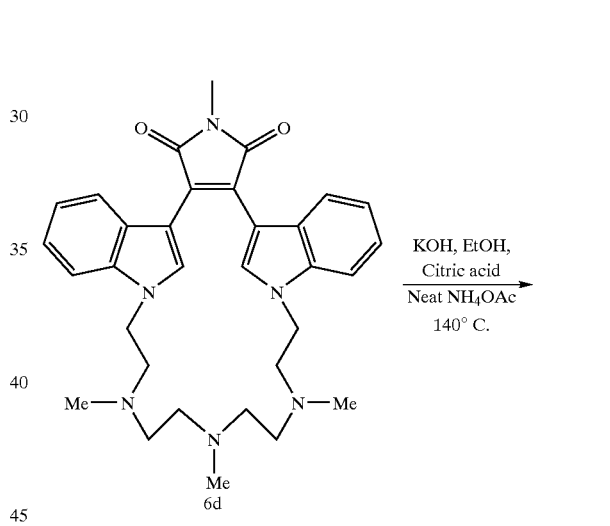

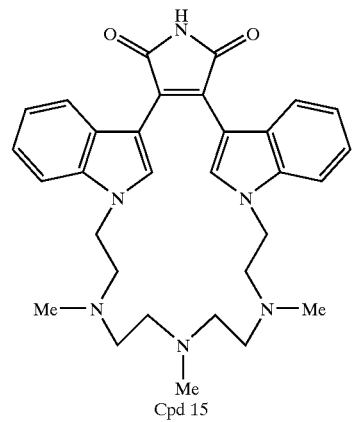

A 1-bromo-2-chloroethane Compound 6a (430 mg, 3.0 mmol) was added to a mixture of Compound 5e (51 mg, 0.15 mmol) and cesium carbonate (122 mg, 0.38 mmol) in DMF (4 mL). The reaction mixture was stirred at 45° C. for 16 h and then cooled to room temperature. The mixture was diluted with EtOAc (50 mL), washed with water, then brine, then dried ($Na_2SO_4$), and evaporated in vacuo to give Compound 6b (69 mg), CI-MS m/z 466 ($MH^+$). A solution of the crude Compound 6b (26 mg), 1,4,7-trimethyldiethylenetriamine Compound 6c (10 mg, 0.07 mmol), KI (28 mg, 0.17 mmol) and N,N-diisopropylethylamine (44 mg, 0.34 mmol) in THF (8 mL) was stirred at 80 C for 8 h, at which time TLC indicated that the reaction was only partially complete. Additional trimethyldiethylenetriamine (20 mg, 0.14 mmol) was added and the stirring was continued at 120° C. for 42 h. The reaction mixture was then diluted with EtOAc (50 mL), washed with water, then brine, then dried ($Na_2SO_4$), and evaporated in vacuo. The resulting residue Compound 6d (ES-MS m/z 539 ($MH^+$)) was dissolved in EtOH (4 mL) and treated with KOH (63 mg, 1.1 mmol). The mixture was stirred at 80° C. for 40 h, and then EtOH was removed under vacuo. The residue was dissolved in water (3 mL) and acidified with 10% citric acid (5 mL). The mixture was stirred at room temperature for 10 min and then dried in vacuo. The resulting solid was stirred with neat ammonium acetate (4.0 g) at 140° C. for 2.5 h, and the mixture was cooled to room temperature, diluted with $H_2O$ (3 mL), basified to pH=ca. 10 with 20% aq. sodium hydroxide. The solution was extracted with EtOAc (40 mL×2). The organic layer was washed with water, then brine, then dried ($Na_2SO_4$), and evaporated in vacuo to afford crude product, which was separated by prep. TLC using $CH_2Cl_2$/MeOH/$NH_4OH$ (85:13:2) to give Compound 15 as a red-orange solid (12 mg, 41% overall yield from Compound 5e). $^1$HNMR ($CDCl_3$) δ 7.52 (s, 2H), 7.34–7.30 (m, 4H), 7.20 (t, J=7.1, 7.9 Hz, 2H), 7.00 (t, J=7.0, 7.9 Hz, 2H), 4.08 (m, 4H), 2.67 (m, 4H), 2.32–2.10 (m, 8H), 2.19 (s, 9H); ES-MS m/z 525 ($MH^+$).

Example 7

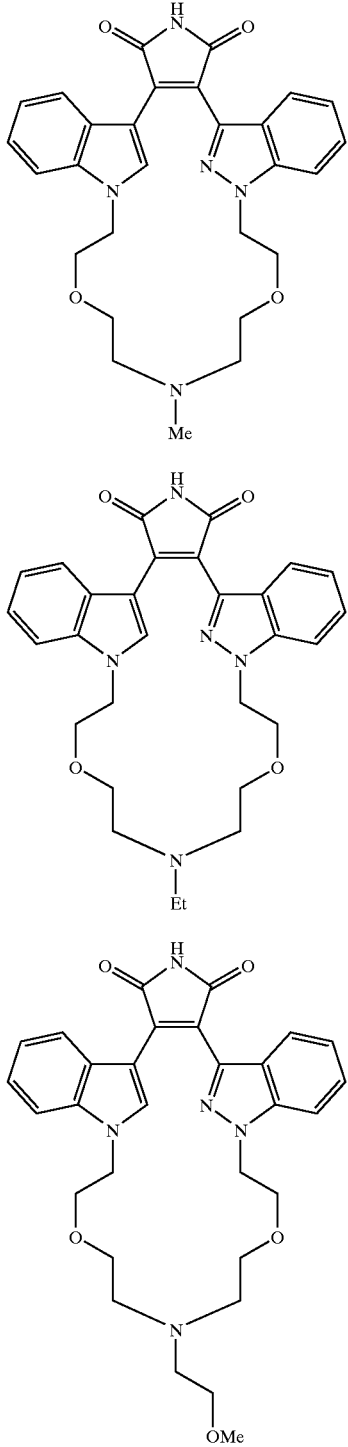

Compound 16

Compound 17

Compound 29

6,7,10,11,12,13,15,16-octahydro-11-methyl-23H-5,26-metheno-17,22-nitrilo -5H,9H-dibenzo[k,q]pyrrolo[3,4-n][1,7,4,10,19]dioxatriazacyclohenexicosine-23,25 (24H)-dione (Compound 16);
11-ethyl-6,7,10,11,12,13,15,16-octahydro-23H-5,26-metheno-17,22-nitrilo- 5H,9H-dibenzo[k,q]pyrrolo[3,4-n][1,7,4,10,19]dioxatriazacyclohenexicosine-23,25 (24H)-dione (Compound 17);
6,7,10,11,12,13,15,16-octahydro-11-(2-methoxyethyl)-23H-5,26-metheno-1 7,22-nitrilo-5H,9H-dibenzo[k,q]pyrrolo[3,4-n][1,7,4,10,19]dioxatriazacyclohen eicosine-23,25(24H)-dione (Compound 29)

Preparation of Cpd 16

A mixture of Compound 5b (2.03 g, 10.0 mmol), Compound 7a (3.10 g, 13.0 mmol, prepared from 2-(2-chloroethoxy)ethanol and TBDMS-Cl) and cesium carbonate (4.69, 14.4 mmol) in DMF (40 mL) was stirred at 70° C. for 8 h, and then filtered. The filtrate was evaporated in vacuo and the residue was separated by flash column chromatography (hexane/EtOAc, 3:1) to give Compound 7b as a light yellow viscous oil (1.83 g, 45% yield). $^1$HNMR (CDCl$_3$) δ 8.45–8.42 (m, 2H), 7.59–7.30 (m, 3H), 4.34 (t, J=5.3 Hz, 2H), 3.93 (s, 3H), 3.87 (t, J=5.3 Hz, 2H), 3.68 (t, J=5.3, 4.8 Hz, 2H), 3.47 (t, J=5.3, 4.8 Hz, 2H), 0.84 (s, 9H), 0.01 (s, 6H); ES-MS m/z 406 (MH$^+$).

An acid Compound 7c (5.28 g, 30 mmol, prepared according to *J. Med. Chem.* 1992, 35, 2160) was dissolved in DCM (120 mL), and DMF (30 mL) under argon, HOBT (4.45 g, 33 mmol) and DCC (6.51 g, 32 mmol) were added and the reaction was stirred at ambient temperature for 1 h. Ammonium hydroxide (28%, 2.7 g, 44 mmol) was added over 5 min and the reaction was then stirred at ambient temperature for 16 h. White solid was filtered and the filtrate diluted with DCM (150 mL) and filtered again. The DCM solution was extracted four times with 5% NaHCO$_3$ (150 mL); the combined aqueous solution was treated with sodium chloride (190 g) and extracted with ethyl acetate (300 mL) six times. The organic extract was dried (Na$_2$SO$_4$) and evaporated in vacuo to a solid, which was triturated with diethyl ether (100 mL) and filtered to afford a white solid Compound 7d (3.52 g, 67%). A mixture of Compound 7d (700 mg, 4.0 mmol), 2-(2-chloroethoxy)ethanol Compound 7e (997 mg, 8.0 mmol) and cesium carbonate (1.56 g, 4.8 mmol) in DMF (20 mL) was stirred at 70° C. for 16 h, and then filtered. The filtrate was evaporated in vacuo and the residue was separated by flash column chromatography (CH$_2$Cl$_2$/MeOH, 9:1) to give Compound 7f as a light yellow solid (495 mg, 47% yield). $^1$HNMR (CD$_3$OD) δ 7.74 (d, J=8.1 Hz, 1H), 7.58 (d, J=8.6 Hz, 1H), 7.40 (t, J=8.2, 7.1 Hz, 1H), 7.14 (t, J=8.5 Hz, 1H), 4.56 (t, J=5.4 Hz, 2H), 3.92–3.89 (m, 4H), 3.52 (m, 2H), 3.45 (m, 2H); ES-MS m/z 264 (MH$^+$).

1.0 M potassium t-butoxide in THF (4 mL, 4.0 mmol) was added dropwise to a suspension of the ester Compound 7b (487 mg, 1.2 mmol) and amide Compound 7f (210 mg, 0.8 mmol) in dry THF (10 mL) under argon that had been cooled to 0° C. The resulting mixture was stirred at 0° C. for 10 min and room temperature for 3 h, and then concentrated HCl (5 mL) was added, stirred at room temperature for another 10 min. The mixture was partitioned between EtOAc (100 mL) and H$_2$O (40 mL). Two layers were separated, and the aqueous layer was extracted with EtOAc (50 mL). The combined extracts were washed with water, then saturated aq. NaHCO$_3$, then brine, then dried (Na$_2$SO$_4$), and evaporated in vacuo to yield Compound 7g as a dark red-orange solid (388 mg). ES-MS m/z 505 (MH$^+$). Ms$_2$O (440 mg, 2.5 mmol) was added to a solution of the crude Compound 7g (255 mg) and pyridine (320 mg, 4.0 mmol) in THF (14 mL). The reaction was stirred at 50° C. for 2 h and then the reaction mixture was cooled to room temperature. Then THF (10 mL) and 1.0 N aq. HCl (20 mL) were added. The mixture was stirred at room temperature for 10 min and then extracted with EtOAc (120 mL). The organic phase was washed with 1.0 N aq. HCl (20 mL), then water, then brine, then dried (Na$_2$SO$_4$), and evaporated in vacuo to give Compound 7h as a dark red-orange solid (386 mg). ES-MS m/z 661 (MH$^+$). A solution of the crude Compound 7h (76 mg) N,N-diisopropylethylamine (259 mg, 2.0 mmol) and MeNH$_2$ Compound 7i (2.0 M in THF, 0.90 mL, 1.8 mmol)

in THF (10 mL) in a pressure tube was stirred at 90° C. for 22 h. The volatiles were removed under vacuo and the residue was separated by flash column chromatography (CH$_2$Cl$_2$/MeOH/NH$_4$OH, 88:12:0.5) to give the desired product Compound 16 as a red-orange solid (20 mg, 40% overall yield from Compound 7f). $^1$HNMR (CD$_3$OD) δ 7.66 (s, 1H), 7.61–7.32 (m, 5H), 7.23–7.20 (m, 1H), 7.07–7.00 (m, 2H), 4.51 (t, J=5.5 Hz, 2H), 4.22 (t, J=4.6 Hz, 2H), 3.64–3.59 (m, 4H), 3.34 (t, J=5.1 Hz, 2H), 3.09 (t, J=5.1 Hz, 2H), 2.43 (t, J=5.1 Hz, 2H), 2.23 (t, J=5.0 Hz, 2H), 2.17 (s, 3H); ES-MS m/z 500 (MH$^+$).

Preparation of Cpd 17

Using the procedure for the preparation of Compound 16 and the appropriate reagents and starting materials known to those skilled in the art, Compound 17 was prepared: $^1$HNMR (CD$_3$OD) δ 7.88 (s, 1H), 7.64 (d, J=8.5 Hz, 1H), 7.57 (d, J=8.2 Hz, 1H), 7.47 (m, 2H), 7.20–7.13 (m, 2H), 6.86–6.77 (m, 2H), 4.53 (t, J=4.8 Hz, 2H), 4.36 (t, J=4.7 Hz, 2H), 3.75 (t, J=4.7, 5.0 Hz, 2H), 3.62 (t, J=4.8 Hz, 2H), 3.34 (m, 2H), 3.17 (t, J=5.0 Hz, 2H), 2.77 (m, 4H), 2.63 (t, J=5.0 Hz, 2H), 1.08 (t, J=7.2 Hz, 3H); ES-MS m/z 514 (MH$^+$).

Preparation of Cpd 29

Using the procedure for the preparation of Compound 16 and the appropriate reagents and starting materials known to those skilled in the art, Compound 29 was prepared: $^1$HNMR (CD$_3$OD) (free base) δ 7.86 (s, 1H), 7.55 (d, J=8.2 Hz, 1H), 7.45–7.37 (m, 3H), 7.19 (t, J=6.8, 8.2 Hz, 1H), 7.11 (t, J=6.6, 7.9 Hz, 1H), 6.97–6.91 (m, 2H), 4.46 (t, J=5.0 Hz, 2H), 4.25 (m, 2H), 3.68–3.31 (m, 10H), 3.27 (s, 3H), 2.95 (m, 2H), 2.77 (m, 2H), 2.68 (m, 2H); ES-MS m/z 544 (MH$^+$).

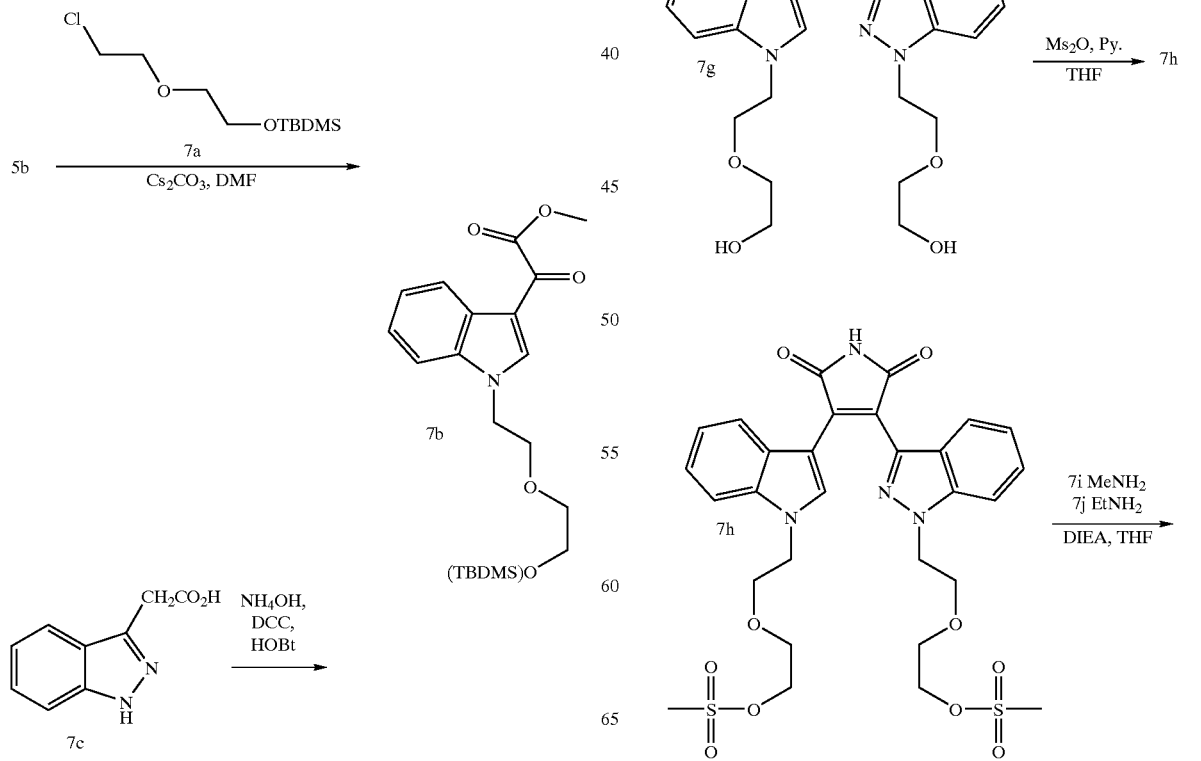

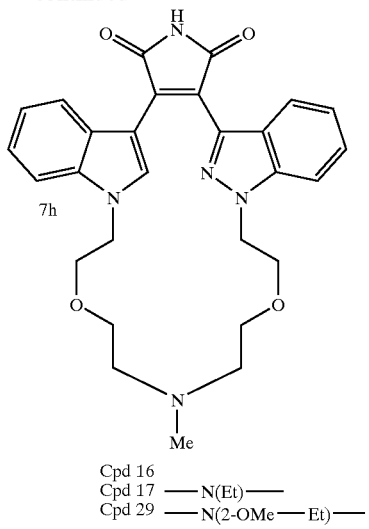

| | |
|---|---|
| Cpd 16 | |
| Cpd 17 | —N(Et)— |
| Cpd 29 | —N(2-OMe—Et)— |

Example 8

Compound 18

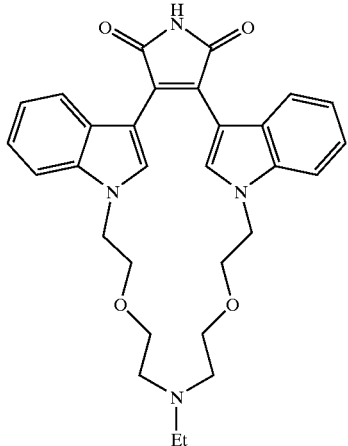

11-ethyl-6,7,10,11,12,13,15,16-octahydro-23H-5,26:17,22-dimetheno-5H,9H-dipyrido[2,3-k:3',2'-q]pyrrolo[3,4-n][1,7,4,10,19]dioxatriazacycloheneicosine-23,25(24H)-dione (Compound 18)

2-(2-chloroethoxy)ethanol Compound 7f (0.35 mL, 3.30 mmol) was added to a mixture of Compound 1d (133 mg, 85% pure, 0.33 mmol) and Cs$_2$CO$_3$ (1.07 g, 3.30 mmol) in DMF (1.5 mL). The mixture was stirred at 100° C. for 2.5 h, cooled to 20° C., diluted with EtOAc and filtered through Celite. The solvents were removed under reduced pressure, and the desired diol Compound 8a was isolated (87 mg, 51%) by column chromatography (eluting with MeOH/CH$_2$Cl$_2$) as an orange solid: $^1$H NMR (300 MHz, CD$_3$OD) δ 8.19 (d, J=4.3 Hz, 2H), 8.01 (s, 2H), 7.18 (d, J=7.7 Hz, 2H), 6.72 (dd, J=8.0, 4.7 Hz, 2H), 4.56 (t, J=4.8 Hz, 4H), 3.83 (t, J=4.8 Hz, 4H), 3.67 (t, J=4.4 Hz, 4H), 3.53 (t, J=3.8 Hz, 4H), 3.18 (s, 3H); MS (ES) m/z 520 (M+H$^+$). Triethylamine (0.47 mL, 3.35 mmol) and MsCl (0.13 mL, 1.67 mmol) were added to a solution of the diol Compound 8a (87 mg, 0.167 mmol) in CH$_2$Cl$_2$ (1.5 mL) at 0° C. After stirring at 20° C. for 15 min, the mixture was quenched with water (0.5 mL) and then diluted with CH$_2$Cl$_2$ (5 mL). After the layers were separated, the aqueous phase was extracted with CH$_2$Cl$_2$ (3×5 mL) and the organic layers were combined, dried (Na$_2$SO$_4$) and concentrated. Purification with column chromatography (eluting with MeOH/CH$_2$Cl$_2$) gave the bismesylate Compound 8b (113 mg, 100%) as an orange solid: $^1$H NMR (400 MHz, CDCl$_3$) δ 8.21 (dd, J=4.7, 1.4 Hz, 2H), 7.94 (s, 2H), 7.23 (d, J=7.7 Hz, 2H), 6.76 (m, 2H), 4.55 (t, J=5.0 Hz, 4H), 4.28 (m, 4H), 3.88 (t, J=5.0 Hz, 4H), 3.67 (m, 4H), 3.18 (s, 3H), 2.90 (s, 6H); MS (ES) m/z 698 (M+Na).

I-Pr$_2$NEt Compound 8d (0.44 mL, 2.51 mmol) and H$_2$NEt Compound 8c in THF (2 M, 0.84 mmol) were added to a solution of Compound 8b (113 mg, 0.167 mmol) in DMF (17 mL). The mixture was stirred at 80° C. for 2 h and additional portions of the i-Pr$_2$NEt Compound 8d (0.2 mL, 1.25 mmol) and H$_2$NEt Compound 8c (0.42 mmol) were added. After the stirring was continued for 20 h, the mixture was cooled to 20° C. and concentrated under reduced pressure. The crude product was purified by column chromatography (eluting with MeOH/CH$_2$Cl$_2$) to give Compound 8e (59 mg, 67%) as an orange solid: $^1$H NMR (400 MHz, CD$_3$OD) δ 8.27 (dd, J=4.7, 1.5 Hz, 2H), 7.82 (s, 2H), 7.58 (dd, J=8.0, 1.5 Hz, 2H), 7.04 (dd, J=8.0, 4.8 Hz, 2H), 4.47 (t, J=4.8 Hz, 4H), 3.69 (t, J=4.8 Hz, 4H), 3.24 (t, J=5.0 Hz, 4H), 3.14 (s, 3H), 2.51 (d, J=6.1 Hz, 2H), 2.42 (s, br, 4H), 0.96 (t, J=7.1 Hz, 3H); MS (ES) m/z 529 (M+H$^+$). A mixture of Compound 8e (59 mg, 0.11 mmol), ethanol (4.2 mL) and KOH (196 mg, 3.50 mmol) was heated under reflux for 22 h. The mixture was concentrated under reduced pressure and the resulting residue was dissolved in water (10 mL) and acidified with 10% citric acid (pH 5). The mixture was stirred at 20° C. for 10 min and then concentrated. The resulting residue was mixed with ammonium acetate solids (10.0 g, 0.13 mol) and heated to 140° C. for 3 h. The mixture was then cooled to 20° C., diluted with water, made basic with 20% aqueous NaOH to achieve a pH of 10 and extracted with EtOAc (3×30 mL). The combined organic extracts were washed with water and brine, then dried (Na$_2$SO$_4$) and concentrated. Purification with column chromatography (eluting with MeOH/CH$_2$Cl$_2$/NH$_4$OH) yielded Compound 18 (6 mg, 11%) as an orange solid: $^1$H NMR (300 MHz, CD$_3$OD) 8.27 (dd, J=4.8, 1.7 Hz, 2H), 7.80 (s, 2H), 7.58 (dd, J=7.9, 1.5 Hz, 2H), 7.03 (dd, J=8.0, 4.8 Hz, 2H), 4.45 (t, J=4.7 Hz, 4H), 3.68 (t, J=4.7 Hz, 4H), 3.23 (t, J=5.0 Hz, 4H), 2.51 (q, J=7.2 Hz, 2H), 2.40 (t, J=5.1 Hz, 4H), 0.96 (t, J=7.2 Hz, 3H); MS (ES) m/z 515 (M+H$^+$).

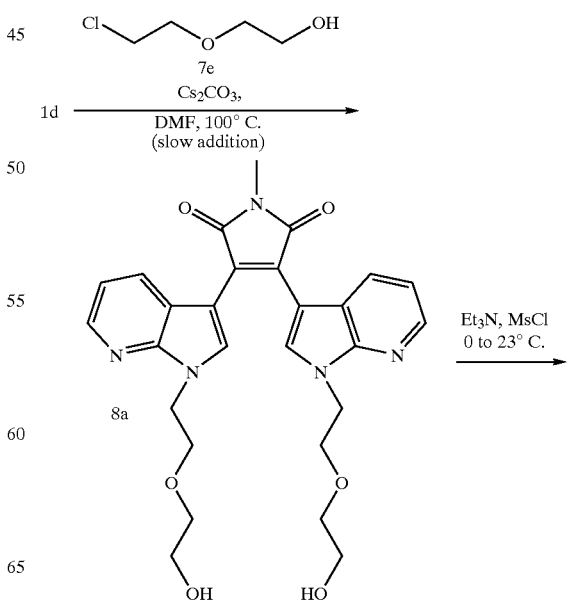

67
-continued

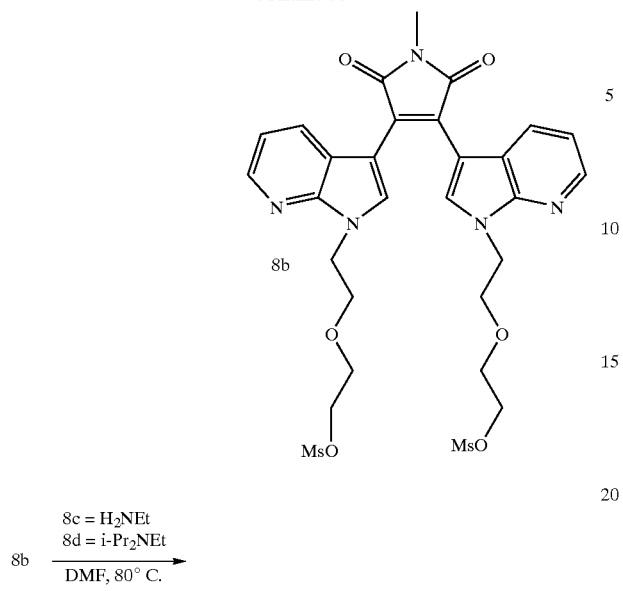

8b

8c = H₂NEt
8d = i-Pr₂NEt

8b $\xrightarrow{\text{DMF, 80° C.}}$

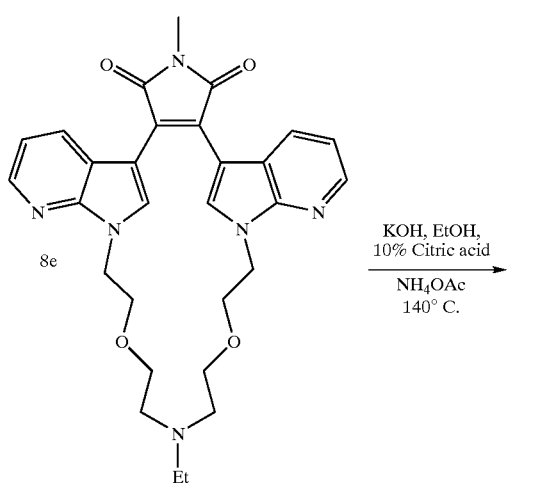

8e $\xrightarrow[\substack{\text{NH}_4\text{OAc} \\ 140° \text{ C.}}]{\text{KOH, EtOH,} \\ 10\% \text{ Citric acid}}$

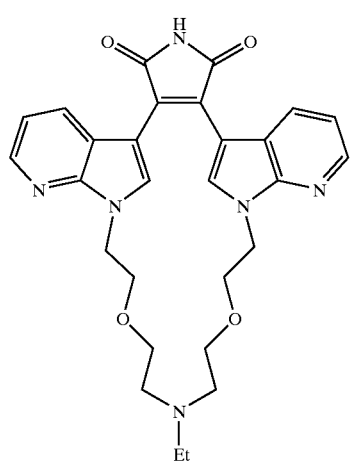

Cpd 18

68

Example 9

Compound 19

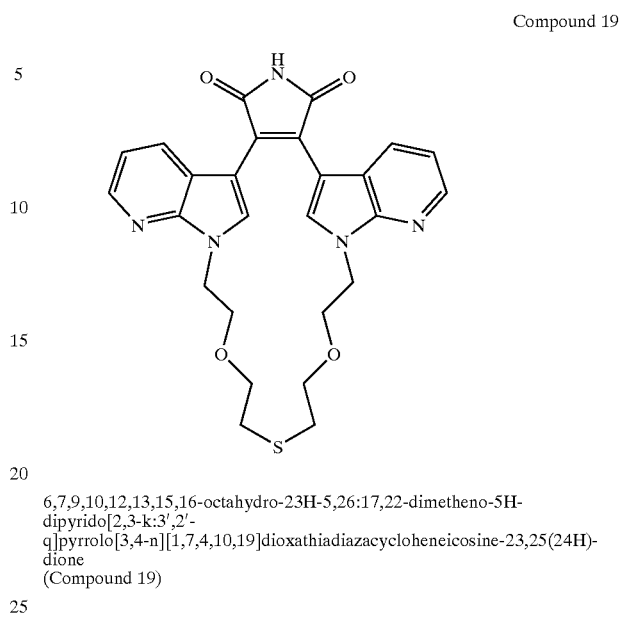

6,7,9,10,12,13,15,16-octahydro-23H-5,26:17,22-dimetheno-5H-dipyrido[2,3-k:3',2'-q]pyrrolo[3,4-n][1,7,4,10,19]dioxathiadiazacycloheneicosine-23,25(24H)-dione
(Compound 19)

The 2-bromoethylether Compound 5f (0.2 mL, 1.57 mmol) was added to a mixture of Compound 1d (54 mg, 0.16 mmol), Cs₂CO₃ (205 mg, 0.63 mmol) and DMF (5.0 mL). After heating at 40° C. for 1.5 h, the mixture was stirred at 20° C. for 12 h, then filtered through Celite and diluted with EtOAc. The organic layer was washed with water (3×5 mL), dried (Na₂SO₄) and concentrated. Purification by column chromatography (eluting with EtOAc/Hexane) provided Compound 9a as an orange solid (37 mg, 44%): ¹H NMR (300 MHz, CD₃OD) δ 8.13 (dd, J=4.7, 1.4 Hz, 2H), 8.06 (s, 2H), 7.20 (dd, J=8.0, 1.4 Hz, 2H), 6.74 (dd, J=8.0, 4.8 Hz, 2H), 4.53 (t, J=5.0 Hz, 4H), 3.87 (t, J=5.0 Hz, 4H), 3.71 (t, J=5.8 Hz, 4H), 3.42 (t, J=6.0 Hz, 4H), 3.14 (s, 3H); MS (ES) m/z 646 (M+H⁺). A mixture of the dibromide Compound 9a (37 mg, 0.057 mmol), anhydrous EtOH (240 mL) and sodium disulfide nonahydrate (14 mg, 0.057 mmol) was heated under reflux for 66 h. After removing the solvent, the residue was taken up in EtOAc. The organic layer was washed with 5% aqueous NaOH (3×5 mL), dried (Na₂SO₄) and concentrated. The residue was purified by column chromatography (eluting with Acetone/CH₂Cl₂), providing a mixture of Compound 9a (12 mg) and Compound 9b (12 mg, 60%) as an orange solid: ¹H NMR (300 MHz, CD₃OD) δ 8.27 (dd, J=4.8, 1.5 Hz, 2H), 7.84 (s, 2H), 7.53 (dd, J=4.8, 1.5 Hz, 2H), 7.03 (dd, J=8.0, 4.7 Hz, 2H), 4.45 (t, J=4.7 Hz, 4H), 3.70 (t, J=4.7 Hz, 4H), 3.35 (t, J=5.6 Hz, 4H), 3.14 (s, 3H), 2.34 (t, J=5.5 Hz, 4H); MS (ES) m/z 518 (M+H⁺). A mixture of Compound 9b (12 mg, 0.023 mmol), ethanol (2.0 mL) and KOH (188 mg, 3.30 mmol) was heated under reflux for 18 h. The mixture was concentrated under reduced pressure and the resulting residue was dissolved in water (3.0 mL) and acidified with 10% citric acid (pH 5–6). The mixture was stirred at 20° C. for 10 min and concentrated. The resulting residue was mixed with ammonium acetate solids (2.0 g, 26.0 mmol), and heated to 140° C. for 3 h. The mixture was cooled to 20° C., diluted with water (3.0 mL), made basic with 20% aqueous NaOH to achieve a pH of 10 and extracted with EtOAc (3×15 mL). The combined organic layers were washed with water and brine, then dried (Na₂SO₄) and concentrated. Purification with column chromatography (eluting with Acetone/CH₂Cl₂) provided Compound 9b (6 mg, 73%) as an orange solid: ¹H NMR (300 MHz, CD₃OD) δ 8.25 (dd, J=4.8, 1.5 Hz, 2H), 7.82 (s, 2H), 7.52 (dd, J=4.8, 1.5 Hz, 2H), 7.03 (dd, J=8.0, 4.8 Hz, 2H), 4.45 (t, J=4.5 Hz, 4H), 3.70 (t, J=4.5 Hz, 4H), 3.35 (t, J=5.5 Hz, 4H), 2.34 (t, J=5.5 Hz, 4H); MS (ES) m/z 504 (M+H⁺).

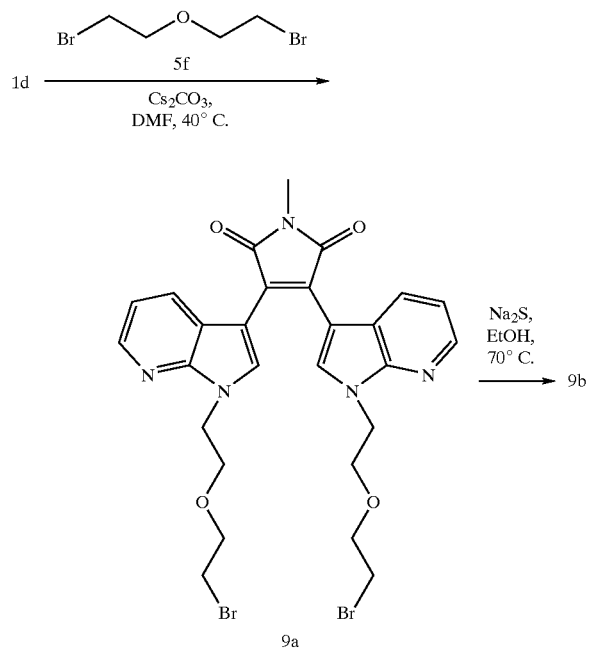

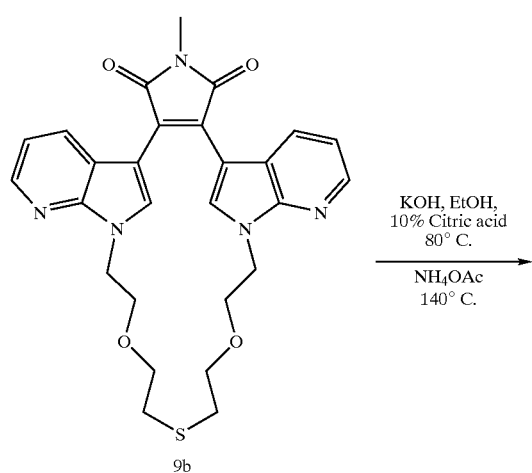

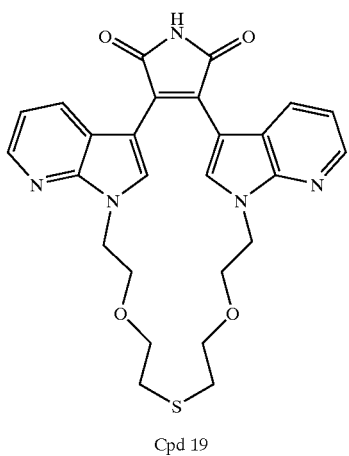

Example 10

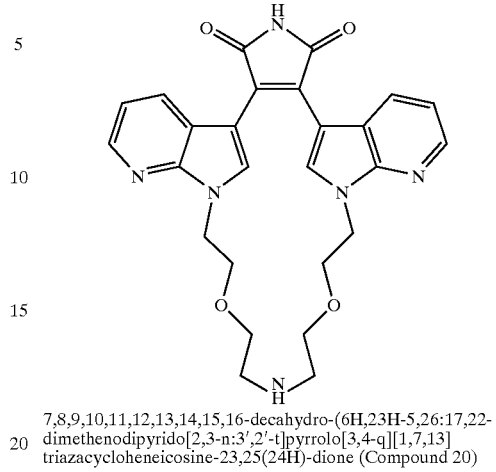

Compound 20

7,8,9,10,11,12,13,14,15,16-decahydro-(6H,23H-5,26:17,22-dimethenodipyrido[2,3-n:3′,2′-t]pyrrolo[3,4-q][1,7,13]triazacycloheneicosine-23,25(24H)-dione (Compound 20)

Pyridine (1.2 mL, 14.6 mmol) and MsCl (1.1 mL, 14.6 mmol) were added at 0° C. to a solution of a carbamate diol Compound 10a (1.06 g, 3.66 mmol, prepared as described in MaGee, D. I and Beck, E. J., *Can. J. Chem.*, 2000, 78, 1060–1066) in CH₂Cl₂ (13 mL). The mixture was stirred at 20° C. for 1.5 h, diluted with diethyl ether (10 mL) and washed sequentially with cold aqueous HCl (5%), NaOH (5%), water and brine. The organic solution was dried (MgSO₄), filtered and concentrated. Purification by column chromatographing on silica gel (eluting with Hexane/EtOAc) provided Compound 10b as a colorless oil (1.20 g, 74%): ¹H NMR (400 MHz, CDCl₃) δ 4.23 (t, J=6.4 Hz, 4H), 3.16 (s, br, 4H), 3.01 (s, 6H), 1.78 (m, 4H), 1.55 (m, 4H), 1.45 (s, 9H), 1.40 (m, 4H); MS (ES) m/z 468 (M+Na). A mixture of Compound 1d (50 mg, 85% pure, 0.12 mmol) and Cs₂CO₃ (190 mg, 0.58 mmol) in DMF (20 mL) was heated to 100° C. A DMF solution (5 mL) of the bismesylate Compound 10b (77 mg, 0.17 mmol) was added via syringe pump over 1.5 h. After the addition was complete, the mixture was stirred at 20° C. for 21 h, quenched with aqueous ammonium chloride (30 mL) and extracted with CH₂Cl₂ (2×30 mL). The organic phases were separated, combined, and washed with water (3×20 mL) and brine (15 mL). The crude product was then dried (Na₂SO₄), concentrated and chromatographed on silica gel column (eluting with Hexane/EtOAc) to give Compound 10c (36 mg, 50%) as an orange solid: ¹H NMR (300 MHz, CD₃OD) δ 8.29 (dd, J=4.7, 1.5 Hz, 2H), 7.66 (s, br, 2H), 7.58 (s, 2H), 7.05 (dd, J=8.0, 4.7 Hz, 2H), 4.30 (t, J=6.5 Hz, 4H), 3.15 (s, 3H), 2.73 (s, br, 4H), 1.75 (t, J=6.6 Hz, 4H), 1.42 (s, 9H), 1.34 (m, 4H), 1.03 (m, 4H); MS (ES) m/z 597 (M+H⁺).

TFA (0.2 mL) was added to a solution of Compound 10c (13 mg, 0.022 mmol) in CH₂Cl₂ (1.0 mL). After the mixture was stirred at 20° C. for 1 h, solvent and excess TFA were removed under reduced pressure. Ammonium hydroxide was carefully added and the orange solids were crushed out, collected by filtration and washed with water. Compound 10d (10 mg, 100%) was obtained after drying under vacuum: ¹H NMR (300 MHz, CD₃OD) δ 8.27 (dd, J=4.7, 1.4 Hz, 2H), 7.66 (s, 2H), 7.56 (dd, J=8.0, 1.4 Hz, 2H), 7.02 (dd, J=8.0, 4.8 Hz, 2H), 4.33 (t, J=5.9 Hz, 4H), 3.14 (s, 3H), 2.26 (t, J=6.5 Hz, 4H), 1.84 (m, 4H), 1.40 (m, 4H), 0.96 (m, 4H); MS (ES) m/z 497 (M+H⁺). A mixture of Compound 10d (10 mg, 0.020 mmol), ethanol (2.0 mL) and KOH (198 mg, 3.53 mmol) was heated under reflux for 18 h, then cooled to 20° C. and concentrated under reduced pressure. The residue was dissolved in water (3.0 mL) and acidified with 10% citric acid (pH 4). The mixture was stirred at 20° C. for 10 min, and concentrated. The resulting residue was mixed with ammonium acetate solids (2.4 g, 31.2 mmol), and heated to 140° C. for 3 h. The mixture was cooled to 20° C., diluted with water (3.0 mL), made basic with 20% aqueous NaOH to achieve a pH of 10 and extracted with EtOAc (3×25 mL). The combined organic layers were dried (Na$_2$SO$_4$) and concentrated. Purification by column chromatography (eluting with MeOH/CH$_2$Cl$_2$) gave Compound 20 (4 mg, 42%) as an orange solid: $^1$H NMR (300 MHz, CD$_3$OD) δ 8.27 (dd, J=4.7, 1.5 Hz, 2H), 7.65 (s, 2H), 7.55 (dd, J=8.0, 1.5 Hz, 2H), 7.01 (dd, J=8.0, 4.8 Hz, 2H), 4.32 (t, J=5.9 Hz, 4H), 2.23 (t, J=6.3 Hz, 4H), 1.81 (t, J=5.9 Hz, 4H), 1.40 (m, 4H), 0.94 (t, J=7.5 Hz, 4H); MS (ES) m/z 483 (M+H$^+$).

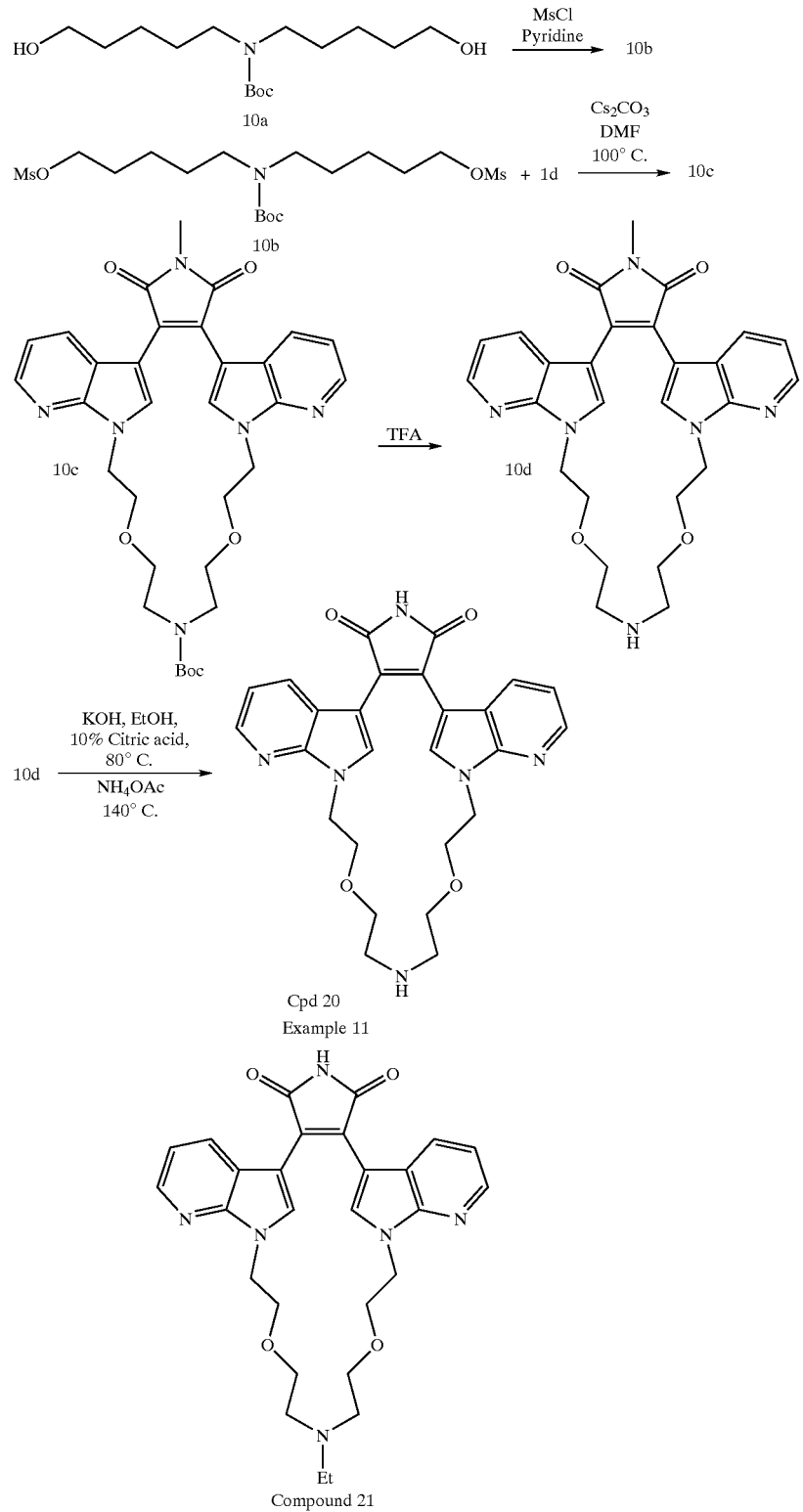

11-ethyl-7,8,9,10,11,12,13,14,15,16-decahydro-6H,23H-5,26:17,22-dimethen odipyrido[2,3-n:3',2'-t]pyrrolo[3,4-q][1,7,13]triazacycloheneicosine-23,25(24H)-dione (Compound 21)

Example 11

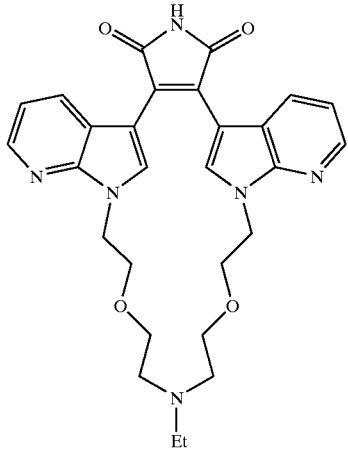

Compound 21

11-ethyl-7,8,9,10,11,12,13,14,15,16-decahydro-6H,23H-5,26:17,22-dimethenodipyrido[2,3-n:3′,2′-t]pyrrolo[3,4-q][1,7,13]triazacycloheneicosine-23,25(24H)-dione (Compound 21)

A mixture of Compound 10d (14 mg, 0.028 mmol), THF (1.0 mL) and iodoethane (4 μL, 0.063 mmol) was heated to reflux for two days. The product was concentrated and chromatographed (eluting with MeOH/CH$_2$Cl$_2$/NH$_4$OH) to give Compound 11a (12 mg, 75%) as an orange solid: $^1$H NMR (400 MHz, CD$_3$OD) δ 8.27 (dd, J=4.7, 1.6 Hz, 2H), 7.64 (s, 2H), 7.62 (dd, J=8.0, 1.6 Hz, 2H), 7.03 (dd, J=8.0, 4.7 Hz, 2H), 4.31 (m, 4H), 3.14 (s, 3H), 2.44 (m, 2H), 2.11 (m, 4H), 1.84 (m, 4H), 1.25 (m, 4H), 7H); MS (ES) m/z 525 (M+H$^+$). Compound 11a (12 mg, 0.023 mmol) was transformed into Compound 21 (6 mg, 50%) using the procedure described for obtaining Compound 20. Compound 21 was isolated as an orange solid: $^1$H NMR (400 MHz, CD$_3$OD) δ 8.27 (dd, J=4.7, 1.4 Hz, 2H), 7.62 (s, 2H), 7.60 (dd, J=7.7, 1.5 Hz, 2H), 7.03 (dd, J=8.0, 4.7 Hz, 2H), 4.30 (m, 4H), 2.44 (q, J=7.1 Hz, 2H), 2.11 (m, 4H), 1.83 (m, 4), 1.26 (m, 4H), 0.98 (m, 7H); MS (ES) m/z 511 (M+H$^+$).

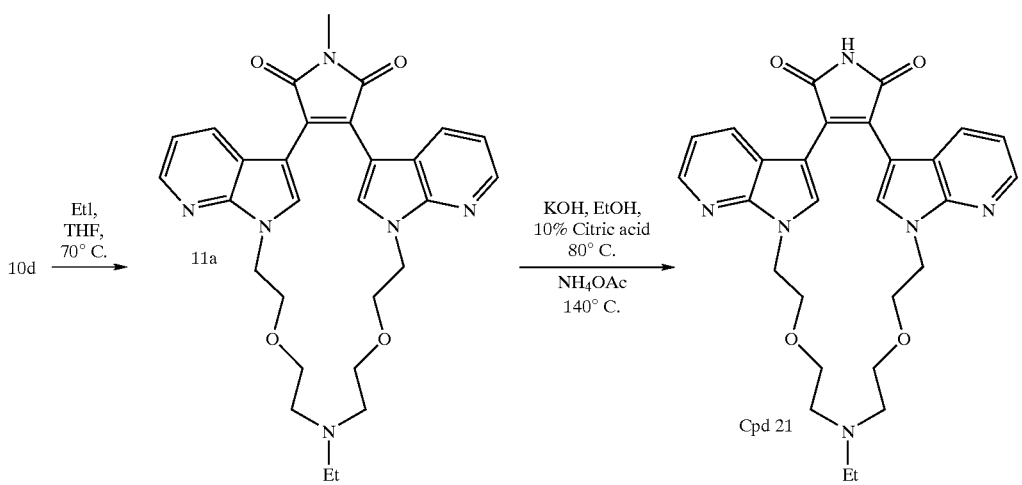

Example 12

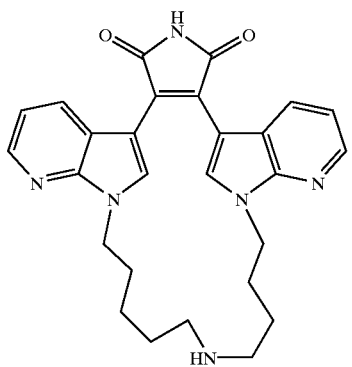

Compound 22

6,7,8,9,10,11,12,13,14,15-decahydro-22H-5,25:16,21-dimetheno-5H-dipyrido [2,3-m:3′,2′-s]pyrrolo[3,4-p][1,6,12]triazacycloheneicosine-22,24(23H)-dione (Compound 22)

A mixture of 2,3-dichloromaleic anhydride Compound 12a (1.02 g, 6.10 mmol),

Example 12

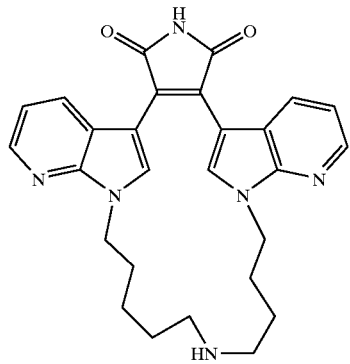

Compound 22

6,7,8,9,10,11,12,13,14,15-decahydro-22H-5,25:16,21-dimetheno-5H-dipyrido[2,3-m:3′,2′-s]pyrrolo[3,4-p][1,6,12]triazacycloheneicosine-22,24(23H)-dione (Compound 22)
A mixture of 2,3-dichloromaleic anhydride Compound 12a (1.02 g, 6.10 mmol), A mixture of 2,3-dichloromaleic anhydride Compound 12a (1.02 g, 6.10 mmol), 2,4-dimethoxybenzylic amine Compound 12b (1.02 g, 6.10 mmol) in glacial acetic acid (18 mL) was heated to 80° C. for 5 h. The mixture was cooled to 20° C., concentrated under reduced pressure and diluted with CH$_2$Cl$_2$ (50 mL). The mixture was sequentially washed with water (15 mL) and 2 M aqueous Na$_2$CO$_3$ (15 mL), then water (15 mL) and brine (15 mL). After the combined organic phases were concentrated, the residue was filtered through a short pad of SiO$_2$ (eluting with CH$_2$Cl$_2$) to give Compound 12c (1.42 g, 74%) as a light brown solid: $^1$H NMR (300 MHz, CDCl$_3$) δ 7.20 (d, J=8.7 Hz, 1H), 6.44 (d, J=2.3 Hz, 1H), 6.42 (s, 1H), 4.72 (s, 2H), 3.79 (s, 3H), 3.78 (s, 3H). A mixture of Compound 11b (500 mg, 1.31 mmol), Compound 12c (180 mg, 0.57 mmol), PdCl$_2$(PPh$_3$)$_2$ (80 mg, 0.111 mmol) and LiCl (240 mg, 8.6 mmol) in toluene (9.0 mL) was heated at 100° C. for 20 h. After the solvent was removed under reduced pressure, the residue was dry-loaded on silica gel (eluting with EtOAc/Hexane) to give Compound 12d (160 mg, 58%) as an orange red solid: $^1$H NMR (300 MHz, DMSO-d$_6$) δ 12.30 (s, 2H), 8.12 (d, J=4.6 Hz, 2H), 7.93 (d, J=2.8 Hz, 2H), 7.08 (m, 3H), 6.73 (dd, J=8.0, 4.7 Hz, 2H), 6.58 (d, J=2.1 Hz, 1H), 6.48 (d, J=8.4 Hz, 1H), 4.68 (s, 2H), 3.82 (s, 3H), 3.74 (s, 3H); MS (ES) m/z 480 (M+H$^+$).

A mixture of δ-valerolactone Compound 12e (1.7 mL, 18.3 mmol) and 4-amino-1-butanol Compound 12f (1.7 mL, 18.3 mmol) in m-xylene (50 mL) was heated to 120° C. for 20 h. The mixture was cooled to 20° C. and the lower layer was separated from the upper xylene layer and concentrated under reduced pressure to give a crude product Compound 12g (3.50 g, 99%). A solution of the crude Compound 12g (1.91 g, 10.1 mmol) in THF (50 mL) was heated to reflux. A borane dimethylsulfide complex (2 M in THF, 40.0 mmol) was added dropwise via addition funnel. After the addition was complete, the mixture was refluxed for another hour, then cooled to 20° C. and quenched with MeOH (4.0 mL). Hydrogen chloride (1 M in Et$_2$O, 12.0 mmol) was added. The mixture was then stirred at 20° C. for 10 min and concentrated under reduced pressure to give a crude diol salt Compound 12h. Compound 12h was then mixed with MeOH (40 mL), Et$_3$N (5.7 mL, 40.4 mmol) and Boc$_2$O (2.7 g, 12.1 mmol). The mixture was refluxed for 3 h, then cooled to 20° C., concentrated and taken up in CH$_2$Cl$_2$ (40 mL). The product was quickly washed with cold 1 N HCl, dried (Na$_2$SO$_4$) and concentrated. Purification by column chromatography (eluting with EtOAc) gave Compound 12i (1.90 g, 70%) as a colorless oil: $^1$H NMR (300 MHz, CDCl$_3$) δ 3.67 (m, 4H), 3.18 (m, 4H), 1.60 (m, 10H), 1.45 (s, 9H); MS (ES) m/z 298 (M+Na). A solution of Compound 12i (1.90 g, 6.91 mmol) in CH$_2$Cl$_2$ (20 mL) was cooled in an ice bath, then pyridine (2.2 mL, 27.6 mmol) was added, followed by MsCl (2.1 mL, 27.6 mmol). The mixture was stirred at 20° C. for 1.5 h, diluted with Et$_2$O (15 mL) and washed with cold 5% HCl and 5% NaOH. The organic phase was dried (Na$_2$SO$_4$) and concentrated. Purification by column chromatography on silica gel (eluting with Hexane/EtOAc) gave the bismesylate Compound 12j (2.40 g, 82%) as a colorless oil: $^1$H NMR (400 MHz, CDCl$_3$) δ 4.24 (m, 4H), 3.19 (m, 4H), 3.01 (s, 3H), 3.00 (s, 3H), 1.75 (m, 4H), 1.64 (m, 2H), 1.56 (m, 2H), 1.45 (s, 9H), 1.41 (m, 2H); MS (ES) m/z 454 (M+Na).

A mixture of Compound 12d (38 mg, 0.079 mmol) and Cs$_2$CO$_3$ (300 mg, 0.92 mmol) in DMF (12 mL) was heated to 70° C. A DMF solution (2 mL) of the bismesylate Compound 12j (60 mg, 0.14 mmol) was added via syringe pump over 1 h. After the addition was complete, the mixture was stirred at 70° C. for 22 h, cooled to 20° C., quenched with saturated aqueous ammonium chloride (30 mL) and diluted with EtOAc (50 mL). The organic phase was separated, washed with water (3×20 mL) and brine (15 mL). The crude product was then dried (Na$_2$SO$_4$), concentrated and chromatographed on a silica gel column (eluting with Hexane/EtOAc) to give Compound 12k (27 mg, 48%) as an orange solid: $^1$H NMR (400 MHz, CDCl$_3$) δ 8.40 (dd, J=4.8, 1.5 Hz, 2H), 8.29 (m, 2H), 7.78 (s, 1H), 7.18 (dd, J=8.0, 4.7 Hz, 2H), 7.10 (s, 1H), 6.85 (m, 1H), 6.46 (s, 1H), 6.43 (d, J=2.4 Hz, 1H), 4.85 (s, 2H), 4.44 (m, 2H), 4.14 (m, 2H), 3.86 (s, 3H), 3.78 (s, 3H), 3.18 (m, 2H), 2.90 (m, 2H), 2.56 (m, 2H), 1.90 (m, 2H), 1.64 (m, 2H), 1.39 (s, 9H), 1.13 (m, 2H), 0.74 (m, 2H); MS (ES) m/z 719 (M+H$^+$). TFA (1.0 mL) was added to a solution of Compound 12k (27 mg, 0.037 mmol) in CH$_2$Cl$_2$ (2 mL). The mixture was stirred at 20° C. for 30 min. Ammonium hydroxide was carefully added to adjust the pH of the mixture to 10. After extraction with EtOAc (3×10 mL), the organic layers were combined, washed with water (10 mL) and brine (5 mL), then dried (Na$_2$SO$_4$) and concentrated to give Compound 12l (22 mg, 100%) as an orange solid: $^1$H NMR (300 MHz, CD$_3$OD) δ 8.27 (m, 2H), 7.77 (d, J=8.0 Hz, 1H), 7.68 (d, J=8.0 Hz, 1H), 7.61 (s, 1H), 7.52 (s, 1H), 7.13 (d, J=8.3 Hz, 1H), 7.07 (m, 2H), 6.53 (s, 1H), 6.45 (d, J=8.5 Hz, 1H), 4.77 (s, 2H), 4.26 (m, 4H), 3.84 (s, 3H), 3.83 (s, 3H), 2.44 (t, J=7.1 Hz, 2H), 2.15 (t, J=6.8 Hz, 2H), 1.78 (m, 4H), 1.31 (m, 2H), 1.20 (m, 2H), 1.01 (m, 2H); MS (ES) m/z 619 (M+H$^+$). Methanesulfonic acid (0.5 mL) was added to a solution of the Compound 12l (5 mg, 0.008 mmol) in CH$_2$Cl$_2$ (1.0 mL). The mixture was stirred at 20° C. for 6 h, then ammonium hydroxide was carefully added to make the mixture basic. The mixture was extracted with EtOAc (2×10 mL) and the organic layers were combined, washed with water (5 mL) and brine (5 mL), then dried (Na$_2$SO$_4$) and concentrated. The product was purified by column chromatography on silica gel (eluting with MeOH/CH$_2$Cl$_2$/NH$_4$OH) to give Compound 22 (5 mg, 100%) as an orange solid: $^1$H NMR (300 MHz, CDCl$_3$) δ 8.35 (m, 2H), 7.96 (d, J=7.9 Hz, 1H), 7.55 (s, 1H), 7.53 (d, J=8.1 Hz, 1H), 7.42 (s, 1H), 7.09 (dd, J=8.0, 4.7 Hz, 1H), 6.97 (dd, J=8.0, 4.7 Hz, 1H), 4.33 (t, J=6.0 Hz, 2H), 4.22 (t, J=6.6 Hz, 2H), 2.45 (t, J=6.4 Hz, 2H), 2.32 (t, J=6.3 Hz, 2H), 1.87 (m, 2H), 1.73 (m, 2H), 1.35 (m, 2H), 1.25 (m, 2H), 1.13 (m, 2H); MS (ES) m/z 469 (M+H$^+$).

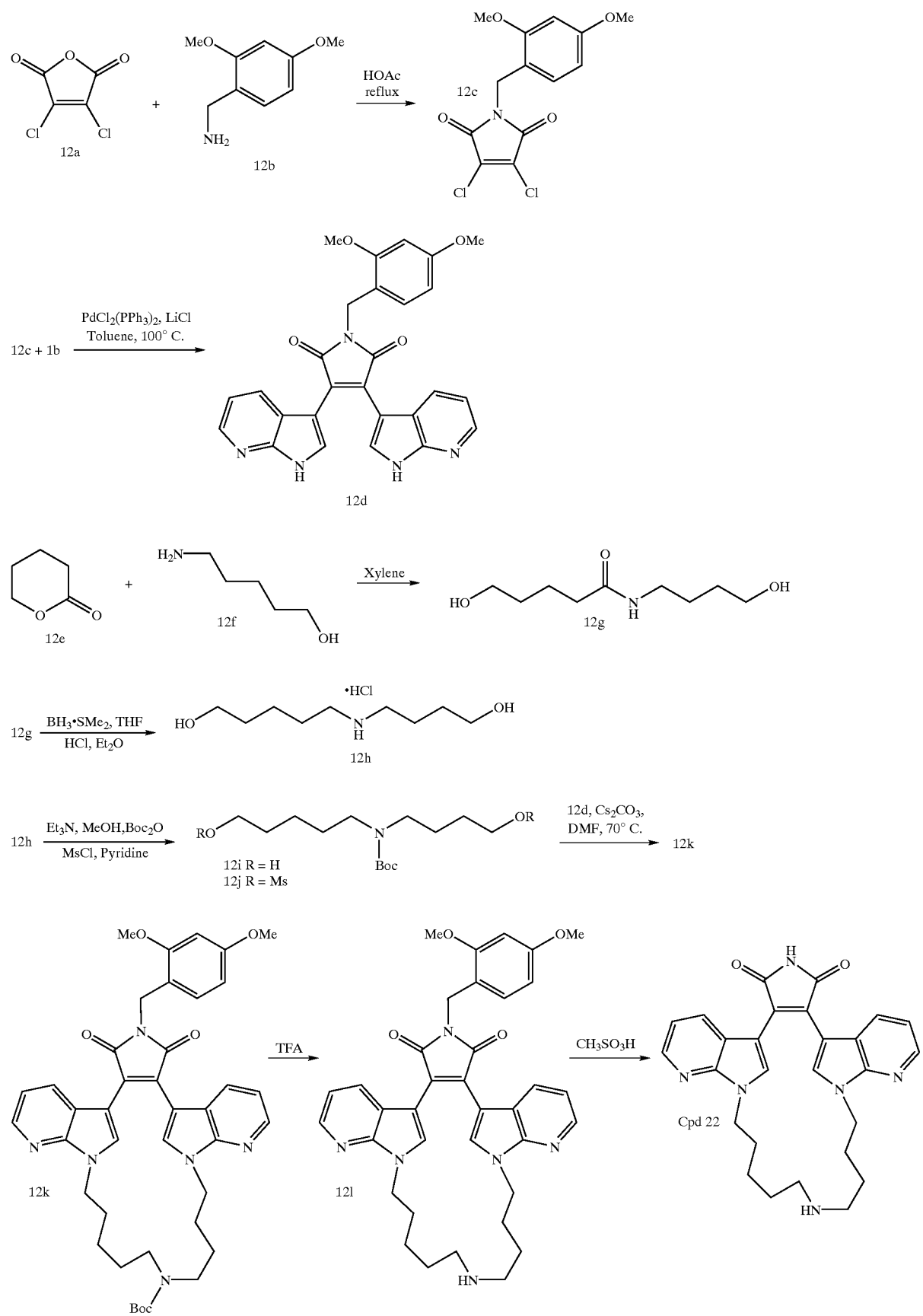

Example 13

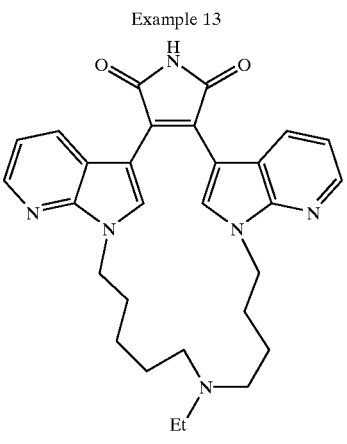

Compound 23

10-ethyl-6,7,8,9,10,11,12,13,14,15-decahydro-22H-5,25:16,21-dimetheno-5H -dipyrido[2,3-m:3',2' s]pyrrolo[3,4-p][1,6,12]triazacycloeicosine-22,24(23H)-dione (Compoun d 23)

Example 13

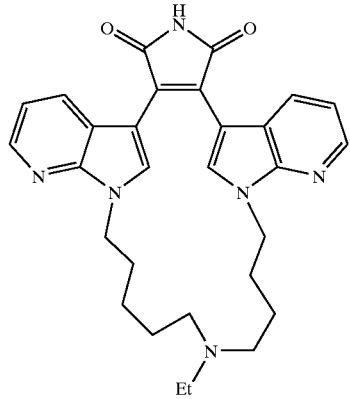

Compound 23

10-ethyl-6,7,8,9,10,11,12,13,14,15-decahydro-22H-5,25:16,21-dimetheno-5H-dipyrido[2,3-m:3',2'-s]pyrrolo[3,4-p][1,6,12]triazacycloeicosine-22,24(23H)-dione (Compound 23)

A mixture of Compound 121 (17 mg, 0.027 mmol), THF (0.8 mL) and iodoethane (5 μL, 0.062 mmol) was refluxed for two days, then cooled and concentrated under reduced pressure. The product was purified by column chromatography (eluting with MeOH/CH$_2$Cl$_2$) to give Compound 13a (6 mg, 35%) as an orange solid: $^1$H NMR (400 MHz, CD$_3$OD) δ 8.32 (dd, J=4.7, 1.5 Hz, 1H), 8.25 (m, 2H), 7.85 (s, 1H), 7.32 (s, 1H), 7.27 (d, J=7.8 Hz, 1H), 7.22 (dd, J=8.0, 4.8 Hz, 1H), 7.14 (d, J=8.4 Hz, 1H), 6.93 (dd, J=8.0, 4.8 Hz, 1H), 6.54 (d, J=2.3 Hz, 1H), 6.46 (dd, J=8.4, 2.3 Hz, 1H), 4.79 (s, 2H), 4.45 (m, 2H), 4.15 (m, 2H), 3.84 (s, 3H), 3.77 (s, 3H), 2.83 (m, 4H), 2.27 (m, 2H), 1.99 (m, 2H), 1.65 (t, J=6.4 Hz, 2H), 1.27 (m, 4H), 1.15 (m, 2H), 0.88 (t, J=7.3 Hz, 3H); MS (ES) m/z 647 (M+H$^+$). Methanesulfonic acid (0.2 mL) was added to a solution of Compound 13a (6 mg, 0.009 mmol) in CH$_2$Cl$_2$ (1.0 mL). After the mixture was stirred at 20° C. for 2 h, ammonium hydroxide was carefully added to make the mixture basic. The mixture was then extracted with EtOAc (2×10 mL) and the organic layers were combined, washed with water (5 mL) and brine (5 mL), then dried (Na$_2$SO$_4$) and concentrated. The product was purified by column chromatography on silica gel (eluting with MeOH/ CH$_2$Cl$_2$/NH$_4$OH) to give Compound 23 (4 mg, 90%) as an orange solid: $^1$H NMR (300 MHz, CDCl$_3$) δ 8.35 (m, 2H), 7.90 (m, 1H), 7.71 (m, 1H), 7.54 (s, 1H), 7.35 (s, 1H), 7.07 (dd, J=7.8, 4.9 Hz, 1H), 7.00 (dd, J=7.3, 4.7 Hz, 1H), 4.24 (m, 4H), 2.37 (m, 2H), 2.30 (m, 2H), 2.04 (m, 2H), 1.73 (t, J=6.2 Hz, 4H), 1.24 (m, 4H), 0.95–1.02 (m, 5H); MS (ES) m/z 497 (M+H$^+$).

-continued

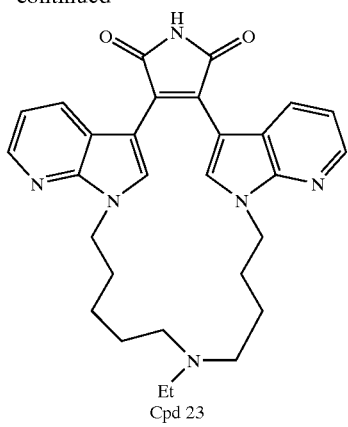

Cpd 23

Example 14

Compound 24

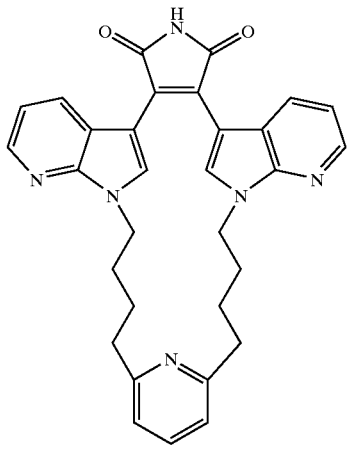

7,8,9,15,16,17,18-heptahydro-6H,25H-5,28:19,24-dimetheno-10,14-nitrilodipyrido[2,3-b:3′,2′-h]pyrrolo[3,4-e][1,10]diazacyclotricosine-25,27(26H)-dione(Compound 24)

BuLi (1.6 M in hexane, 10.3 mmol) at −78° C. was added to a solution of 2,6-lutidine Compound 14a (0.5 mL, 4.30 mmol) in THF (15 mL). The deep red solution was kept stirring at −78° C. for 30 min, then 3-bromo-propoxy-tert-butyldimethylsilane Compound 14b (2.4 mL, 10.3 mmol) was added. The mixture was warmed to ambient temperature for 18 h, quenched with water (2 ml) and concentrated under reduced pressure. The residue was diluted with water (115 mL) and extracted with hexane (3×20 mL). The organic extracts were combined, dried ($Na_2SO_4$) and concentrated. Purification by column chromatography (eluting with hexane/EtOAc) gave Compound 14c (0.55 g, 30%) as a colorless oil: $^1$H NMR (300 MHz, $CDCl_3$) δ 7.45 (m, 1H), 6.91 (m, 2H), 3.59 (t, J=6.4 Hz, 4H), 2.73 (m, 4H), 1.70 (m, 4H), 1.57 (m, 4H), 0.85 (s, 18H), 0.00 (s, 12H); MS (ES) m/z 452 (M+H$^+$). TBAF (1 M in THF, 2.60 mmol) was added to a mixture of Compound 14c (0.55 g, 1.20 mmol) in THF (3.0 mL). The mixture was stirred at 20° C. for 3 h, then concentrated under reduced pressure. Purification by chromatography on silica gel (eluting with EtOAc (containing 5% $Et_3N$)) gave Compound 14d (254 mg, 95%) as a colorless oil: $^1$H NMR (300 MHz, $CDCl_3$) δ 7.53 (t, J=7.6 Hz, 1H), 6.98 (d, J=7.6 Hz, 2H), 3.70 (t, J=6.0 Hz, 4), 2.83 (t, J=7.4 Hz, 4H), 1.85 (m, 4H), 1.64 (m, 4H); MS (ES) m/z 224 (M+H$^+$). Triethylamine (0.95 mL, 6.84 mmol) at 0° C. was added to a solution of the diol Compound 14d (254 mg, 1.14 mmol) in $CH_2Cl_2$ (4 mL), followed by MsCl (0.35 mL, 4.56 mmol). The mixture was stirred at 20° C. for 1.5 h, diluted with diethyl ether (20 mL) and washed with 5% HCl (5 mL). The layers were separated and the organic phase was discarded. The aqueous phase was diluted with $CH_2Cl_2$ (10 mL) and made basic with 5% NaOH (5 mL). The mixture was extracted with $CH_2Cl_2$ (3×20 mL) and the organic extracts were combined, washed with brine (10 mL), then dried ($Na_2SO_4$) and concentrated. Purification with chromatography (eluting with hexane/EtOAc) gave Compound 14e (162 mg, 38%) as a light brown liquid: MS (ES) ml/z 380 (M+H$^+$).

A mixture of Compound 1d (74 mg, 0.21 mmol), $Cs_2CO_3$ (290 mg, 0.89 mmol) and DMF (30 mL) was heated to 100° C. A solution of Compound 14e (100 mg, 0.26 mmol) in DMF (7 mL) was added via syringe pump over 2 h. After the addition was complete, the mixture was stirred at 20° C. for 18 h, then quenched with saturated ammonium chloride and extracted with ethyl acetate (3×50 mL). The organic extracts were combined, washed with water (3×30 mL) and brine (30 mL), then dried ($Na_2SO_4$) and concentrated. The residue was purified by column chromatography (eluting with acetone/methylene chloride) to recover Compound 14e (21 mg) and give Compound 14f (14 mg, 22%) as an orange solid: $^1$H NMR (300 MHz, $CD_3OD$) δ 8.14 (d, J=4.6 Hz, 1H), 7.54–7.73 (m, 8H), 6.97 (m, 2H), 4.30 (t, J=5.6 Hz, 4H), 3.14 (s, 3H), 2.65 (m, 4H), 1.73 (m, 4H), 1.31 (m, 4H); MS (ES) m/z 531 (M+H$^+$). A mixture of Compound 14f (14 mg, 0.026 mmol), KOH (360 mg, 6.43 mmol) and ethanol (3 mL) was refluxed for two days, cooled to 20° C. and then the solvent was removed under reduced pressure. The residue was dissolved in water (5 mL), made acidic with 10% citric acid, stirred at 20° C. for 10 min and extracted with methylene chloride (3×20 mL). The organic extracts were combined, dried ($Na_2SO_4$) and concentrated. The residue was mixed with ammonium acetate (2.5 g), heated to 140° C. for 3 h and cooled to 20° C. Water (10 mL) was added, then the solution was made basic with 20% aqueous NaOH and extracted with EtOAc (3×20 mL). The organic extracts were combined, washed with water (20 mL) and brine (10 mL), then dried ($Na_2SO_4$) and concentrated. The product was purified by column chromatography (eluting with acetone/$CH_2Cl_2$) to give Compound 24 (4 mg, 30%) as a yellow solid: $^1$H NMR (300 MHz, $CDCl_3$) δ 8.28 (d, J=4.0 Hz, 2H), 7.68 (m, 2H), 7.43–7.54 (m, 3H), 6.99 (dd, J=7.9, 4.7 Hz, 2H), 6.87 (d, J=7.4 Hz, 2H), 4.28 (t, J=6.2 Hz, 4H), 2.65 (m, 4H), 1.81 (m, 4H), 1.46 (m, 4H); MS (ES) m/z 517 (M+H$^+$).

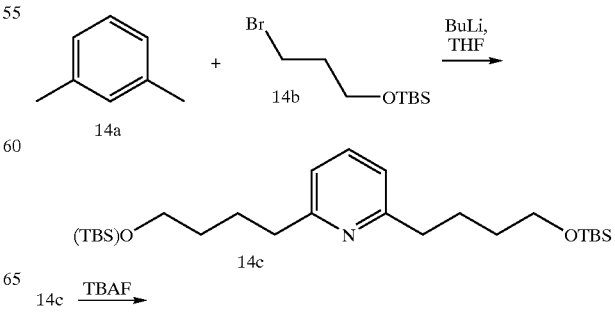

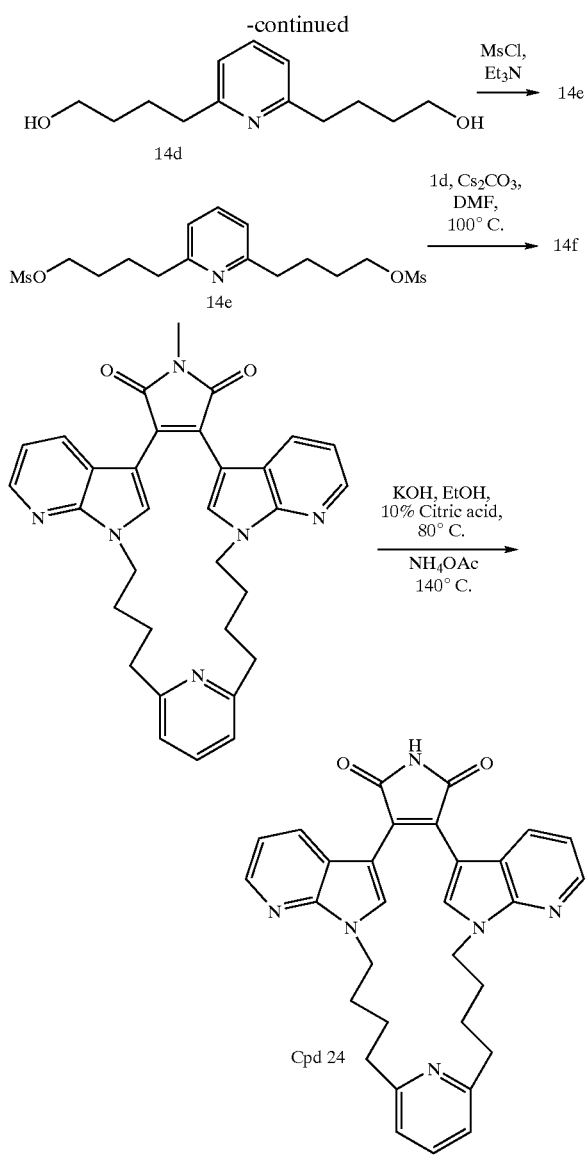

Example 15

Compound 25

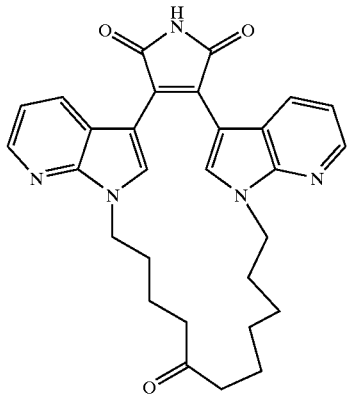

7,8,9,10,11,13,14,15,16-nonahydro-6H,23H-5,26:17,22-dimethenodipyrido[2,3-b:3',2'-h]pyrrolo[3,4-e][1,10]diazacycloheneicosine-12,23,25(24H)-trione (Compound 25)

A mixture of 4-oxo-1,9-nonanedicarboxylic acid Compound 15a (240 mg, 1.04 mmol), absolute ethanol (3.0 mL) and concentrated HCl (1.0 mL) was heated under reflux for 20 h. The mixture was cooled to 20° C., diluted with EtOAc (25 mL) and neutralized with saturated aqueous NaHCO$_3$. The organic layer was separated, washed with water (5 mL) and brine (5 mL), then dried (Na$_2$SO$_4$) and concentrated to give Compound 15b (270 mg, 91%) as colorless oil: $^1$H NMR (300 MHz, CDCl$_3$) δ 4.09–4.16 (m, 4H), 2.10–2.50 (m, 10H), 1.89 (q, J=7.0 Hz, 2H), 1.54–1.68 (m, 4H), 1.25 (t, J=7.1 Hz, 6H); MS (ES) m/z 309 (M+Na). A mixture of Compound 15b (270 mg, 0.94 mmol), ethylene glycol (0.24 mL, 4.30 mmol), triethyl orthoformate (0.48 mL, 2.89 mmol) and TsOH monohydrate (14 mg, 0.074 mmol) was refluxed for 45 min, cooled to 20° C., then diluted with saturated aqueous NaHCO$_3$ and extracted with diethyl ether (2×20 mL). The organic layers were combined, washed again with NaHCO$_3$, dried (Na$_2$SO$_4$) and concentrated to give Compound 15c (310 mg, 100%) as colorless oil: $^1$H NMR (300 MHz, CDCl$_3$) δ 4.08–4.16 (m, 4H), 3.92 (s, 4H), 2.26–2.33 (m, 4H), 1.58–1.72 (m, 8H), 1.30–1.35 (m, 4H), 1.25 (t, J=7.2 Hz, 6H); MS (ES) m/z 353 (M+Na). Compound 15c (330 mg, 0.94 mmol) in THF (5.0 mL) was added to a THF solution of LiAlH$_4$ (1.0 M, 1.50 mmol). After the mixture was stirred at 20° C. for 2 h, quenched with water and extracted with diethyl ether (3×20 mL), the organic layers were combined, dried (Na$_2$SO$_4$) and concentrated to give Compound 15d (210 mg, 91%) as a colorless liquid: $^1$H NMR (300 MHz, CDCl$_3$) δ 3.93 (s, 4H), 3.62–3.67 (m, 4H), 1.34–1.67 (m, 16H); MS (ES) m/z 269 (M+Na). A mixture of Compound 15d (210 mg, 0.85 mmol), water (3.4 mL), H$_2$SO$_4$ (6 M, 0.5 mL) and acetone (0.3 mL) was refluxed for 1.5 h. After the mixture was concentrated, the residue was extracted with CH$_2$Cl$_2$ (3×15 mL). The organic extracts were combined, dried (Na$_2$SO$_4$) and concentrated to give Compound 15e (121 mg, 71%) as a white solid: $^1$H NMR (400 MHz, CDCl$_3$) δ 3.64 (s, 2H), 3.63 (t, J=6.5 Hz, 4H), 2.39–2.46 (m, 4H), 1.25–1.78 (m, 12H); MS (ES) m/z (M+Na). Triethylamine (0.41 mL, 2.97 mmol) and MsCl (0.23 mL, 2.97 mmol) at 0° C. were added to a methylene chloride (2.5 mL) solution of Compound 15e (120 mg, 0.59 mmol). The mixture was stirred at 20° C. for 2 h and quenched with water. The layers were separated and the aqueous phase was extracted with CH$_2$Cl$_2$ (2×20 mL). The organic phases were combined, washed sequentially with 5 mL of 5% HCl, water and 5% NaHCO$_3$, then dried (Na$_2$SO$_4$) and concentrated to give Compound 15f (169 mg, 80%): $^1$H NMR (300 MHz, CDCl$_3$) δ 4.20–4.25 (m, 4H), 3.64 (m, 2H), 3.01 (s, 3H), 3.00 (s, 3H), 2.34–2.49 (m, 4H), 1.32–1.78 (m, 10H); MS (ES) m/z 381 (M+Na).

A mixture of Compound 1d (55 mg, 0.13 mmol), Cs$_2$CO$_3$ (370 mg, 1.13 mmol) and DMF (25 mL) was heated to 100° C. A DMF (5 mL) solution of Compound 15f (84 mg, 0.23 mmol) was added via syringe pump over 1.5 h. After the addition was complete, the mixture was stirred at 20° C. for 2 h, quenched with saturated ammonium chloride (30 mL) and extracted with methylene chloride (2×30 mL). The organic phases were combined, washed with water (3×20 mL) and brine (30 mL), then dried (Na$_2$SO$_4$) and concentrated. Purification by column chromatography (eluting with EtOAc/hexane) gave Compound 15g (11 mg, 16%) as an orange solid: $^1$H NMR (300 MHz, CD$_3$OD) δ 8.24–8.30 (ddd, J=6.0, 4.7, 1.2 Hz, 2H), 7.82–7.85 (dd, J=8.0, 1.3 Hz, 1H), 7.80 (s, 1H), 7.58 (s, 1H), 7.40 (dd, J=8.1, 1.3 Hz, 1H), 7.09 (dd, J=8.0, 4.7 Hz, 1H), 6.96 (dd, J=8.1, 4.8 Hz, 1H), 4.34 (t, J=5.8 Hz, 2H), 4.20 (t, J=6.2 Hz, 2H), 3.14 (s, 3H), 2.32 (t, J=7.1 Hz, 2H), 2.11 (t, J=6.8 Hz, 2H), 1.69–1.84 (m, 4H), 1.37–1.41 (m, 2H), 1.18–1.31 (m, 2H), 1.07–1.16 (m, 2H), 0.90–1.04 (m, 2H); MS (ES) m/z 510 (M+H$^+$). Compound 15g (12 mg, 0.023 mmol) was converted into Compound 25 (2 mg, 10%) using the procedure described for preparing Compound 24. $^1$H NMR (300 MHz, CDCl$_3$) δ 8.37 (d, J=5.0 Hz, 1H), 8.32 (d, J=4.6 Hz, 1H), 7.84 (d, J=8.0 Hz, 1H), 7.70 (s, 1H), 7.49 (s, 1H), 7.42 (m, 1H), 7.08 (dd, J=8.0, 4.6 Hz, 1H), 6.95 (dd, J=8.0, 4.5 Hz, 1H), 4.34 (t, J=6.1 Hz, 2H), 4.20 (t, J=6.2 Hz, 2H), 2.30 (t, J=7.1 Hz, 2H), 2.12 (t, J=6.7 Hz, 2H), 1.73–1.84 (m, 4H), 1.34–1.41 (m, 2H), 1.10–1.22 (m, 4H), 0.85–1.08 (m, 2H); MS (ES) m/z 496 (M+H$^+$).

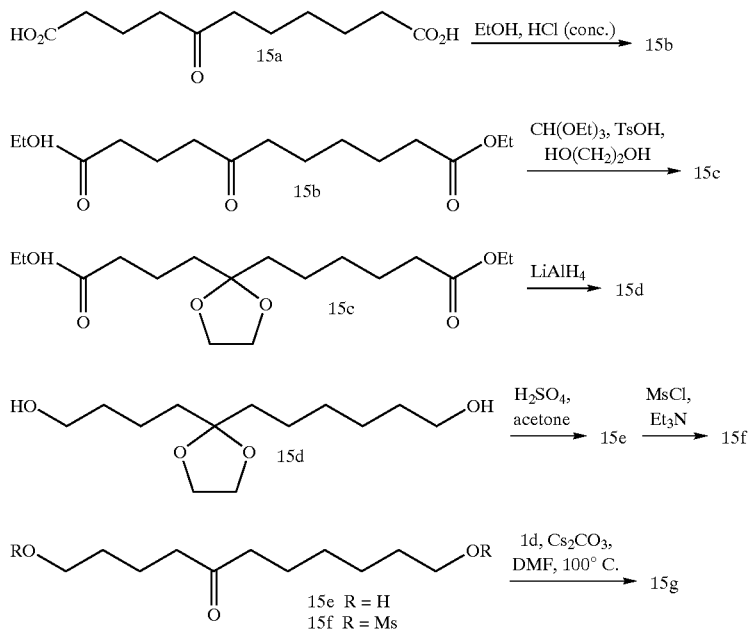

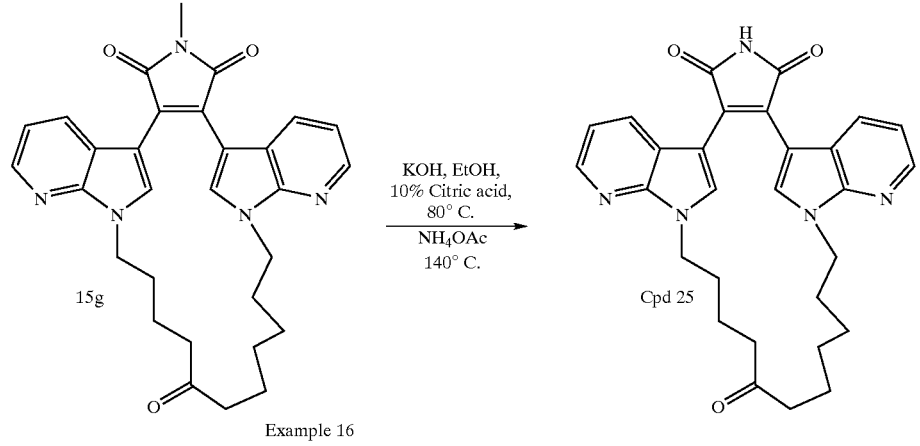

Example 16

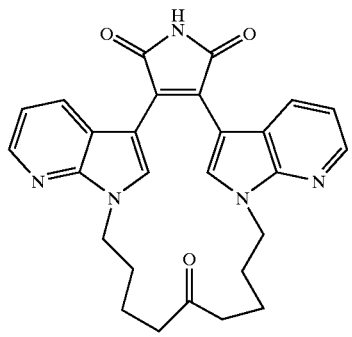

Compound 26

7,8,9,11,12,13,14,-heptahydro-6H,21H-5,24:15,20-dimethenodipyrido[2,3-b: 3',2'-h]pyrrolo[3,4-e][1,10]diazacyclononadecine-10,21,23(22H)-trione (Compound 26)
A mixture of diethyl 5-oxoazelate Compound 16a (318 mg, 1.23 mmol), TsOH

Example 16

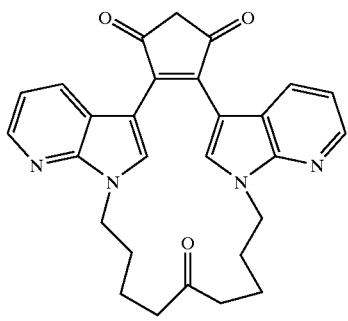

Compound 26

7,8,9,11,12,13,14,-heptahydro-6H,21H-5,24:15,20-dimethenodipyrido[2,3-b:3',2'-h]pyrrolo[3,4-e][1,10]diazacyclononadecine-10,21,23(22H)-trione (Compound 26)
A mixture of diethyl 5-oxoazelate Compound 16a (318 mg, 1.23 mmol), TsOH A mixture of diethyl 5-oxoazelate Compound 16a (318 mg, 1.23 mmol), TsOH monohydrate (19 mg, 0.10 mmol), ethylene glycol (0.35 mL, 6.20 mmol) and triethyl orthoformate (0.62 mL, 3.72 mmol) was heated to reflux for 1 h, cooled to 20° C., then diluted with saturated aqueous $NaHCO_3$ (5 mL) and extracted with diethyl ether (3×15 mL). The organic layers were combined, washed with saturated $NaHCO_3$, dried ($Na_2SO_4$) and concentrated to give a crude product Compound 16b (370 mg, 100%): MS (ES) m/z 325 (M+Na). A solution of the crude Compound 16b (370 mg, 1.23 mmol) in THF (6 mL) was added to $LiAlH_4$ (1 M in THF, 2.90 mmol). The mixture was stirred at 20° C. for 2 h and water was added to quench the excess $LiAlH_4$. The solution was then extracted with diethyl ether (3×20 mL). The organic extracts were dried over $Na_2SO_4$ and concentrated. The crude product was purified by column chromatography (eluting with EtOAc) to give Compound 16c (168 mg, 63%) as a colorless oil: $^1$H NMR (300 MHz, $CDCl_3$) δ 3.94 (s, 4H), 3.65 (t, J=6.3 Hz, 4H), 1.43–1.67 (m, 12H); MS (ES) m/z 241 (M+Na). Triethylamine (0.48 mL, 3.45 mmol) and MsCl (0.27 mL, 3.45 mmol) at 0° C. were added to a solution of Compound 16c (151 mg, 0.69 mmol) in methylene chloride (2 mL). The mixture was stirred at 20° C. for 3 h and quenched with water to give the bismesylate Compound 16d. The layers were separated and the organic phase was washed with 5% HCl, water, 5% $NaHCO_3$ and brine sequentially, then dried over $Na_2SO_4$ and concentrated. Purification with column chromatography (eluting with EtOAc/hexane) gave a ketone Compound 16e (192 mg, 84%) as a light brown oily solid: $^1$H NMR (300 MHz, $CDCl_3$) δ 4.21 (m, 4H), 3.01 (s, 6H), 2.48 (m, 2H), 1.43–1.77 (m, 10H); MS (ES) m/z 353 (M+Na).

A solution of the bismesylate ketone Compound 16e (24 mg, 0.072 mmol) in DMF (3 mL) at 70° C. was added dropwise to a mixture of Compound 12d (19 mg, 0.040 mmol), $Cs_2CO_3$ (160 mg, 0.50 mmol) and DMF (6 mL). After stirring at 70° C. for 4 h, the mixture was cooled in an ice bath, quenched with aqueous $NH_4Cl$ and extracted with EtOAc (2×30 mL). The organic extracts were combined, washed with water (3×15 mL) and brine (15 mL), then dried ($Na_2SO_4$) and concentrated to give the crude Compound 16f. The crude Compound 16f was mixed with methylene chloride (1 mL), then methanesulfonic acid (0.3 mL) was added. The mixture was stirred at 20° C. for several hours until Compound 16f was no longer detected by MS. The mixture was cooled in an ice bath, carefully quenched with ammonium hydroxide and extracted with EtOAc (3×15 mL). The extracts were washed with water (10 mL) and brine (10 mL), then dried ($Na_2SO_4$) and concentrated. The crude product was purified by column chromatography on silica gel (eluting with $MeOH/CH_2Cl_2$) to give Compound 16f (12 mg, 67% from Compound 16e) as an orange solid: $^1$H NMR (300 MHz, $CDCl_3$) δ 8.34 (d, J=3.9 Hz, 2H), 7.80 (d, J=7.9 Hz, 2H), 7.63 (s, 2H), 7.05 (dd, J=8.0, 4.7 Hz, 2H), 4.26 (t, J=6.0 Hz, 4H), 2.10 (t, J=7.0 Hz, 4H), 1.71–1.80 (m, 4H), 1.32–1/39 (m, 4H); MS (ES) m/z 468 (M+H$^+$).

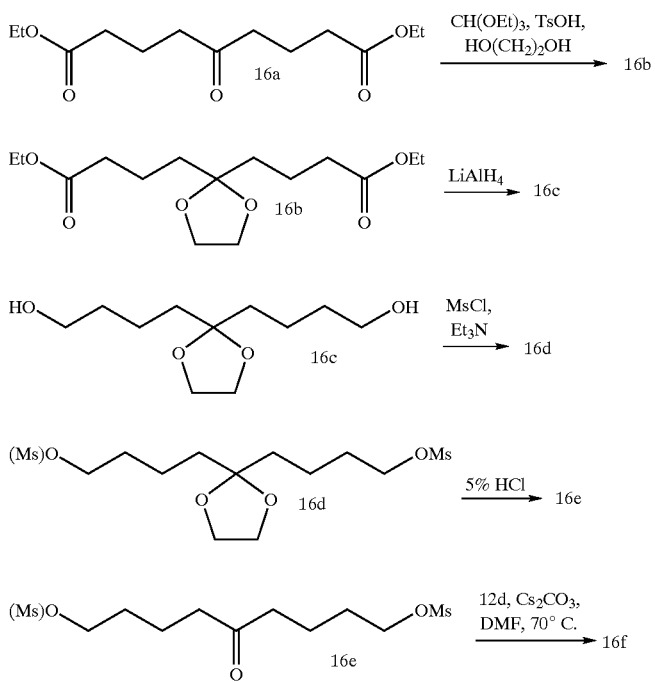

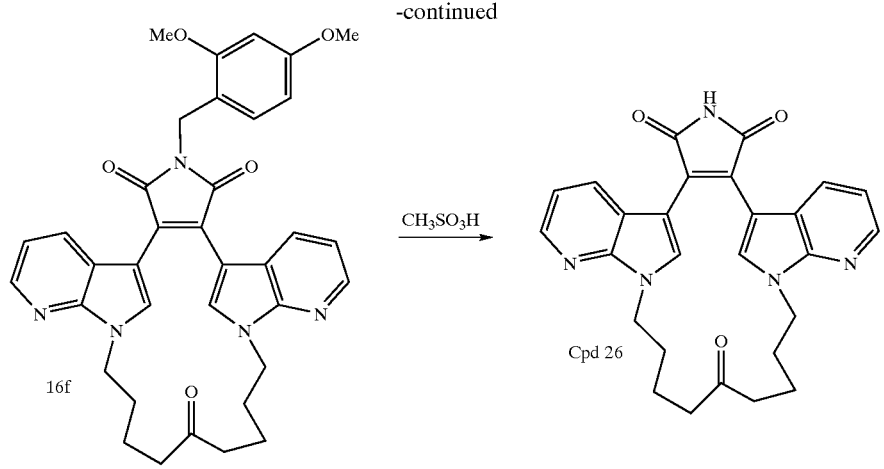

Example 17

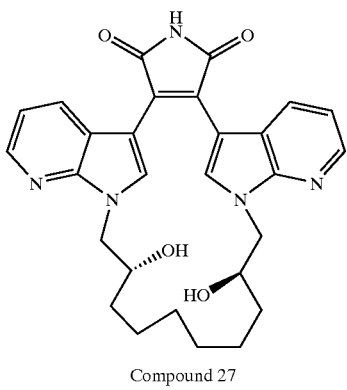

Compound 27

6,7,8,9,10,11,12,13,14,15-decahydro-7,14-dihydroxy-(7R,14R)-22H,5,25:1 6,21-dimetheno-
5H-dipyrido[2,3-b:3′,2′-h]pyrrolo[3,4-e][1,10]diazacycloeicosine-22,24(23H)-dione
(Compound 27)

Example 17

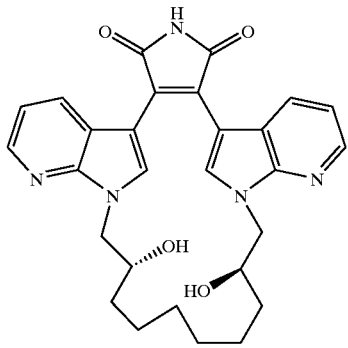

Compound 27

6,7,8,9,10,11,12,13,14,15-decahydro-7,14-dihydroxy-(7R,14R)-
22H,5,25:16,21-dimetheno-5H-dipyrido[2,3-b:3′,2′-h]
pyrrolo[3,4-e][1,10]diazacycloeicosine-22,24(23H)-dione
(Compound 27)

A mixture of Compound 1d (116 mg, 0.34 Mmol), $Cs_2CO_3$ (554 mg, 1.70 mmol) and DMF (68 mL) was heated to 60° C. and a solution of (R,R)-(+)-1,2,9,10-diepoxydecane Compound 17a (0.096 μL, 0.54 mmol) in DMF (2 mL) was added dropwise. The mixture was stirred at 60° C. for 5 h, cooled to 20° C., quenched with saturated aqueous $NH_4Cl$ (20 mL) and extracted with EtOAc (3×50 mL). The organic layers were combined, washed with water (3×15 mL) and brine (15 mL), then dried ($Na_2SO_4$) and concentrated. The residue was chromatographed on silica gel (eluting with acetone/methylene chloride) to give Compound 17b (50 mg, 34%) as an orange solid: MS (ES) m/z 514 (M+H$^+$). NaH (60% in mineral oil, 21 mg, 0.52 mmol) in DMF (10 mL) was added to a mixture of Compound 17b (47 mg, 0.092 mmol) in DMF (18 mL). The mixture was stirred at 100° C. for 20 h, cooled to 20° C., quenched with saturated aqueous $NH_4Cl$ and diluted with EtOAc. After the layers were separated, the organic phase was washed with water (3×100 mL) and brine (10 mL), then dried ($Na_2SO_4$) and concentrated. The crude product was purified by column chromatography (eluting with acetone/methylene chloride) to give Compound 17c (11 mg, 23%) as an orange solid: $^1$H NMR (300 MHz, $CD_3OD$): 8.28 (dd, J=4.7, 1.5 Hz, 2H), 7.73 (dd, J=8.0, 1.5 Hz, 2H), 7.53 (s, 2H), 7.06 (dd, J=8.0, 4.7 Hz, 2H), 4.44 (m, 2H), 4.09 (m, 2H), 3.93 (t, J=4.8 Hz, 2H), 3.13 (s, 3H), 1.15–1.28 (m, 8H), 0.87–0.89 (m, 4H); MS (ES) m/z 514 (M+H$^+$). A mixture of Compound 17c (11 mg, 0.021 mmol), ethanol (2 mL) and 10 N KOH (0.1 mL) was heated to 80° C. for 18 h. The mixture was then concentrated, diluted with water (5 mL), made acidic with 1 N HCl to a pH of 3 and extracted with $CH_2Cl_2$ (3×10 mL). The organic extracts were combined, dried ($Na_2SO_4$) and concentrated. The resulting residue was mixed with neat $NH_4OAc$ (2 g) and heated to 140° C. for 3 h. The mixture was cooled and diluted with water (5 mL), made basic with 20% aqueous NaOH and extracted with EtOAc (2×15 mL).

The organic extracts were washed with water (15 mL), then dried (Na$_2$SO$_4$) and concentrated. Purification by column chromatography (eluting with acetone/methylene chloride) gave Compound 527 (4 mg, 36%) as an orange solid: $^1$H NMR (400 MHz, CDCl$_3$): 8.32 (dd, J=4.7, 1.4 Hz, 2H), 7.80 (d, J=7.7 Hz, 2H), 7.39 (s, 2H), 7.08 (dd, J=8.0, 4.8 Hz, 2H), 4.14–4.27 (m, 4H), 3.94 (s, br, 2H), 1.17–1.20 (t, J=6.6 Hz, 4H), 0.99 (m, 4H), 0.83–0.89 (m, 4H); MS (ES) m/z 500 (M+H$^+$).

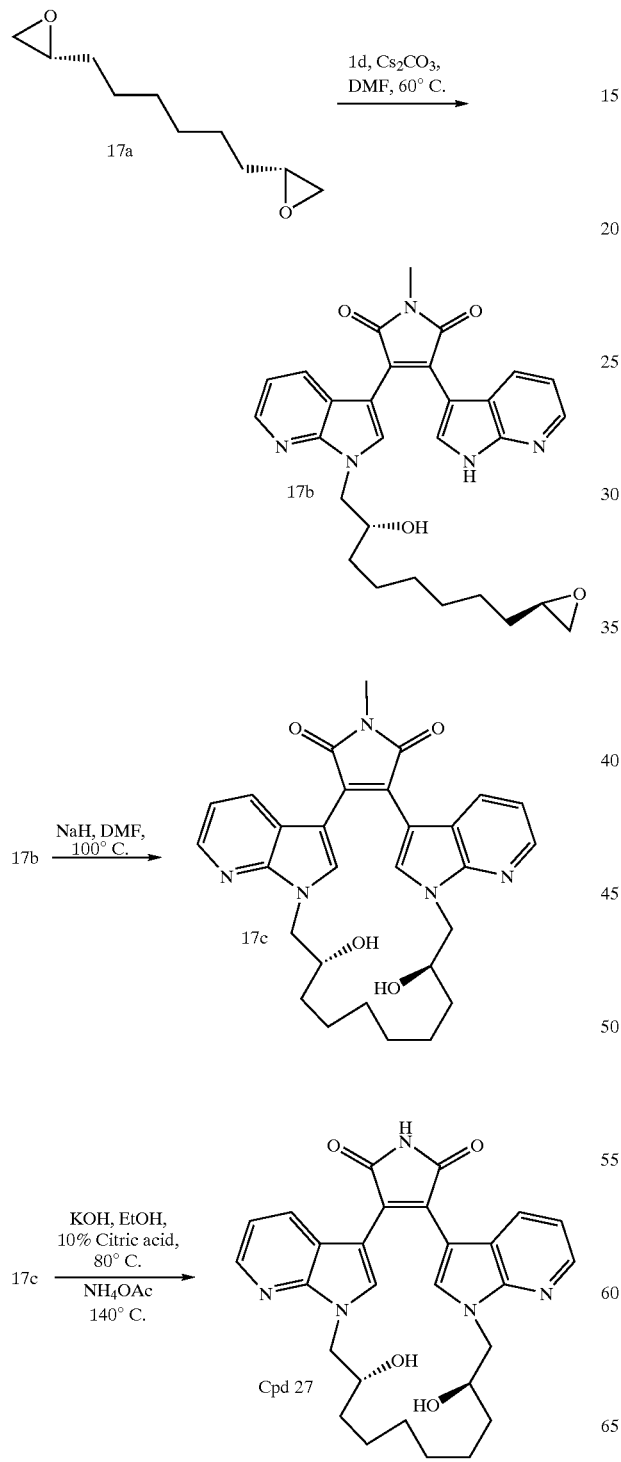

Example 18

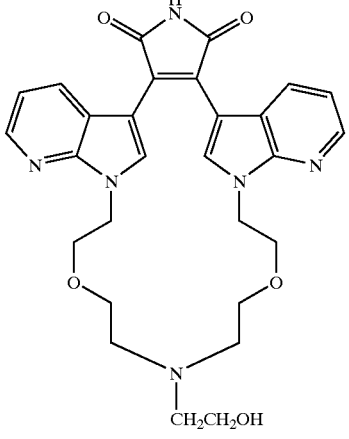

Compound 30

6,7,10,11,12,13,14,15,16-octahydro-11-(2-hydroxyethyl)-23H,5,26:17,22-dimetheno-5H,9H-dibenzo[k,q]pyrrolo[3,4-n][1,7,4,10,19]dioxatriazacycloheneicosine-23,25(24H)-dione (Compound 30)

Example 18

Compound 30

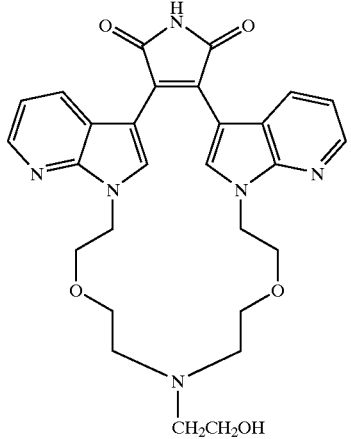

6,7,10,11,12,13,14,15,16-octahydro-11-(2-hydroxyethyl)-23H,5,26:17,22-dimetheno-5H,9H-dibenzo[k,q]pyrrolo[3,4-n][1,7,4,10,19]dioxatriazacycloheneicosine-23,25(24H)-dione (Compound 30)

A mixture of Compound 5c (3.00 g, 17.2 mmol), Compound 7a (5.35 g, 22.4 mmol) and cesium carbonate (8.41 g, 25.8 mmol) in DMF (70 mL) was stirred at 70° C. for 24 h and then filtered. The filtrate was evaporated in vacuo and the residue was separated by flash column chromatography (CH$_2$Cl$_2$/MeOH, 97:3) to give Compound 18a as a viscous oil (1.72 g, 26% yield). $^1$HNMR (CDCl$_3$) δ 7.97 (s, 1H), 7.54 (d, J=7.85 Hz, 1H), 7.32 (d, J=8.16 Hz, 1H), 7.21 (m, 2H), 4.24 (t, J=5.48, 5.50 Hz, 2H), 3.78 (t, J=5.52, 5.40 Hz, 2H), 3.74–3.64 (m, 4H), 3.43 (t, J=5.29, 4.82 Hz, 2H), 0.97 (s, 9H), 0.1 (s, 6H). ES-MS m/z 377 (MH$^+$). 1.0 M potassium t-butoxide in THF (5.2 mL, 5.2 mmol) was added dropwise to a suspension of the ester Compound 7b (771 mg, 1.9 mmol) and the amide Compound 18a (500 mg, 1.3 mmol) in dry THF (5 mL) under nitrogen that had been cooled to 0° C. The resulting mixture was stirred at 0° C. for 1 h and room temperature for 3 h, then concentrated HCl (5 mL) was added and the mixture was again stirred at room temperature for another 10 min. The mixture was partitioned between EtOAc (100 mL) and H$_2$O (40 mL), two layers were separated and the aqueous layer was extracted with EtOAc (50 mL). The combined extracts were sequentially washed with water, saturated aq. NaHCO$_3$ and brine and then dried (Na$_2$SO$_4$) and evaporated in vacuo to yield Compound 18b as a dark red-orange solid (430 mg). ES-MS m/z 504 (MH$^+$).

Ms$_2$O (740 mg, 4.25 mmol) was added to a solution of the crude Compound 18b (430 mg) and Py (pyridine) (403 mg, 5.1 mmol) in THF (17 mL). The reaction was stirred at 50° C. for 3 h and then the reaction mixture was cooled to room temperature. THF (17 mL) and 1.0 N aq. HCl (39 mL) were added and the mixture was stirred at room temperature for 10 min, then extracted with EtOAc (227 mL). The organic phase was sequentially washed with 1.0 N aq. HCl (39 mL), water and brine, and then dried (Na$_2$SO$_4$) and evaporated in vacuo to give Compound 18c as a dark red-orange solid (500 mg) ES-MS m/z 660 (MH$^+$). A solution of the crude Compound 18c (64 mg), DIEA (N,N-diisopropylethylamine) (50 mg, 0.39 mmol) and Compound 18d (12 mg, 0.2 mmol) in DMF (13 mL) in a pressure tube was stirred at 90° C. for 5 h. The volatiles were removed under vacuo and the residue was separated by flash column chromatography (CH$_2$Cl$_2$:MeOH:NH$_4$OH, 95:3:2) to give the desired product Compound 30 as a red-orange solid (10 mg). $^1$HNMR (CD$_3$OD) δ 7.50 (s, 2H), 7.40 (m, 2H), 7.08 (m, 4H), 6.83 (m, 2H), 4.27 (m, 4H), 3.77 (m, 8H), 3.21 (m, 2H). 2.83 (m, 4H), 2.69 (m, 2H). ES-MS m/z 529 (MH$^+$).

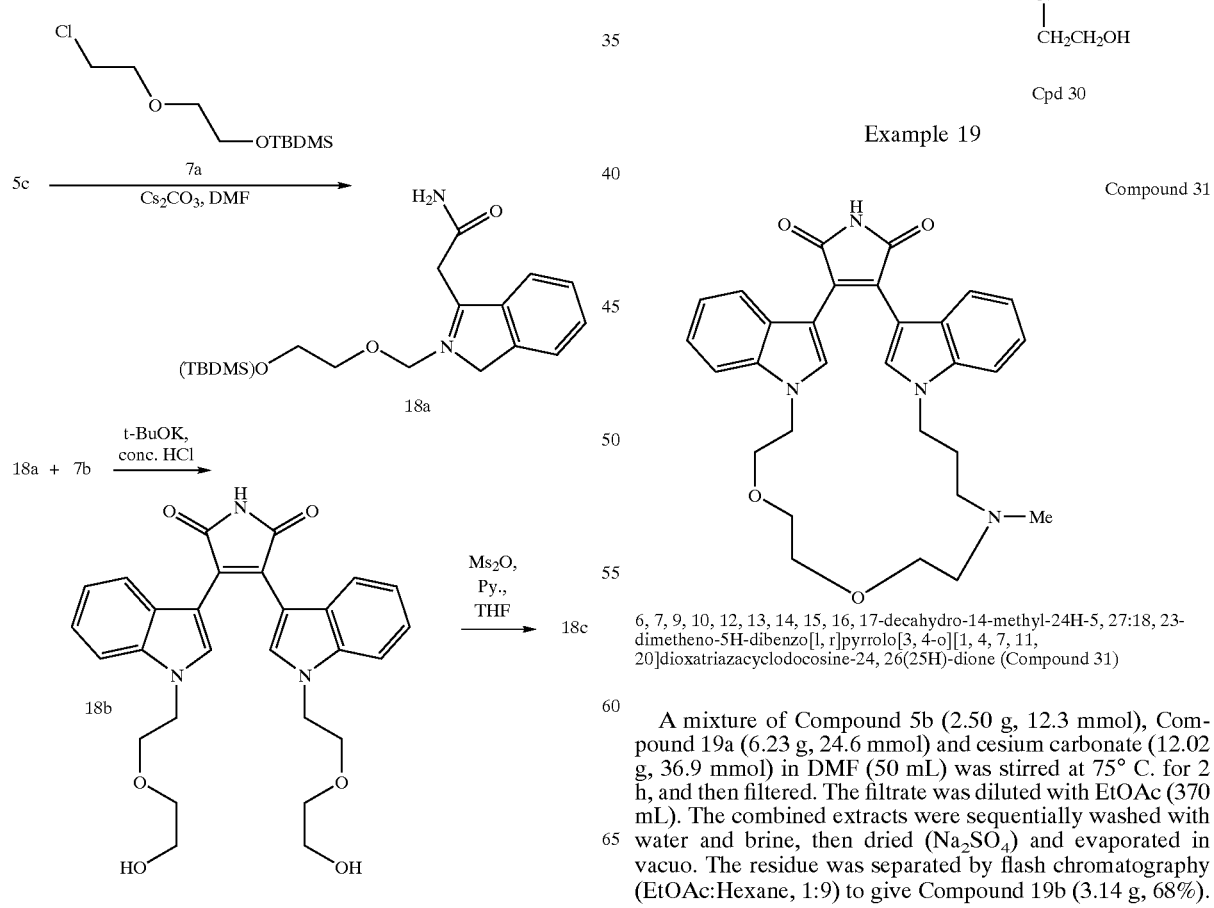

Cpd 30

Example 19

Compound 31

6, 7, 9, 10, 12, 13, 14, 15, 16, 17-decahydro-14-methyl-24H-5, 27:18, 23-dimetheno-5H-dibenzo[l, r]pyrrolo[3, 4-o][1, 4, 7, 11, 20]dioxatriazacyclodocosine-24, 26(25H)-dione (Compound 31)

A mixture of Compound 5b (2.50 g, 12.3 mmol), Compound 19a (6.23 g, 24.6 mmol) and cesium carbonate (12.02 g, 36.9 mmol) in DMF (50 mL) was stirred at 75° C. for 2 h, and then filtered. The filtrate was diluted with EtOAc (370 mL). The combined extracts were sequentially washed with water and brine, then dried (Na$_2$SO$_4$) and evaporated in vacuo. The residue was separated by flash chromatography (EtOAc:Hexane, 1:9) to give Compound 19b (3.14 g, 68%).

¹H NMR (CDCl₃) δ 8.40–8.36 (m, 1H), 8.31 (s, 1H), 7.38–7.19 (m, 3H), 4.27 (t, J=6.84, 6.82 Hz, 2H), 3.81 (s, 3H), 3.63–3.50 (m, 2H), 2.04–1.96 (m, 2H), 0.87 (s, 9H), 0.01 (s, 6H). ES-MS m/z 376 (MH⁺). A mixture of Compound 5c (2.50 g, 14.3 mmol), 2-[2-(2-chloroethoxyl) ethoxyl]ethanol Compound 19c (4.82 g, 28.6 mmol) and cesium carbonate (13.98 g, 42.9 mmol) in DMF (58 mL) was stirred at 78° C. for 24 h. Additional Compound 19c was added and the reaction stirred for 24 h at 78° C. and was then filtered. The filtrate was diluted with EtOAc (430 mL) and the combined extracts were sequentially washed with water and brine, then dried (Na₂SO₄) and evaporated in vacuo. The residue was separated by flash chromatography (CH₂Cl₂/MeOH, 93:7) to give Compound 19d (3.60 g, 82%). ¹H NMR (CDCl₃) δ 7.58 (d, J=7.80 Hz, 1H), 7.36–7.30 (m, 1H), 7.26–7.21 (m, 1H), 7.17–7.11 (m, 2H), 4.29 (t, J=5.3, 2H), 3.94–3.79 (m, 2H), 3.69 (s, 2H), 3.59–3.48 (m, 8H). ES-MS m/z 307 (MH⁺).

1.0 M potassium t-butoxide in THF (6.8 mL, 6.8 mmol) was added dropwise to a suspension of the ester Compound 19b (939 mg, 2.5 mmol) and the amide Compound 19d (520 mg, 1.7 mmol) in dry THF (7 mL) under nitrogen that had been cooled to 0° C. The resulting mixture was stirred at 0° C. for 1 h and room temperature for 3 h and then concentrated HCl (7 mL) was added. The mixture was then stirred at rt for another 10 min. and then partitioned between EtOAc (142 mL) and H₂O (57 mL). Two layers were separated and the aqueous layer was extracted with EtOAc (60 mL). The combined extracts were sequentially washed with water, saturated aq. NaHCO₃ and brine, then dried (Na₂SO₄) and evaporated in vacuo to yield Compound 19e as a dark red-orange solid (703 mg). ES-MS m/z 518 (MH⁺). Ms₂O (1.13 g, 6.5 mmol) was added to a solution of the crude Compound 19e (700 mg) and Py (pyridine) (617 mg, 7.8 mmol) in THF (26 mL). The reaction mixture was stirred at 50° C. for 2.5 h and then cooled to rt. Then THF (26 mL) and 1.0 N aq. HCl (43 mL) were added. The mixture was stirred at room temperature for 10 min and then extracted with EtOAc (347 mL). The organic phase was washed with 1.0 N aq. HCl (143 mL), then water, brine, and then dried (Na₂SO₄), and evaporated in vacuo to give Compound 19f as a dark red-orange solid (850 mg). ES-MS m/z 674 (MH⁺). A solution of the crude Compound 19f (81 mg), DIEA (310 mg, 2.4 mmol) and MeNH₂ (2.0 M in THF, 1.1 mL, 2.2 mmol) in DMF (15 mL) in a pressure tube was stirred at 90° C. for 24 h. The volatiles were removed under vacuo and the residue was separated by flash column chromatography (CH₂Cl₂:MeOH:NH₄OH, 95:3:2) to give the desired product Compound 31 as a red-orange solid (9 mg), ES-MS m/z 513 (MH⁺).

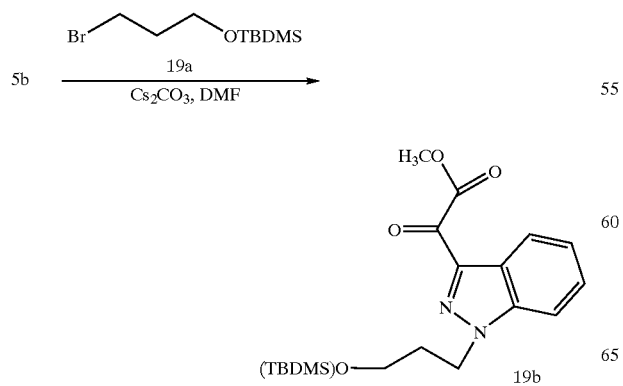

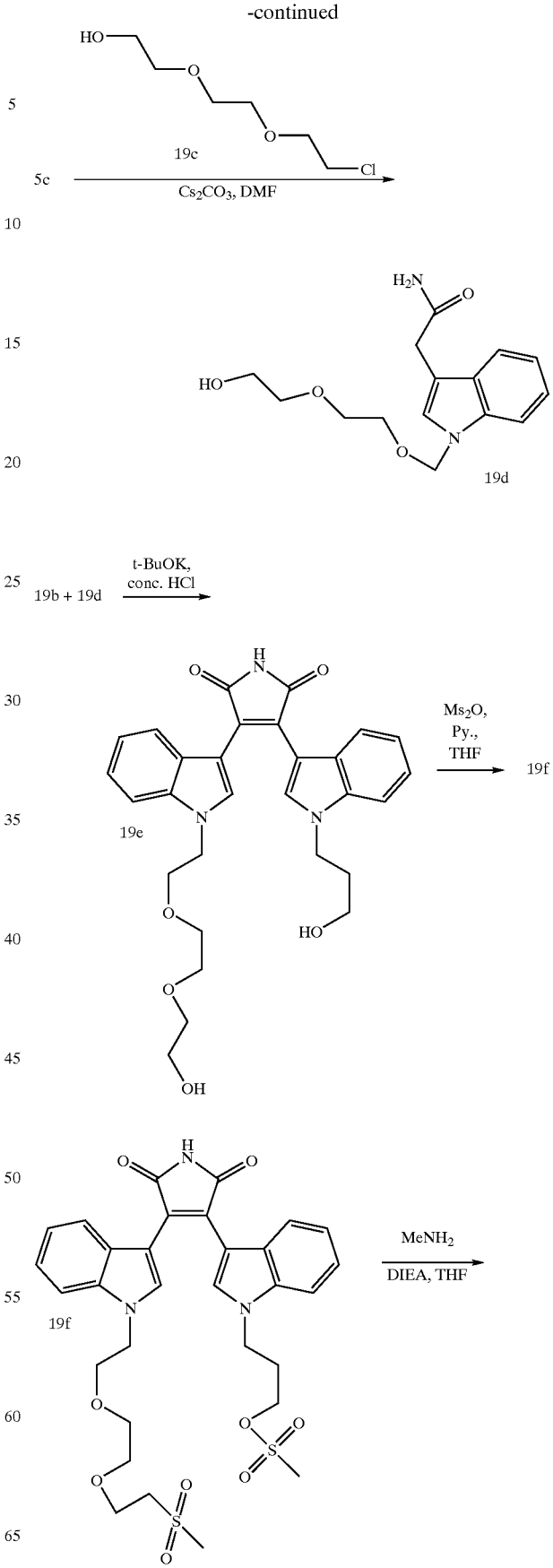

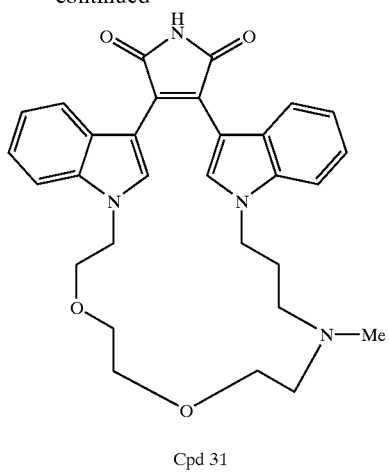

Cpd 31

BIOLOGICAL EXAMPLES

The compounds of the present invention were tested for biological activity in the following in-vitro and in-vivo methods.

Example 1
Protein Kinase C Scintillation Proximity Assay (SPA)

The binding activity of a compound for Protein Kinase C (PKC) was assessed using a homogeneous Scintillation Proximity Assay according to the procedure below.

Procedure

The different human PKC isozymes (were obtained from PanVera, Madison Wis. and had been prepared as recombinant enzymes produced from a baculovirus expression vector) were added to a reaction mixture containing a test compound, 20 mM HEPES (pH 7.4), 100 μM CaCl$_2$, 10 mM MgCl$_2$, 100 μg/mL phosphatidylserine, 20 μg/mL diacylglycerol, 1 μM ATP, 0.8 μCi ($^{33}$P)ATP, and 5 μg/mL biotinylated substrate peptide (Jing Zhao et al., *J. Bio. Chem.*, 1998, 273, 23072). The reaction was incubated for 15 min at 30° C. Reactions were terminated by the addition of streptavidin-coated SPA beads (Amersham) in a solution containing 1 mM EGTA, 10 mM EDTA and 100 μM ATP. Beads were allowed to settle overnight and the plates read in a Wallac MICROBETA scintillation counter (PerkinElmer Life sciences, Wellesley, Mass.).

Glycogen Synthase Kinase 3-β Assay

The inhibitory activity of a compound against Glycogen Synthase Kinase 3-β (GSK 3-β) activity was assessed using a recombinant rabbit GSK 3-β according to the procedure below.

Procedure

The test compound was added to a reaction mixture containing Protein phosphatase inhibitor-2 (PPI-2) (Calbiochem, San Diego Calif.) (45 ng), rabbit GSK-3-β (New England Biolabs, Beverly Mass.) (0.75 units) and $^{33}$P—ATP (1 uCi) in 50 mM Tris-HCl (pH 8.0), 10 mM MgCl$_2$, 0.1% BSA, 1 mM DTT, and 100 uM Sodium Vanadate. The mixture was reacted for 90 minutes at 30° C. to allow phosphorylation of the PPI-2 protein and then the protein in the reaction was precipitated using 10% trichloroacetic acid (TCA). The precipitated protein was collected on filter plates (MultiScreen-DV, Millipore, Bedford Mass.), which were subsequently washed. Finally, the radioactivity was quantified using a TopCount Scintillation Counter (Packard, Meridian Conn.). GSK-3 inhibitory compounds resulted in less phosphorylated PPI-2 and thus a lower radioactive signal in the precipitated protein. Staurosporine or Valproate (both available from several commercial sources), known inhibitors of GSK-3-β, were used as a positive control for screening.

Values for inhibition of various PKC isozymes and GSK 3-β by certain compounds of the invention tested in the PKC SPA and GSK 3-β assays are shown in Table 1.

TABLE 1

| | PKC and GSK-3 Selectivity | | | | |
|---|---|---|---|---|---|
| Cpd | PKC-α (μM) | PKC-βI (μM) | PKC-βII (μM) | PKC-γ (μM) | GSK 3-β (μM) |
| 1 | 25.79 | 18.48 | 2.413 | 38.74 | 0.027 |
| 2 | >100 | >100 | >100 | >100 | 0.032 |
| 3 | >100 | >100 | >100 | >100 | 0.033 |
| 4 | 1.22 | 1.587 | 0.099 | 3.461 | 0.102 |
| 5 | 0.412 | 0.349 | 0.016 | 1.347 | 0.049 |
| 6 | 2.56 | 1.477 | 0.212 | 4 | 0.045 |
| 7 | 2.59 | 3.067 | 0.285 | 3.265 | 0.033 |
| 8 | 1.53 | 1.78 | 0.288 | 0.783 | 0.233 |
| 9 | 0.319 | 0.338 | 0.035 | 0.228 | 0.164 |
| 10 | 5.36 | 5.15 | 0.519 | 7.8 | 0.128 |
| 11 | 1.215 | 1.056 | 0.072 | 2.852 | 0.015 |
| 12 | 0.02 | ND | 0.008 | 0.15 | 0.033 |
| 13 | 0.05 | ND | 0.04 | 0.37 | ND |
| 14 | 0.019 | ND | 0.015 | 0.034 | 0.076 |
| 15 | 0.042 | ND | 0.027 | 0.022 | 0.093 |
| 16 | — | — | 0.063 | — | 37% @ 0.1 μM |
| 17 | — | — | 0.385 | — | 31% @ 0.2 μM |
| 18 | — | — | — | — | 9.2 |
| 19 | — | — | — | — | 0.11 |
| 20 | — | — | — | — | 0.61 |
| 21 | — | — | — | — | 1.44 |
| 22 | — | — | — | — | 30% @ 1 μM |
| 23 | — | — | — | — | 46% @ 1 μM |
| 24 | — | — | — | — | 0.21 |
| 25 | — | — | — | — | 0.08 |
| 26 | — | — | — | — | 0.09 |
| 27 | — | — | — | — | 1.18 |
| 28 | — | — | — | — | 48% @ 0.5 μM |
| 29 | — | — | 0.369 | — | 30% @ 0.1 μM |
| 30 | — | — | 0.011 | — | 0.064 |
| 31 | 0.014 | — | 0.007 | 0.024 | — |

Example 2
Biotinylated Peptide Substrate Assay

Assays to test inhibition of a compound for other kinases were preformed using methods that measure the amount of phosphorylation of a biotinylated peptide substrate. Biotinylated peptide substrates were selected from the literature as appropriate for the enzyme being evaluated.

Procedure

A kinase reaction mix was prepared in 50 mM Tris-HCl pH=8, 10 mM MgCl$_2$, 0.1 mM Na$_3$VO$_4$, 1 mM DTT, 10 μM ATP, 0.25–1 μM biotinylated peptide substrate, 0.2–0.8 μCuries per well $^{33}$P-γ-ATP (2000–3000 Ci/mmol). Assay conditions vary slightly for each protein kinase, for example, insulin receptor kinase requires 10 mM MnCl$_2$ for activity and Calmodulin-dependent protein kinase requires calmodulin and 10 mM CaCl$_2$. The reaction mixture was dispensed into the wells of a streptavidin coated Flashplate and 1 μL drug stock in 100% DMSO was added to a 100 μL reaction volume resulting in a final concentration of 1% DMSO in the reaction. Enzyme was diluted in 50 mM Tris-HCl pH=8.0, 0.1% BSA and added to each well. The reaction was incubated for one hour at 30° C. in the presence of compound. After one hour the reaction mix was aspirated from the plate and the plate was washed with PBS containing 100 mM EDTA. The plate was read on a scintillation counter to determine $^{33}$P-γ-ATP incorporated into the immobilized peptide. Test compounds were assayed in duplicate at 8 concentrations (100 uM, 10 uM, 1 uM, 100 nM, 10 nM, 1 nM, 100 pM, 10 pM). A maximum and minimum signal for the assay was determined on each plate.

The IC$_{50}$ was calculated from the dose response curve of the percent inhibition of the maximum signal in the assay according to the formula:

% Inhibition=((MS−BS)/(TCS−BS))×100% where MS=Maximum Signal, BS=Background Signal, TCS=Test Compound Signal. The percent inhibition was graphed against the log concentration of the test compound. Known inhibitor compounds as appropriate references for the kinase being assayed were also included on each plate.

Definition and Source of Kinase Enzymes.

VEGF-R (vascular endothelial growth factor receptor-2) is a fusion protein containing a polyhistidine tag at the N-terminus followed by amino acids 786–1343 of the rat VEGF-R2 kinase domain (GenBank Accession #U93306). Protein Kinase A is the catalytic subunit of cAMP dependent protein kinase-A purified from bovine heart (Upstate Biotech, Lake Placid, N.Y., Cat#14–114). CDK1 (cyclin dependent kinase 1) is isolated from insect cells expressing both the human CDK1 catalytic subunit and its positive regulatory subunit cyclin B (New England Biolabs, Beverly, Mass., Cat. #6020). Casein Kinase-1 is a protein truncation at amino acid 318 of the C-terminal portion of the rat CK1 delta isoform produced in *E.coli* (New England Biolabs, Beverly, Mass., Cat. #6030). Insulin Receptor Kinase consists of residues 941–1313 of the cytoplasmic domain of the beta-subunit of the human insulin receptor (BIOMOL, Plymouth Meeting, Pa., Cat. #SE-195). Calmodulin Kinase (calmodulin-dependent protein kinase 2) is a truncated version of the alpha subunit of the rat protein produced in insect cells (New England Biolabs, Beverly, Mass., Cat. #6060). MAP Kinase is the rat ERK-2 isoform containing a polyhistidine tag at the N-terminus produced in *E.coli* and activated by phosphorylation with MEK1 prior to purification (BIOMOL, Plymouth Meeting, Pa., Cat. #SE-137). EGFR (epidermal growth factor receptor) is purified from human A431 cell membranes (Sigma, St. Louis, Mo., Cat.# E3641).

| Peptide Substrates | |
|---|---|
| VEGF-R | (Biotin)KHKKLAEGSAYEEV-Amide |
| CDK1 | (Biotin)KTPKKAKKPKTPKKAKKL-Amide |
| Caseine Kinase-1 | (Biotin)KRRRALS(phospho)VASLPGL-Amide |
| EGF-R | (Biotin)Poly GT (4:1) |
| Calmodulin Kinase-2 | (Biotin)KKALRRQETVDAL-Amide |
| MAP Kinase ERK-2 | (Biotin)APRTPGGRR-Amide |
| Insulin receptor Kinase | (Biotin)Poly GT (4:1) |
| Protein Kinase A | (Biotin)GRTGRRNSI-Amide |

IC$_{50}$ data for certain compounds of the invention tested against various kinases are shown in Table 2. For compounds where a kinase IC$_{50}$ value is >10, there was no observed 50% inhibition at the highest dose tested for that kinase nor was an inhibition maxima observed.

TABLE 2

Selectivity Assays against other Kinases

| Kinase Assay (IC$_{50}$ uM) | Cpd 1 | Cpd 2 | Cpd 10 | Cpd 11 |
|---|---|---|---|---|
| VEGF-R | >10 | >10 | 1.199 | 0.889 |
| CDK1 | >10 | >10 | 0.422 | 0.457 |
| Casein Kinase 1 | >10 | >10 | >10 | >10 |
| EGF-R | >10 | >10 | >10 | >10 |
| Calmodulin Kinase 2 | >10 | >10 | >10 | >10 |
| Map kinase ERK-2 | >10 | >10 | >10 | >10 |
| Insulin-R kinase | >10 | >10 | >10 | >10 |
| PKC α | >10 | >10 | >10 | >10 |

Example 3

Cell-Based GSK 3-β Assay

Glycogen content of L6 muscle cells was measured according to the method described in Berger and Hayes, *Anal. Biochem.*, 1998, 261, 159–163.

Procedure

Briefly, L6 cells were serum starved overnight in alpha-MEM containing 0.1%. On the following day, cells were washed three times with 300 μL KRPH buffer (150 mM NaCl, 5 mM KCl, 2.9 mM Na$_2$HPO$_4$, 1.25 mM MgSO$_4$, 1.2 mM CaCl$_2$, 10 mM HEPES, pH 7.4) and labeled with 200 μL alpha-MEM containing 5.5 mM $^{14}$C-Glucose (0.1 μCi) in the presence of vehicle (DMSO) or compounds. After 2 hours, cells were washed three times with ice-cold PBS and glycogen was precipitated for 2 hours using ice-cold 66% EtOH. Precipitated glycogen was then washed three times with ice-cold 66% EtOH and $^{14}$C-glycogen was quantified using a TopCount (Packard).

As shown in Table 3, L6 skeletal muscle cells demonstrated increased glycogen synthesis upon exposure to Compounds 1, 2 and 5. Compounds were tested in separate experiments at the dose levels shown. Where shown, the 0.0 μM dose was used as a control.

TABLE 3

| | $^{14}$C-Glucose Incorporation (dpm) | | |
|---|---|---|---|
| Dose (μM) | Cpd 1 | Cpd 2 | Cpd 5 |
| 0.0 | 1640 | 2078 | — |
| 0.01 | — | — | 2884 |
| 0.1 | — | — | 2988 |
| 0.3 | — | — | 3339 |
| 1 | 1898 | 2224 | — |
| 3 | 1958 | 2518 | 3438 |
| 10 | 2426 | 2806 | 4700 |

What is claimed is:

1. A compound of Formula (Ia1):

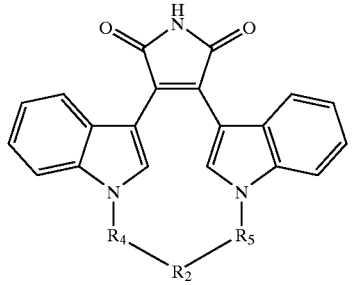

Formula (Ia1)

wherein $R_4$, $R_2$ and $R_5$ are dependently selected from:

| $R_4$ | $R_2$ |
|---|---|
| —(CH₂)₂— | —O—(CH₂)₂—O— |
| —(CH₂)₂— | —O—(CH₂)₂—O—(CH₂)₂—O— |
| —(CH₂)₂— | —O—(CH₂)₂—O—(CH₂)₂—O—(CH₂)₂—O— |
| —(CH₂)₂— | —O—(CH₂)₂—O—(CH₂)₂—O—(CH₂)₂—O—(CH₂)₂—O— |
| —(CH₂)₂— | —O—(CH₂)₂—N(Et)—(CH₂)₂—O— |
| —(CH₂)₂— | —O—(CH₂)₂—N(Me)—(CH₂)₂—O— |
| —(CH₂)₂— | —O—(CH₂)₂—N(i-Pr)—(CH₂)₂—O— |
| —(CH₂)₂— | —N(Me)—(CH₂)₂—N(Me)—(CH₂)₂—N(Me)— |
| —(CH₂)₂— | —O—(CH₂)₂—N(2-hydroxy-Et)—(CH₂)₂—O— |
| and, | |
| —(CH₂)₂— | —O—(CH₂)₂—O—(CH₂)₂—N(Me)— |

| $R_5$ |
|---|
| —(CH₂)₂—; |
| —(CH₂)₂—; |
| —(CH₂)₂—; |
| —(CH₂)₂—; |
| —(CH₂)₂—; |
| —(CH₂)₂—; |
| —(CH₂)₂—; |
| —(CH₂)₂—; |
| —(CH₂)₂—; |
| —(CH₂)₃—. |

2. A compound of Formula (Ib1):

Formula (Ib1)

wherein $R_4$, $R_2$ and $R_5$ are dependently selected from:

| $R_4$ | $R_2$ | $R_5$ |
|---|---|---|
| —(CH₂)₂— | —O—(CH₂)₂—O—(CH₂)₂—O— | —(CH₂)₂—; |
| —(CH₂)₂— | —O—(CH₂)₂—O—(CH₂)₂—O—(CH₂)₂—O— | —(CH₂)₂—; |
| —(CH₂)₂— | —O—(CH₂)₂—O—(CH₂)₂—O—(CH₂)₂—O—(CH₂)₂—O— | —(CH₂)₂—; |
| —(CH₂)₂— | —O—(CH₂)₂—N(Et)—(CH₂)₂—O— | —(CH₂)₂—; |
| —(CH₂)₂— | —O—(CH₂)₂—S—(CH₂)₂—O— | —(CH₂)₂—; |
| —(CH₂)₅— | —NH— | —(CH₂)₅—; |
| —(CH₂)₅— | —N(Et)— | —(CH₂)₅—; |
| —(CH₂)₅— | —NH— | —(CH₂)₄—; |
| —(CH₂)₅— | —N(Et)— | —(CH₂)₄—; |
| —(CH₂)₄— | -2,6-pyridinyl- | —(CH₂)₄—; |
| —(CH₂)₄— | —C(O)—(CH₂)₂— | —(CH₂)₄—; |
| —CH₂— | —CH[R](OH)—(CH₂)₆—CH[R](OH)— | —CH₂—; |
| and, | | |
| —(CH₂)₂— | —O—(CH₂)₂—O— | —(CH₂)₂—. |

3. A compound of Formula (If1):

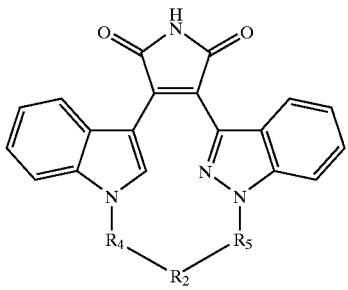

Formula (If1)

wherein $R_4$, $R_2$ and $R_5$ are dependently selected from:

| $R_4$ | $R_2$ | $R_5$ |
|---|---|---|
| —(CH$_2$)$_2$— | —O—(CH$_2$)$_2$—N(Me)—(CH$_2$)$_2$—O— | —(CH$_2$)$_2$—; |
| —(CH$_2$)$_2$— and, | —O—(CH$_2$)$_2$—N(Et)—(CH$_2$)$_2$—O— | —(CH$_2$)$_2$—; |
| —(CH$_2$)$_2$— | —O—(CH$_2$)$_2$-N(2-OMe—Et)—(CH$_2$)$_2$—O— | —(CH$_2$)$_2$—. |

4. A compound of Formula (Ii1):

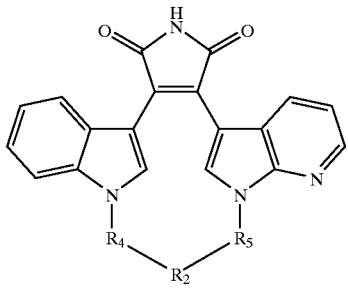

Formula (Ii1)

wherein $R_4$, $R_2$ and $R_5$ are dependently selected from:

| $R_4$ | $R_2$ | $R_5$ |
|---|---|---|
| —CH$_2$— and, | -1,3-phenyl- | —CH$_2$—; |
| —CH$_2$— | -2,6-pyridinyl- | —CH$_2$—. |

5. A compound of Formula (Ij1):

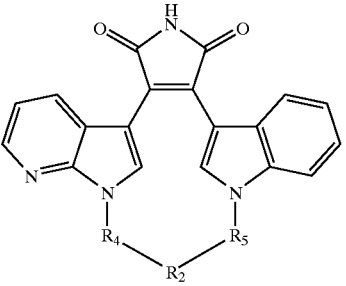

Formula (Ij1)

wherein $R_4$, $R_2$ and $R_5$ are dependently selected from:

| $R_4$ | $R_2$ | $R_5$ |
|---|---|---|
| —(CH$_2$)$_2$— and, | —O—(CH$_2$)$_2$—O— | —(CH$_2$)$_2$—; |
| —(CH$_2$)$_2$— | —O—(CH$_2$)$_2$—O—(CH$_2$)$_2$—O— | —(CH$_2$)$_2$—. |

* * * * *